United States Patent
Puri et al.

(10) Patent No.: US 8,524,681 B2
(45) Date of Patent: Sep. 3, 2013

(54) SIRNA SEQUENCE-INDEPENDENT MODIFICATION FORMATS FOR REDUCING OFF-TARGET PHENOTYPIC EFFECTS IN RNAI, AND STABILIZED FORMS THEREOF

(75) Inventors: Nitin Puri, Austin, TX (US); Irudaya Charles, Austin, TX (US); Susan Magdaleno, Austin, TX (US); Alexander Vlassov, Austin, TX (US); Chris Burnett, Austin, TX (US)

(73) Assignee: Applied Biosystems, LLC, Carlsbad, CA (US)

( * ) Notice: Subject to any disclaimer, the term of this patent is extended or adjusted under 35 U.S.C. 154(b) by 449 days.

(21) Appl. No.: 12/727,336

(22) Filed: Mar. 19, 2010

(65) Prior Publication Data

US 2010/0222414 A1    Sep. 2, 2010

Related U.S. Application Data

(63) Continuation of application No. PCT/US2008/076675, filed on Sep. 17, 2008.

(60) Provisional application No. 60/973,548, filed on Sep. 19, 2007.

(51) Int. Cl.
- *C07H 21/02* (2006.01)
- *C07H 21/04* (2006.01)
- *A61K 31/70* (2006.01)
- *C12Q 1/68* (2006.01)

(52) U.S. Cl.
USPC ....... 514/44 A; 536/23.1; 536/24.1; 536/24.5; 435/375; 435/377

(58) Field of Classification Search
None
See application file for complete search history.

(56) References Cited

U.S. PATENT DOCUMENTS

| | | |
|---|---|---|
| 5,898,031 A | 4/1999 | Crooke |
| 6,005,087 A | 12/1999 | Cook et al. |
| 6,083,482 A | 7/2000 | Wang |
| 6,107,094 A | 8/2000 | Crooke |
| 6,268,490 B1 | 7/2001 | Imanishi et al. |
| 6,476,205 B1 | 11/2002 | Buhr et al. |
| 6,506,559 B1 | 1/2003 | Fire et al. |
| 6,639,059 B1 | 10/2003 | Kochkine et al. |
| 6,670,461 B1 | 12/2003 | Wengel et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 7,022,828 B2 | 4/2006 | McSwiggen et al. |
| 7,034,133 B2 | 4/2006 | Wengel et al. |
| 7,053,195 B1 | 5/2006 | Goff |
| 7,053,207 B2 | 5/2006 | Wengel |
| 7,056,704 B2 | 6/2006 | Tuschl et al. |
| 7,060,809 B2 | 6/2006 | Wengel et al. |
| 7,078,196 B2 | 7/2006 | Tuschl et al. |
| 7,084,125 B2 | 8/2006 | Wengel |
| 7,176,304 B2 | 2/2007 | McSwiggen et al. |
| 7,422,853 B1 | 9/2008 | Huang et al. |
| 7,432,249 B2 | 10/2008 | Crooke |
| 7,452,987 B2 | 11/2008 | Giese et al. |
| 7,569,575 B2 | 8/2009 | Sorensen et al. |
| 7,572,582 B2 | 8/2009 | Wengel et al. |
| 7,629,321 B2 | 12/2009 | Crooke |
| 7,687,617 B2 | 3/2010 | Thrue et al. |
| 7,695,902 B2 | 4/2010 | Crooke |
| 7,696,345 B2 | 4/2010 | Allerson et al. |
| 7,737,125 B2 | 6/2010 | Worm |
| 7,750,131 B2 | 7/2010 | Seth et al. |
| 7,750,144 B2 | 7/2010 | Zamore et al. |
| 7,772,203 B2 | 8/2010 | Zamore et al. |
| 7,772,387 B2 | 8/2010 | Manoharan et al. |
| 7,786,290 B2 | 8/2010 | Woppmann et al. |
| 7,834,170 B2 | 11/2010 | Khvorova et al. |
| 7,834,171 B2 | 11/2010 | Leake et al. |
| 2002/0086356 A1 | 7/2002 | Tuschl et al. |
| 2002/0165189 A1 | 11/2002 | Crooke |
| 2003/0077609 A1 | 4/2003 | Jakobsen et al. |
| 2003/0108923 A1 | 6/2003 | Tuschl et al. |
| 2003/0224377 A1 | 12/2003 | Wengel et al. |
| 2004/0014108 A1 | 1/2004 | Eldrup et al. |
| 2004/0096848 A1 | 5/2004 | Thrue et al. |
| 2004/0147022 A1 | 7/2004 | Baker et al. |
| 2004/0171031 A1 | 9/2004 | Baker et al. |
| 2004/0171033 A1 | 9/2004 | Baker et al. |
| 2004/0171570 A1 | 9/2004 | Allerson et al. |
| 2004/0192626 A1 | 9/2004 | McSwiggen et al. |
| 2004/0198640 A1 | 10/2004 | Leake et al. |
| 2004/0203024 A1 | 10/2004 | Baker et al. |

(Continued)

FOREIGN PATENT DOCUMENTS

| | | |
|---|---|---|
| CA | 2359180 | 7/2001 |
| EP | 1144623 | 1/2000 |

(Continued)

OTHER PUBLICATIONS

Communication pursuant to Article 94(3) mailed Oct. 19, 2010 in EP Appl. No. 08831316.8.
Communication pursuant to Article 94(3) mailed Aug. 25, 2011 in EP Appl. No. 08831316.8.
First Office Action mailed Oct. 19, 2011 in Appl. No. 200880113683.4.

(Continued)

*Primary Examiner* — Sean McGarry

(57) ABSTRACT

Modification formats having modified nucleotides are provided for siRNA. Short interfering RNA having modification formats and modified nucleotides provided herein reduce off-target effects in RNA interference of endogenous genes. Further modification formatted siRNAs are demonstrated to be stabilized to nuclease-rich environments. Unexpectedly, increasing or maintaining strand bias, while necessary to maintain potency for endogenous RNA interference, is not sufficient for reducing off-target effects in cell biology assays.

15 Claims, 47 Drawing Sheets

(56) References Cited

U.S. PATENT DOCUMENTS

Figure 2A:
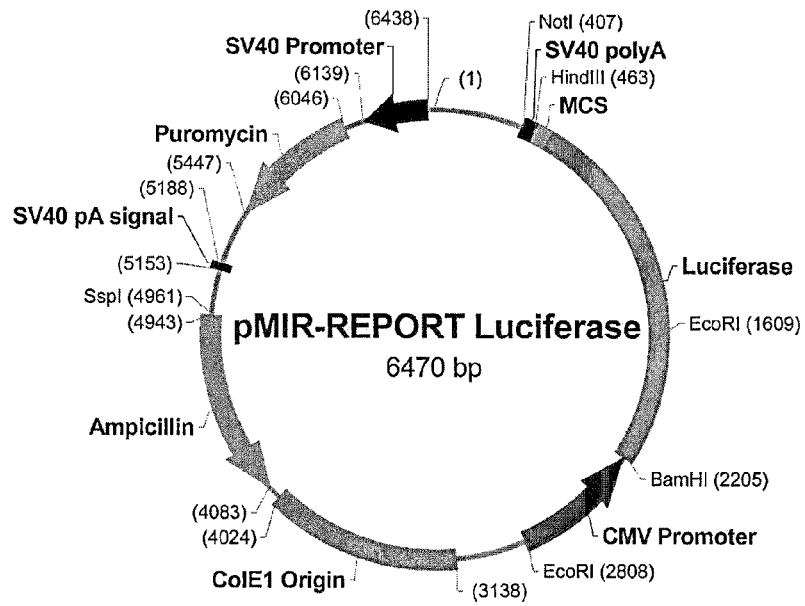

| | | |
|---|---|---|
| 2004/0203145 A1 | 10/2004 | Zamore et al. |
| 2004/0219565 A1 | 11/2004 | Kauppinen et al. |
| 2004/0241717 A1 | 12/2004 | Hansen et al. |
| 2004/0248840 A1 | 12/2004 | Hansen et al. |
| 2004/0266707 A1 | 12/2004 | Leake et al. |
| 2005/0014712 A1 | 1/2005 | Hansen et al. |
| 2005/0020521 A1 | 1/2005 | Rana |
| 2005/0020525 A1 | 1/2005 | McSwiggen et al. |
| 2005/0038239 A1 | 2/2005 | Catchpole |
| 2005/0053981 A1 | 3/2005 | Swayze et al. |
| 2005/0058982 A1 | 3/2005 | Han et al. |
| 2005/0059066 A1 | 3/2005 | Swayze et al. |
| 2005/0119214 A1 | 6/2005 | Manoharan et al. |
| 2005/0181382 A1 | 8/2005 | Zamore et al. |
| 2005/0203042 A1 | 9/2005 | Frieden et al. |
| 2005/0223427 A1 | 10/2005 | Leake et al. |
| 2005/0244858 A1 | 11/2005 | Rossi et al. |
| 2005/0256071 A1 | 11/2005 | Davis |
| 2005/0266418 A1 | 12/2005 | Chen et al. |
| 2005/0287566 A1 | 12/2005 | Wengel et al. |
| 2006/0003349 A1 | 1/2006 | Dempcy et al. |
| 2006/0078906 A1 | 4/2006 | Chen et al. |
| 2006/0078924 A1 | 4/2006 | Finn et al. |
| 2006/0128646 A1 | 6/2006 | Christensen et al. |
| 2006/0134787 A1 | 6/2006 | Zamore et al. |
| 2006/0154888 A1 | 7/2006 | Rosenbohm et al. |
| 2006/0160123 A1 | 7/2006 | Quay |
| 2006/0166910 A1 | 7/2006 | Tuschl et al. |
| 2006/0212950 A1 | 9/2006 | Tuschl et al. |
| 2006/0234277 A1 | 10/2006 | Russell et al. |
| 2006/0241072 A1 | 10/2006 | Baker |
| 2006/0252721 A1 | 11/2006 | Westergaard et al. |
| 2007/0004665 A1 | 1/2007 | McSwiggen et al. |
| 2007/0004667 A1 | 1/2007 | McSwiggen et al. |
| 2007/0042983 A1 | 2/2007 | Haeberli et al. |
| 2007/0065840 A1 | 3/2007 | Naguibneva et al. |
| 2007/0111226 A1 | 5/2007 | Tan et al. |
| 2007/0111228 A1 | 5/2007 | Jayasena et al. |
| 2007/0117144 A1 | 5/2007 | Kauppinen et al. |
| 2007/0135372 A1 | 6/2007 | MacLachlan et al. |
| 2007/0167384 A1 | 7/2007 | Leake et al. |
| 2007/0173476 A1 | 7/2007 | Leake et al. |
| 2007/0191294 A1 | 8/2007 | Elmen et al. |
| 2007/0275465 A1 | 11/2007 | Woppmann et al. |
| 2008/0146788 A1 | 6/2008 | Bhat et al. |
| 2008/0248576 A1 | 10/2008 | Fire et al. |
| 2009/0176977 A1 | 7/2009 | Elmen et al. |

FOREIGN PATENT DOCUMENTS

| | | |
|---|---|---|
| EP | 1407044 | 9/2007 |
| EP | 1605978 | 9/2010 |
| GB | 2396616 | 9/2005 |
| WO | WO-99/14226 | 3/1999 |
| WO | WO-00/056746 | 9/2000 |
| WO | WO-01/025478 | 4/2001 |
| WO | WO-03/020739 | 3/2003 |
| WO | WO-03/074654 | 9/2003 |
| WO | WO-03/095467 | 11/2003 |
| WO | WO-2004/020575 | 3/2004 |
| WO | WO-2004/035819 | 4/2004 |
| WO | WO-2004/083430 | 9/2004 |
| WO | WO-2005/073378 | 8/2005 |
| WO | WO-2005/097992 | 10/2005 |
| WO | WO-2005/120230 | 12/2005 |
| WO | WO-2009/078685 | 6/2009 |

OTHER PUBLICATIONS

Braasch, Dwaine A. et al., "Antisense inhibition of gene expression in cells by oligonucleotides incorporating locked nucleic acids: effect of mRNA target sequence and chimera design", *Nucleic Acids Research* vol. 30, No. 23 2002, 5160-5167.

Chen, Caifu et al., "Real-time quantification of microRNAs by stem—loop RT—PCR", *Nucleic Acids Research* vol. 33, No. 20 2005, 1-9.

Chiu, Ya-Lin et al., "siRNA function in RNAi: A chemical modification analysis", *RNA* 9 2003, 1034-1048.

Chu, Chia-Ying et al., "Potent RNAi by short RNA triggers", *RNA* 14 2008, 1-6.

Collingwood, Michael A., "Chemical Modification Patterns Compatible with High Potency Dicer-Substrate Small Interfering RNAs", *Oligonucleotides* 18 2008, 187-200.

Dowler, Thomas et al., "Improvements in siRNA properties mediated by 2'-deoxy-2'-fluoro-β-D-arabinonucleic acid (FANA)", *Nucleic Acids Research* vol. 34, No. 6 2006, 1669-1675.

Elmen, Joacim et al., "Locked nucleic acid (LNA) mediated improvements in siRNA stability and functionality", *Nucleic Acids Research* vol. 33, No. 1 2005, 439-447.

Engels, BM et al., "Principles and effects of microRNA-mediated post-transcriptional gene regulation", *Oncogene* 25 2006, 6163-6169.

Hohjoh, Hirohiko, "Enhancement of RNAi activity by improved siRNA duplexes", *FEBS Letters* 557 2004, 193-198.

Ittig, Damian et al., "Nuclear antisense effects in cyclophilin a pre-mRNA splicing by oligonucleotides: a comparison of tricyclo-DNA with LNA", *Nucleic Acids Research* vol. 32, No. 1 2004, 346-353.

Jackson, Aimee L. et al., "Expression profiling reveals off-target gene regulation by RNAi", *Nature Biotechnology* vol. 21, No. 6 2003, 635-637 and data page.

Jackson, Aimee L. et al., "Position-specific chemical modification of siRNAs reduces "off-target" transcript silencing", *RNA* 12, Published by Cold Spring Harbor Laboratory Press. 2006, 1197-1205.

Jackson, Aimee L. et al., "Widespread siRNA "off-target" transcript silencing mediated by seed region sequence complementarity", *RNA* 12, Cold Spring Harbor Laboratory Press. 2006, 1179-1187.

Jiang, Ming et al., "A bi-functional siRNA construct induces RNA interference and also primes PCR amplification for its own quantification", *Nucleic Acids Re* vol. 33, No. 18 2005, 1-7.

Layzer, Juliana M. et al., "In vivo activity of nuclease-resistant siRNAs", *RNA* 10 2004, 766-771.

Leuschner, Philipp J. et al., "Cleavage of the siRNA passenger strand during RISC assembly in human cells", *EMBO reports* vol. 7, No. 3 2006, 314-320 and supplemental information pp. 1-11.

Maderia, Melissa M. et al., "Biophysical studies of DNA modified with conformationally constrained nucleotides: comparison of 20-exo (north) and 30-exo (south) 'locked' templates", *Nucleic Acids Research* vol. 35, No. 6 2007, 1978-1991.

Maier, Martin A. et al., "Synthesis and characterization of oligonucleotides containing conformationally constrained bicyclo[3.1.0]hexane pseudosugar analogs", *Nucleic Acids Research* vol. 32, No. 12 2004, 3642-3650.

Mook, Olaf R. et al., "Evaluation of locked nucleic acid—modified small interfering RNA in vitro and in vivo", *Mol Cancer Ther* 6 (3) 2007, 833-843.

Overhoff, Marita et al., "Quantitative detection of siRNA and single-stranded oligonucleotides: relationship between uptake and biological activity of siRNA", *Nucleic Acids Research* vol. 32, No. 21 2004, 1-5.

Parker, James S. et al., "Argonaute: a scaffold for the function of short regulatory RNAs", *Trends in Biochemical Sciences* vol. 31 No. 11 2006, 622-630.

PCT/US2008/076675 International Search Report and Written Opinion Mar. 11, 2009.

Puri, Nitin et al., "LNA® incorporated siRNAs exhibit lower off-target effects compared to 2'OMethoxy in Cell Phenotypic Assays and Microarray Analysis", *Nucleic Acids Symposium Series* No. 52 2008, 25-26.

Renneberg, Dorte et al., "Watson-Crick Base-Pairing Properties of Tricyclo-DNA", *J. Am. Chem. Soc.* vol. 124, No. 21 2002, 5993-6002.

Reynolds, Angela et al., "Rational siRNA design for RNA interference", *Nature Biotechnology* vol. 22, No. 3 2004, 326-330.

Sabatino, David et al., "Oxepane Nucleic Acids: Synthesis, Characterization, and Properties of Oligonucleotides Bearing a Seven-Membered Carbohydrate Ring", *J. Am. Chem. Soc.* 129 2007, 8259-8270.

Sano, Masayuki et al., "Effect of asymmetric terminal structures of short RNA duplexes on the RNA interference activity and strand selection", *Nucleic Acids.Research* 2008, 1-10.

Santana, Evelyn et al., "Different Frequency of Gene Targeting Events by the RNA-DNA Oligonucleotide Amoung Epithelial Cells", *The Journal of Investigative Dermatology* vol. 111, No. 6 1998, 1172-1177.

Srivastava, Puneet et al., "Five- and Six-Membered Conformationally Locked 2',4'-Carbocyclic ribo-Thymidines: Synthesis, Structure, and Biochemical Studies", *J. Am. Chem. Soc.* 129 2007, 8362-8379.

Sun, Xiangao et al., "Asymmetric RNA duplexes mediate RNA interference in mammalian cells", *Nature Biotechnology* vol. 26, No. 12 2008, 1379-1382.

Vermeulen, Annaleen, "The contributions of dsRNA structure to Dicer specificity and efficiency", *RNA* vol. 11, Published by Cold Spring Harbor Laboratory Press 2005, 674-682.

EP 12189270.7; Extended European Search Report mailed Dec. 19, 2012.

```
                           1  2  3  4  5  6  7  8  9 10 11 12 13 14 15 16 17 18 19 20 21
Passenger (Sense) Strand   5'-NNNNNNNNNNNNNNNNNNNnn-3'
Guide (Antisense) Strand   3'-nnNNNNNNNNNNNNNNNNNNN-5'
                           21 20 19 18 17 16 15 14 13 12 11 10 9 8 7 6 5 4 3 2 1
```
Format A (Unmodified)

```
                           1  2  3  4  5  6  7  8  9 10 11 12 13 14 15 16 17 18 19 20 21
Passenger (Sense) Strand   5'-mNNNNNNNNNNNNNNNNNNNmm-3'
Guide (Antisense) Strand   3'-NNNNNNNNNNNNNNNNNNNNN-5'
                           21 20 19 18 17 16 15 14 13 12 11 10 9 8 7 6 5 4 3 2 1
```
Format E

```
                           1  2  3  4  5  6  7  8  9 10 11 12 13 14 15 16 17 18 19 20 21
Passenger (Sense) Strand   5'-mNNNNNNNNNNNNNNNNNNNmm-3'
Guide (Antisense) Strand   3'-mmNNNNNNNNNNNNNNNNNNN-5'
                           21 20 19 18 17 16 15 14 13 12 11 10 9 8 7 6 5 4 3 2 1
```
Format F

```
                           1  2  3  4  5  6  7  8  9 10 11 12 13 14 15 16 17 18 19 20 21
Passenger (Sense) Strand   5'-mmNNNNNNNNNNNmmNNNNNnn-3'
Guide (Antisense) Strand   3'-nmmNNNNNNNNNmmNNNNNNNN-5'
                           21 20 19 18 17 16 15 14 13 12 11 10 9 8 7 6 5 4 3 2 1
```
Format G

```
                           1  2  3  4  5  6  7  8  9 10 11 12 13 14 15 16 17 18 19 20 21
Passenger (Sense) Strand   5'-mmNNNNNNNNNNNmmNNNNNnn-3'
Guide (Antisense) Strand   3'-nnNNNNNNNNNNNNNNNNNNN-5'
                           21 20 19 18 17 16 15 14 13 12 11 10 9 8 7 6 5 4 3 2 1
```
Format H

```
                           1  2  3  4  5  6  7  8  9 10 11 12 13 14 15 16 17 18 19 20 21
Passenger (Sense) Strand   5'-mmNNNNNNNmNNNmNNNNNnn-3'
Guide (Antisense) Strand   3'-nmmNNNNNNmmNNNNNNNNNN-5'
                           21 20 19 18 17 16 15 14 13 12 11 10 9 8 7 6 5 4 3 2 1
```
Format J

```
                           1  2  3  4  5  6  7  8  9 10 11 12 13 14 15 16 17 18 19 20 21
Passenger (Sense) Strand   5'-mmNNNNNNNmNNNmNNNNNnn-3'
Guide (Antisense) Strand   3'-nnNNNNNNNNNNNNNNNNNNN-5'
                           21 20 19 18 17 16 15 14 13 12 11 10 9 8 7 6 5 4 3 2 1
```
Format K

```
                           1  2  3  4  5  6  7  8  9 10 11 12 13 14 15 16 17 18 19 20 21
Passenger (Sense) Strand   5'-mmNNNNNNNNNNNNNNNNNNNnn-3'
Guide (Antisense) Strand   3'-nnNNNNNNNNNNNNNNNNNNmN-P-5'
                           21 20 19 18 17 16 15 14 13 12 11 10 9 8 7 6 5 4 3 2 1
```
Format O

FIG. 1A

Passenger (Sense) Strand     1 2 3 4 5 6 7 8 9 10 11 12 13 14 15 16 17 18 19 20 21
5'-*mm*NNNNNNNNNNNNNNNNNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format M

Passenger (Sense) Strand     1 2 3 4 5 6 7 8 9 10 11 12 13 14 15 16 17 18 19 20 21
5'-*mm*NNNNNNNNNNN*mm*NNNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format H

Passenger (Sense) Strand     1 2 3 4 5 6 7 8 9 10 11 12 13 14 15 16 17 18 19 20 21
5'-*mm*NNNNNNNNNN*mm*NNNNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format H (-1)

Passenger (Sense) Strand     1 2 3 4 5 6 7 8 9 10 11 12 13 14 15 16 17 18 19 20 21
5'-*mm*NNNNNNNNN*mm*NNNNNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format H (-2)

Passenger (Sense) Strand     1 2 3 4 5 6 7 8 9 10 11 12 13 14 15 16 17 18 19 20 21
5'-*mm*NNNNNNNNNNNN*mm*NNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format H (+1)

Passenger (Sense) Strand     1 2 3 4 5 6 7 8 9 10 11 12 13 14 15 16 17 18 19 20 21
5'-NNNNNNNNNNNN*mm*NNNNN*nn*-3'
Guide (Antisense) Strand     3'-*nn*NNNNNNNNNNNNNNNNNNNNN-5'
21 20 19 18 17 16 15 14 13 12 11 10 9 8 7 6 5 4 3 2 1

Format Q

FIG. 1B

```
                                    1  2  3  4  5  6  7  8  9 10 11 12 13 14 15 16 17 18 19 20 21
Passenger (Sense) Strand         5'-mmNNNNNNNNNNNNNNNNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format M

```
                                    1  2  3  4  5  6  7  8  9 10 11 12 13 14 15 16 17 18 19 20 21
Passenger (Sense) Strand         5'-mmNNNNNNNNNNNmmNNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format H

```
                                    1  2  3  4  5  6  7  8  9 10 11 12 13 14 15 16 17 18 19 20 21
Passenger (Sense) Strand         5'-mmNNNNNNNNNmNmNNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format V

```
                                    1  2  3  4  5  6  7  8  9 10 11 12 13 14 15 16 17 18 19 20 21
Passenger (Sense) Strand         5'-mmNNNNNNNNmNmNNNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format V (-1)

```
                                    1  2  3  4  5  6  7  8  9 10 11 12 13 14 15 16 17 18 19 20 21
Passenger (Sense) Strand         5'-mmNNNNNNNmNmNNNNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format V (-2)

```
                                    1  2  3  4  5  6  7  8  9 10 11 12 13 14 15 16 17 18 19 20 21
Passenger (Sense) Strand         5'-mmNNNNNNNNNNmNmNNNNnn-3'
Guide (Antisense) Strand         3'-nnNNNNNNNNNNNNNNNNNNNNN-5'
                                    21 20 19 18 17 16 15 14 13 12 11 10  9  8  7  6  5  4  3  2  1
```

Format V (+1)

FIG. 1C

```
                                1  2  3  4 5  6 7 8  9 10 11 12 13 14 15 16 17 18 19 20 21
Passenger (Sense) Strand        5'-NmmNNNNNNNNNmmNNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format W
```

```
                                1  2  3  4 5  6 7 8  9 10 11 12 13 14 15 16 17 18 19 20 21
Passenger (Sense) Strand        5'-NmmNNNNNNNNNNmmNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format W+1
```

```
                                1  2  3  4 5  6 7 8  9 10 11 12 13 14 15 16 17 18 19 20 21
Passenger (Sense) Strand        5'-NmmNNNNNNNNmmNNNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format W-1
```

```
                                1  2  3  4 5  6 7 8  9 10 11 12 13 14 15 16 17 18 19 20 21
Passenger (Sense) Strand        5'-mNmNNNNNNNNNmmNNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format Y
```

```
                                1  2  3  4 5  6 7 8  9 10 11 12 13 14 15 16 17 18 19 20 21
Passenger (Sense) Strand        5'-mNmNNNNNNNNmmNNNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format Y-1
```

```
                                1  2  3  4 5  6 7 8  9 10 11 12 13 14 15 16 17 18 19 20 21
Passenger (Sense) Strand        5'-mNmNNNNNNNNNNmmNNNNnn-3'
Guide (Antisense) Strand        3'-nnNNNNNNNNNNNNNNNNNNNNN-5'
                                  21 20 19 18 17 16 15 14 13 12 11 10  9  8  7  6  5  4  3  2  1
                                Format Y+1
```

FIG. 1D

Passenger (Sense) Strand    5'-*mm*NNNNNNNNNNN*m*NNNNNN*nn*-3'
Guide (Antisense) Strand    3'-*nn*NNNNNNNNNNNNNNNNNNN-5' positions passenger: 1 2 3 4 5 6 7 8 9 10 11 12 13 14 15 16 17 18 19 20 21
positions guide: 21 20 19 18 17 16 15 14 13 12 11 10 9 8 7 6 5 4 3 2 1

Format JB1

Passenger (Sense) Strand    5'-*m*NNNNNNNNNNNN*mm*NNNNN*nn*-3'
Guide (Antisense) Strand    3'-*nn*NNNNNNNNNNNNNNNNNNN-5'

Format JB2

Passenger (Sense) Strand    5'-*mmmm*NNNNNNNN*mm*NNNNNN*nn*-3'
Guide (Antisense) Strand    3'-*nn*NNNNNNNNNNNNNNNNNNN-5'

Format JB3

Passenger (Sense) Strand    5'-*mmm*NNNNNNNNNN*m*N*m*NNNNN*nn*-3'
Guide (Antisense) Strand    3'-*nn*NNNNNNNNNNNNNNNNNNN-5'

Format JB4

Passenger (Sense) Strand    5'-*mmmm*NNNNNNNNN*mm*NNNNN*nn*-3'
Guide (Antisense) Strand    3'-*nn*NNNNNNNNNNNNNNNNNNN-5'

Format JB5

FIG. 1E

Passenger (Sense) Strand  5'-*mm*NNNNNNNNNN*mm*NNNNN*nn*-3'
1 2 3 4 5 6 7 8 9 10 11 12 13 14 15 16 17 18 19 20 21

Guide (Antisense) Strand  3'-*mm*NNNNNNNNNNNNNNNNNNN-5'
21 20 19 18 17 16 15 14 13 12 11 10 9 8 7 6 5 4 3 2 1

Format DH21

Passenger (Sense) Strand  5'-*mm*NNNNNNNNNN*mm*NNNNN*nn*-3'
1 2 3 4 5 6 7 8 9 10 11 12 13 14 15 16 17 18 19 20 21

Guide (Antisense) Strand  3'-*mmm*NNNNNNNNNNNNNNNNNN-5'
21 20 19 18 17 16 15 14 13 12 11 10 9 8 7 6 5 4 3 2 1

Format DH20

Passenger (Sense) Strand  5'-*mm*NNNNNNNNNN*mm*NNNNN*mm*-3'
1 2 3 4 5 6 7 8 9 10 11 12 13 14 15 16 17 18 19 20 21

Guide (Antisense) Strand  3'- *nn*NNNNNNNNNNNNNNNNNNN-5'
21 20 19 18 17 16 15 14 13 12 11 10 9 8 7 6 5 4 3 2 1

Format DH3

Passenger (Sense) Strand  5'-*mm*NNNNNNNNNN*mm*NNNN*mmn*-3'
1 2 3 4 5 6 7 8 9 10 11 12 13 14 15 16 17 18 19 20 21

Guide (Antisense) Strand  3'- *nn*NNNNNNNNNNNNNNNNNNN-5'
21 20 19 18 17 16 15 14 13 12 11 10 9 8 7 6 5 4 3 2 1

Format DH30

Passenger (Sense) Strand  5'-*mm*NNNNNNNNNN*mm*NNNNN*mn*-3'
1 2 3 4 5 6 7 8 9 10 11 12 13 14 15 16 17 18 19 20 21

Guide (Antisense) Strand  3'- *mn*NNNNNNNNNNNNNNNNNNN-5'
21 20 19 18 17 16 15 14 13 12 11 10 9 8 7 6 5 4 3 2 1

Format DH35

Passenger (Sense) Strand  5'-*m*NNNNNNNNNNN*mm*NNNNN*nm*-3'
1 2 3 4 5 6 7 8 9 10 11 12 13 14 15 16 17 18 19 20 21

Guide (Antisense) Strand  3'- *mn*NNNNNNNNNNNNNNNNNNN-5'
21 20 19 18 17 16 15 14 13 12 11 10 9 8 7 6 5 4 3 2 1

Format DH6

Passenger (Sense) Strand  5'-*mm*NNNNNNNNNN*mm*NNNNN*mm*-3'
1 2 3 4 5 6 7 8 9 10 11 12 13 14 15 16 17 18 19 20 21

Guide (Antisense) Strand  3'- *mn*NNNNNNNNNNNNNNNNNNN-5'
21 20 19 18 17 16 15 14 13 12 11 10 9 8 7 6 5 4 3 2 1

Format DH34

Passenger (Sense) Strand  5'-*mm*NNNNNNNNNN*mm*NNNNN*mm*-3'
1 2 3 4 5 6 7 8 9 10 11 12 13 14 15 16 17 18 19 20 21

Guide (Antisense) Strand  3'-*mm*NNNNNNNNNNNNNNNNNNN-5'
21 20 19 18 17 16 15 14 13 12 11 10 9 8 7 6 5 4 3 2 1

Format DH2

FIG. 1F

|                           | 1 2 3 4 5 6 7 8 9 10 11 12 13 14 15 16 17 18 19 20 21 |
|---------------------------|-------|

Passenger (Sense) Strand     5'-*m*NNNNNNNNNNNNNNNNNNN*mm*-3'
Guide (Antisense) Strand     3'-*mm*NNNNNNNNNNNNNNNNNNNNN-5'
               21 20 19 18 17 16 15 14 13 12 11 10 9 8 7 6 5 4 3 2 1

Format F

Passenger (Sense) Strand     5'-*mm*NNNNNNNNN*mm*NNNN*mmn*-3'
Guide (Antisense) Strand     3'-*mmm*NNNNNNNNNNNNNNNNNN-5'
               21 20 19 18 17 16 15 14 13 12 11 10 9 8 7 6 5 4 3 2 1

Format DH19

Passenger (Sense) Strand     5'-*mm*NNNNNNNNN*mm*NNNN*mmn*-3'
Guide (Antisense) Strand     3'-*nmm*NNNNNNNNNNNNNNNNNN-5'
               21 20 19 18 17 16 15 14 13 12 11 10 9 8 7 6 5 4 3 2 1

Format DH4

Passenger (Sense) Strand     5'-*mm*NNNNNNNNNN*mm*NNNN*mmn*-3'
Guide (Antisense) Strand     3'-*mm*NNNNNNNNNNNNNNNNNNN-5'
               21 20 19 18 17 16 15 14 13 12 11 10 9 8 7 6 5 4 3 2 1

Format DH31

Passenger (Sense) Strand     5'-*mm*NNNN*m*NNNNN*mm*NNNN*mmn*-3'
Guide (Antisense) Strand     3'-*mm*NNNNNNNNNNNNNNNNNNN-5'
               21 20 19 18 17 16 15 14 13 12 11 10 9 8 7 6 5 4 3 2 1

Format DH27

Passenger (Sense) Strand     5'-*mm*NNN*m*NN*m*NNN*mm*NNNN*mmn*-3'
Guide (Antisense) Strand     3'-*mm*NNNNNNNNNNNNNNNNNNN-5'
               21 20 19 18 17 16 15 14 13 12 11 10 9 8 7 6 5 4 3 2 1

Format DH25

FIG. 1G

Passenger (Sense) Strand  
Guide (Antisense) Strand

```
                    1 2 3 4 5 6 7 8 9 10 11 12 13 14 15 16 17 18 19 20 21
5'-mNNNNNNNNNNNNNNNNNNNmm-3'
3'-mmNNNNNNNNNNNNNNNNNNNNN-5'
    21 20 19 18 17 16 15 14 13 12 11 10 9 8 7 6 5 4 3 2 1
```

Format F

Passenger (Sense) Strand  
Guide (Antisense) Strand

```
                    1 2 3 4 5 6 7 8 9 10 11 12 13 14 15 16 17 18 19 20 21
5'-mmNNNNNNNNNNmmNNNNNmm-3'
3'-mmNNNNNNNNNNNNNNNNNNNNN-5'
    21 20 19 18 17 16 15 14 13 12 11 10 9 8 7 6 5 4 3 2 1
```

Format DH2

Passenger (Sense) Strand  
Guide (Antisense) Strand

```
                    1 2 3 4 5 6 7 8 9 10 11 12 13 14 15 16 17 18 19 20 21
5'-mmNNNNNNNNNNNmmNNNNmmm-3'
3'-mmNNNNNNNNNNNNNNNNNNNNN-5'
    21 20 19 18 17 16 15 14 13 12 11 10 9 8 7 6 5 4 3 2 1
```

Format DH47

Passenger (Sense) Strand  
Guide (Antisense) Strand

```
                    1 2 3 4 5 6 7 8 9 10 11 12 13 14 15 16 17 18 19 20 21
5'-mmNNNNNNNNNNNmmNNNmNmm-3'
3'-mmNNNNNNNNNNNNNNNNNNNNN-5'
    21 20 19 18 17 16 15 14 13 12 11 10 9 8 7 6 5 4 3 2 1
```

Format DH29

Passenger (Sense) Strand  
Guide (Antisense) Strand

```
                    1 2 3 4 5 6 7 8 9 10 11 12 13 14 15 16 17 18 19 20 21
5'-mmNNNNNNNNNNNmmNNNmNmm-3'
3'- nnNNNNNNNNNNNNNNNNNNNN-5'
    21 20 19 18 17 16 15 14 13 12 11 10 9 8 7 6 5 4 3 2 1
```

Format DH28

Passenger (Sense) Strand  
Guide (Antisense) Strand

```
                    1 2 3 4 5 6 7 8 9 10 11 12 13 14 15 16 17 18 19 20 21
5'-mmNNNNNNNNNNNmmNNNmNmm-3'
3'-mmmNNNNNNNNNNNNNNNNNNNN-5'
    21 20 19 18 17 16 15 14 13 12 11 10 9 8 7 6 5 4 3 2 1
```

Format DH18

FIG. 1H

```
                          1 2 3 4 5  6 7 8  9 10 11  12 13 14 15 16 17 18  19 20 21
Passenger (Sense) Strand  5'-mNNNNNNNNNNNNNNNNNNNmm-3'
Guide (Antisense) Strand  3'-mmNNNNNNNNNNNNNNNNNNNNN-5'
                             21 20 19 18 17 16 15 14 13 12 11 10 9 8 7 6 5 4 3 2 1
```
Format F

```
                          1 2 3 4 5  6 7 8  9 10 11  12 13 14 15 16 17 18 19 20 21
Passenger (Sense) Strand  5'-mmNNNNNNNNNNNNNNNNNNNmm-3'
Guide (Antisense) Strand  3'-mmNNNNNNNNNNNNNNNNNNNNN-5'
                             21 20 19 18 17 16 15 14 13 12 11 10 9 8 7 6 5 4 3 2 1
```
Format DH36

```
                          1 2 3 4 5  6 7 8  9 10 11  12 13 14 15 16 17 18 19 20 21
Passenger (Sense) Strand  5'-mmNNNNNNNNNNNmmNNNNNmm-3'
Guide (Antisense) Strand  3'-mmNNNNNNNNNNNNNNNNNNNNN-5'
                             21 20 19 18 17 16 15 14 13 12 11 10 9 8 7 6 5 4 3 2 1
```
Format DH2

```
                          1 2 3 4 5  6 7 8  9 10 11  12 13 14 15 16 17 18 19 20 21
Passenger (Sense) Strand  5'-mmNNNNNNNNNNNmmNNNNNmn-3'
Guide (Antisense) Strand  3'-mmNNNNNNNNNNNNNNNNNNNNN-5'
                             21 20 19 18 17 16 15 14 13 12 11 10 9 8 7 6 5 4 3 2 1
```
Format DH9

```
                          1 2 3 4 5  6 7 8  9 10 11  12 13 14 15 16 17 18 19 20 21
Passenger (Sense) Strand  5'-mmNNNNNNNNNNNmmNNNNNnm-3'
Guide (Antisense) Strand  3'-mmNNNNNNNNNNNNNNNNNNNNN-5'
                             21 20 19 18 17 16 15 14 13 12 11 10 9 8 7 6 5 4 3 2 1
```
Format DH46

```
                          1 2 3 4 5  6 7 8  9 10 11  12 13 14 15 16 17 18 19 20 21
Passenger (Sense) Strand  5'-mmNNNNNNNNNNNmmNNNNNmm-3'
Guide (Antisense) Strand  3'-nmNNNNNNNNNNNNNNNNNNNNN-5'
                             21 20 19 18 17 16 15 14 13 12 11 10 9 8 7 6 5 4 3 2 1
```
Format DH33

```
                          1 2 3 4 5  6 7 8  9 10 11  12 13 14 15 16 17 18 19 20 21
Passenger (Sense) Strand  5'-mmNNNNNNNNNNNmmNNNNNmn-3'
Guide (Antisense) Strand  3'-nmNNNNNNNNNNNNNNNNNNNNN-5'
                             21 20 19 18 17 16 15 14 13 12 11 10 9 8 7 6 5 4 3 2 1
```
Format DH10

FIG. 1I

|  | 1 2 3 4 5 6 7 8 9 10 11 12 13 14 15 16 17 18 19 20 21 |
|---|---|
| Passenger (Sense) Strand | 5'-*m*NNNNNNNNNNNNNNNNNNN*mm*-3' |
| Guide (Antisense) Strand | 3'-*mm*NNNNNNNNNNNNNNNNNNNN-5' |
|  | 21 20 19 18 17 16 15 14 13 12 11 10 9 8 7 6 5 4 3 2 1 |

Format F

|  | 1 2 3 4 5 6 7 8 9 10 11 12 13 14 15 16 17 18 19 20 21 |
|---|---|
| Passenger (Sense) Strand | 5'-*mm*NNNNNNNNNNNNNNNNNN*mm*-3' |
| Guide (Antisense) Strand | 3'-*mm*NNNNNNNNNNNNNNNNNNN*m*N-5' |
|  | 21 20 19 18 17 16 15 14 13 12 11 10 9 8 7 6 5 4 3 2 1 |

Format DH7

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*nn*-3' |
| Guide (Antisense) Strand | 3'-*mm*NNNNNNNNNNNNNNNNNN*m*N-5' |
|  | 21 20 19 18 17 16 15 14 13 12 11 10 9 8 7 6 5 4 3 2 1 |

Format DH23

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*mm*-3' |
| Guide (Antisense) Strand | 3'-*mm*NNNNNNNNNNNNNNNNNN*m*N-5' |
|  | 21 20 19 18 17 16 15 14 13 12 11 10 9 8 7 6 5 4 3 2 1 |

Format DH1

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*mm*-3' |
| Guide (Antisense) Strand | 3'- *nm*NNNNNNNNNNNNNNNNNN*m*N-5' |
|  | 21 20 19 18 17 16 15 14 13 12 11 10 9 8 7 6 5 4 3 2 1 |

Format DH48

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*mm*-3' |
| Guide (Antisense) Strand | 3'- *mn*NNNNNNNNNNNNNNNNNN*m*N-5' |
|  | 21 20 19 18 17 16 15 14 13 12 11 10 9 8 7 6 5 4 3 2 1 |

Format DH49

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*mn*-3' |
| Guide (Antisense) Strand | 3'-*mm*NNNNNNNNNNNNNNNNNN*m*N-5' |
|  | 21 20 19 18 17 16 15 14 13 12 11 10 9 8 7 6 5 4 3 2 1 |

Format DH44

|  | 1 2 3 4 5 6 7 8 9 10 11 12 13 14 15 16 17 18 19 20 21 |
|---|---|
| Passenger (Sense) Strand | 5'-*mm*NNNNNNNNNNN*mm*NNNNN*nm*-3' |
| Guide (Antisense) Strand | 3'-*mm*NNNNNNNNNNNNNNNNNN*m*N-5' |
|  | 21 20 19 18 17 16 15 14 13 12 11 10 9 8 7 6 5 4 3 2 1 |

Format DH45

FIG. 1J

Passenger (Sense) Strand    5'-*m*NNNNNNNNNNNNNNNNNNN*mm*-3'
                                    1 2 3 4 5 6 7 8 9 10 11 12 13 14 15 16 17 18 19 20 21

Guide (Antisense) Strand    3'-*mm*NNNNNNNNNNNNNNNNNNN-5'
                                    21 20 19 18 17 16 15 14 13 12 11 10 9 8 7 6 5 4 3 2 1

Format F

Passenger (Sense) Strand    5'-*mm*NNNNNNNNNN*mm*NNNNN*mm*-3'
Guide (Antisense) Strand    3'-*mm*NNNNNNNNNNNNNNNNNN*m*-5'

Format DH38

Passenger (Sense) Strand    5'-*mm*NNNNNNNNNN*mm*NNNNN*mm*-3'
Guide (Antisense) Strand    3'-*mm*NNNNNNNNNNNNNNNNN*m*N-5'

Format DH1

Passenger (Sense) Strand    5'-*mm*NNNNNNNNNN*mm*NNNNN*mm*-3'
Guide (Antisense) Strand    3'-*mm*NNNNNNNNNNNNNNNN*m*NN-5'

Format DH39

Passenger (Sense) Strand    5'-*mm*NNNNNNNNNN*mm*NNNNN*mm*-3'
Guide (Antisense) Strand    3'-*mm*NNNNNNNNNNNNNNN*m*NNN-5'

Format DH40

Passenger (Sense) Strand    5'-*mm*NNNNNNNNNN*mm*NNNNN*mm*-3'
Guide (Antisense) Strand    3'-*mm*NNNNNNNNNNNNNN*m*NNNN-5'

Format DH41

Passenger (Sense) Strand    5'-*mm*NNNNNNNNNN*mm*NNNNN*mm*-3'
Guide (Antisense) Strand    3'-*mm*NNNNNNNNNNNNN*m*NNNNN-5'

Format DH42

Passenger (Sense) Strand    5'-*mm*NNNNNNNNNN*mm*NNNNN*mm*-3'
Guide (Antisense) Strand    3'-*mm*NNNNNNNNNNNN*m*NNNNNN-5'

Format DH43

FIG. 1K

US 8,524,681 B2

SIRNA SEQUENCE-INDEPENDENT MODIFICATION FORMATS FOR REDUCING OFF-TARGET PHENOTYPIC EFFECTS IN RNAI, AND STABILIZED FORMS THEREOF

This application is a continuation application of, and claims priority to, International Patent Application PCT/US2008/076675, having an international filing date of Sep. 17, 2008, which application claims the benefit of U.S. provisional patent application 60/973,548, filed Sep. 19, 2007. Each application is incorporated by reference herein in its entirety.

FIELD

The present teachings generally relate to compositions, methods, and kits for reducing sequence-independent off-target phenotypic effects in RNA interference.

INTRODUCTION

Short interfering RNA (siRNA) potently induces cleavage of complementary mRNA rendering the mRNA nonfunctional with consequent loss of functional protein in a cell. The mechanism by which these molecules work has been partially characterized. Briefly, one of the two RNA strands of the siRNA is incorporated into an enzyme complex termed RISC, which complex is then able to bind to and cleave a mRNA containing a complementary sequence thereby eliminating the mature mRNA from translation into protein. Each of the two strands of a siRNA can be incorporated into the RISC complex. However, the strand that has the weaker basepair at its 5'-end is preferred for incorporation. Therefore, any siRNA will lead to the production of a mixture of activated RISC complexes that can cleave both the intended target RNA as well as non-targeted RNA. In biological applications, it is desirable that the vast majority, preferably all, of the activated RISC complexes contain the siRNA strand that is complementary to the desired target. The present teachings provide methods, compositions and kits for not only reducing mRNA cleavage by the non-desired siRNA strand but also for reducing off-target effects for interference of endogenous genes.

SUMMARY

Unexpectedly, increasing or maintaining strand bias, while necessary to maintain potency for endogenous RNA interference, is not sufficient for reducing off-target effects in cell biology assays. The ability to reduce or minimize off-target effects while maintaining potency was studied herein under conditions where the target mRNA was provided exogenously as well as where the target mRNA was an endogenous mRNA, under conditions where different types of modified nucleotides were introduced into siRNAs, and under conditions where different modification formats were introduced into siRNAs. Further, multiple siRNA modification formats were studied for each of a number of target RNAs. Therefore, modified nucleotides and modification formats that reduce or minimize off-target events and that maintain potency of a highly potent siRNA as observed at the phenotype and cell biology level are applicable to any siRNA sequence and are not dependent on the sequence of the bases of a siRNA. That is, the modification formats provided herein are sequence-independent modifications.

In some embodiments, a chemically synthesized passenger (sense) oligonucleotide is provided, the oligonucleotide having a length of 15 to 30 nucleotides and comprising one of sequence-independent modification format (1), sequence-independent modification format (2), and sequence-independent modification format (3) as follows:

(1) 5' $N_p$-m-m-$N_x$-m-m-$N_q$-$n_r$ 3', wherein p is 0 or 1; x is 7, 8, 9, 10, or 11; r is 0, 1, or 2; and q is an integer representing the length of the passenger strand minus (p+x+r+4);

(2) 5' $N_p$-m-m-$N_y$-m-m-$N_z$-m-m-$N_q$-$n_r$ 3', wherein p is 0 or 1; y is 7, 8, or 9 and z is 1; or y is 7 and z is 2 or 3; r is 0, 1, or 2; and q is an integer representing the length of the passenger strand minus (p+y+z+r+4);

(3) 5'm-$N_1$-m-$N_x$-m-m-$N_q$-$n_r$ 3', wherein x is 8, 9, or 10; r is 0, 1, or 2; and q is an integer representing the length of the passenger strand minus (x+r+5);

wherein each m is independently a bicyclo nucleotide or a tricyclo nucleotide; each n is independently a deoxynucleotide, modified nucleotide, or ribonucleotide; when m is a bicyclo nucleotide, each N is independently a nucleotide other than a bicyclo nucleotide, and when m is a tricyclo nucleotide, each N is independently a nucleotide other than a tricyclo nucleotide.

In some embodiments, a chemically synthesized short interfering RNA is provided that comprises the passenger (sense) oligonucleotide described above and a guide (antisense) oligonucleotide having 15 to 30 nucleotides, a region of continuous complementarity to the passenger (sense) oligonucleotide of at least 12 nucleotides; the guide strand further having complementarity to at least a portion of a target mRNA.

In some embodiments, a short interfering RNA is provided that comprises a passenger (sense) oligonucleotide having a length of 17 to 30 nucleotides and comprising one of sequence-independent modification format (4), format (5), and format (6) and a guide (antisense) oligonucleotide having 17 to 30 nucleotides, a region of continuous complementarity to the passenger (sense) oligonucleotide of at least 12 nucleotides; the guide strand further having complementarity to at least a portion of target mRNA, (4) 5' $m_p$-$N_x$-m-m-$N_q$-$n_r$ 3' wherein when p is 0, x is 12; when p is 1, x is 11; when p is 2, x is 10; when p is 3, x is 9, when p is 4, x is 8; r is 0, 1, or 2; and q is an integer representing the length of the passenger strand minus (p+x+r+2);

(5) 5' m-m-$N_x$-m-$N_q$-$n_r$ 3' wherein x is 11; r is 0, 1, or 2; and q is an integer representing the length of the passenger strand minus (x+r+3);

(6) 5' $m_p$-$N_y$-m-$N_z$m-$N_q$-$n_r$ 3', wherein p is 3; y is 9 and z is 1; r is 0, 1, or 2; and q is an integer representing the length of the passenger strand minus (p+y+z+r+2);

wherein each m is independently a bicyclonucleotide, a tricyclonucleotide, or a 2'-modified nucleotide; each n is independently a deoxynucleotide, modified nucleotide, or ribonucleotide and is an overhanging nucleotide; when m is a bicyclonucleotide, each N is independently a nucleotide other than a bicyclonucleotide, when m is a tricyclonucleotide, each N is independently a nucleotide other than a tricyclonucleotide, and when m is a 2'-modified nucleotide, each N is independently a nucleotide other than a 2'-modified nucleotide.

In an embodiment of the short interfering RNA, the passenger (sense) oligonucleotide has sequence independent modification format (4), p is 2, x is 10, r is 2, each n is an overhanging nucleotide, and each n is independently a modified nucleotide; the guide (antisense) oligonucleotide comprises two 3'-overhanging modified nucleotides; and each modified nucleotide is independently a bicyclonucleotide, a tricyclonucleotide, or a 2'-modified nucleotide. In one embodiment, at least one of the 3' antepenultimate and the 3' preantepenultimate positions of the passenger oligonucleotide is a modified nucleotide. The 3' antepenultimate position is the third from the last position, i.e., the position prior to the penultimate position, e.g., as for Format DH47 of FIG. 1H. The 3' preantepenultimate position is the fourth from the last position, i.e., the position prior to the antepenultimate position, e.g., as for Format DH29 of FIG. 1H. Such siRNAs are particularly stable to nucleases such as in the presence of serum or plasma, for example.

In some embodiments of the short interfering RNA, when the length is 17 nucleotides, at least one of positions 2 and 3 of the guide oligonucleotide is a modified nucleotide; when the length is 18 nucleotides, at least one of positions 2, 3 and 4 of the guide oligonucleotide is a modified nucleotide; when the length is 19 nucleotides, at least one of positions 2, 3, 4 and 5 of the guide oligonucleotide is a modified nucleotide; when the length is 20 nucleotides, at least one of positions 2, 3, 4, 5 and 6 of the guide oligonucleotide is a modified nucleotide; and when the length is 21-30 nucleotides, at least one of positions 2, 3, 4, 5, 6 and 7 of the guide oligonucleotide is a modified nucleotide. Formats DH1, and Formats DH39-DH43 of FIG. 1K provide examples of siRNA modification formats having a length of 21 nucleotides and having at least one of positions 2, 3, 4, 5, 6 and 7 of the guide oligonucleotide as a modified nucleotide. In some embodiments, only one of positions 2, 3, 4, 5, 6 and 7 (depending upon length as cited above) of the guide oligonucleotide is a modified nucleotide. Such siRNAs are also particularly stable to nucleases such as in the presence of serum, for example.

A method of reducing or minimizing off-target events for inhibition of expression of a target gene by RNA interference is provided that comprises contacting a cell containing the target gene with the chemically synthesized short interfering RNA described above wherein each m is independently a bicyclonucleotide or a tricyclonucleotide in an amount sufficient to reduce off-target events while maintaining potency. The phrase "while maintaining potency," is used herein in the context of use of a sufficient amount of siRNA to reduce off-target events while maintaining potency. In this context, the phrase refers to the tolerance for reducing knockdown activity of the siRNA while reducing off-target events and is dictated by whether the reduced knockdown activity elicits the gene associated phenotype. In general, "while maintaining potency" means that a reduction of knockdown to 80% of normal knockdown levels is acceptable. However, the tolerance for reduced knockdown of a specific gene can range from 50% to 95% of normal knockdown.

In further embodiments, a method of reducing or minimizing cleavage by a passenger strand in inhibition of expression of an exogenously provided target gene by RNA interference is provided, which method comprises contacting a cell containing the target gene with a chemically synthesized short interfering RNA in an amount sufficient to reduce or minimize cleavage by a passenger strand while maintaining potency of a guide strand, the passenger strand of the short interfering RNA comprising one of sequence-independent modification formats (1), (2), (3), (4), (5), or (6) wherein each m is independently a 2'-modified nucleotide; each n is independently a deoxynucleotide, modified nucleotide, or ribonucleotide; and each N is independently an unmodified nucleotide. The reduction in cleavage is in comparison to that of unmodified siRNA.

In some embodiments, the contacting is in vitro contacting of a cell culture containing the cell, or a tissue containing the cell with the chemically synthesized short interfering RNA. In further embodiments, the contacting is ex vivo contacting of a tissue containing the cell, a bodily fluid containing the cell, or an organ containing the cell with the chemically synthesized short interfering RNA. In yet other embodiments, the contacting is in vivo contacting of an organ or an animal containing the cell with the chemically synthesized short interfering RNA. In some embodiments, the contacting is in vivo intravascular administration of a short interfering RNA having modification formats that confer nuclease stability thereto to a subject in need thereof. As demonstrated by the data of Example 8, a greater amount of the stabilized short interfering RNA is present in vivo post administration when compared to an amount present in vivo of control short interfering RNA lacking modified nucleotides at the same post administration time point.

RNA interference assays provided by embodiments herein and carried out on exogenously provided genes demonstrate that a number of types of modified nucleotides in various modification formats provide for enhanced strand bias while maintaining potency. See data for Formats H, K, and O using bicyclo nucleotides of FIG. 4A and FIG. 4B and data for Formats H, K, and O using 2'-O-methyl nucleotides of FIG. 6A and FIG. 6B.

Unexpectedly, those modified nucleotides and modification formats differed in ability to reduce or minimize off-target events in RNA interference of endogenous genes. A microarray analysis was carried out to determine the number of differentially expressed genes which is a measure of off-target effects due to introduced siRNA. A differentially expressed gene was defined as a gene having at least a 2-fold change due to RNA interference with a p value of <0.001. LNA® nucleotide-modified Format H siRNA produced 38% to 68% fewer differentially expressed genes as compared to the number of genes differentially expressed due to unmodified Format A siRNA having the same siRNA sequence. By comparison, 2'-O-methyl modified Format H siRNA produced 0% to 22% fewer differentially expressed genes when compared to unmodified Format A siRNA. Therefore, the LNA® nucleotide-modified siRNA is more effective at reducing off-target effects than 2'-O-methyl-modified siRNA as determined by global gene profiling analysis. See FIG. 9A-FIG. 9C.

These unexpected findings were confirmed using cell biology studies as illustrated by Example 6. When a collection of results was analyzed for siRNA interference of endogenous genes, it was evident that the 2'-O-methyl modified nucleotides in various modification formats as shown in FIG. 11C did not remove the "off-target" phenotypes to a statistically significant degree as compared to the unmodified format. These results are in contrast to those of FIG. 10E, which demonstrates a statistically significant ability of siRNAs having Format H to remove off-target effects as evidenced by the lower apoptotic signal compared to the unmodified Format A.

In some embodiments, the chemically synthesized short interfering RNA is further associated with a cell-targeting ligand as further described below.

Compositions comprising the passenger oligonucleotide, the guide oligonucleotide, or the chemically synthesized short interfering RNA and a biologically acceptable carrier are contemplated as embodiments herein. Further, kits that comprise the passenger oligonucleotide, the guide oligonucleotide, or chemically synthesized short interfering RNA and a transfection agent, for example, are contemplated as embodiments herein. Short interfering RNAs having modification formats with modified nucleotides of embodiments provide improved efficacy thus saving time designing and testing siRNAs, improved specificity thus saving time and money spent on spurious results, improved potency thus allowing for less material to be used to achieve the effect desired. Improved efficacy and specificity also provide for use of fewer siRNAs per gene for individual gene and library screening studies.

In another embodiment, a method of reducing off-target effects on RNA interference comprises obtaining siRNA having a passenger sense strand including a region homologous to a target transcribed RNA and having a guide antisense strand complementary to the sense strand, the siRNA having modification Format H, Q, V−2, Y, Y+1, JB1, JB2, JB3, JB4 or JB5, and contacting said siRNA with a cell. A measure of reduction of off-target effects is made in comparison to the off-target effects due to an unmodified siRNA having the same sequence as the modification-formatted siRNA.

In a further embodiment, a method of increasing stability of siRNA in a nuclease-rich environment comprises obtaining siRNA having a passenger sense strand including a region homologous to a target transcribed RNA, having a guide antisense strand complementary to the sense strand, and having 3′-overhanging nucleotides, the siRNA having modification Format DH47, DH29, DH1, DH39, DH40, DH41, DH42, or DH43, and contacting said siRNA with the nuclease rich environment. A measure of increasing stability of siRNA is made in comparison to the stability of siRNA having Format F, having the same type of modified nucleotide and having the same sequence.

Further embodiments include siRNAs having modification formats as provided herein for use in RNA interference in in vitro, ex vivo, or in vivo applications for inhibition of expression of a target gene. When expression of a target gene is known to be associated with a disease, siRNAs herein are useful for screening for, diagnosis of or treatment of said disease.

An unexpected aspect of the siRNA performance studies described herein is the inability of reporter-based strandedness assays to predict performance of a modification-formatted siRNA at the cellular phenotypic level. Differences in performance at the phenotypic level were observed using microarray global gene profiling or cell-based assays as described below.

These and other features of the present teachings will become more apparent from the description herein.

DRAWINGS

The skilled artisan will understand that the drawings, described below, are for illustration purposes only. The drawings are not intended to limit the scope of the present teachings in any way.

FIG. 1A-FIG. 1K provide modification formats for siRNA studies. Numbers located above a nucleotide indicate the position of the nucleotide in the siRNA relative to the 5′ end of the format. m=a modified nucleotide, N=a nucleotide, or modified nucleotide having a modification other than the modification of m, n=nucleotide or modified nucleotide, P=a phosphate group.

Figure 2B:
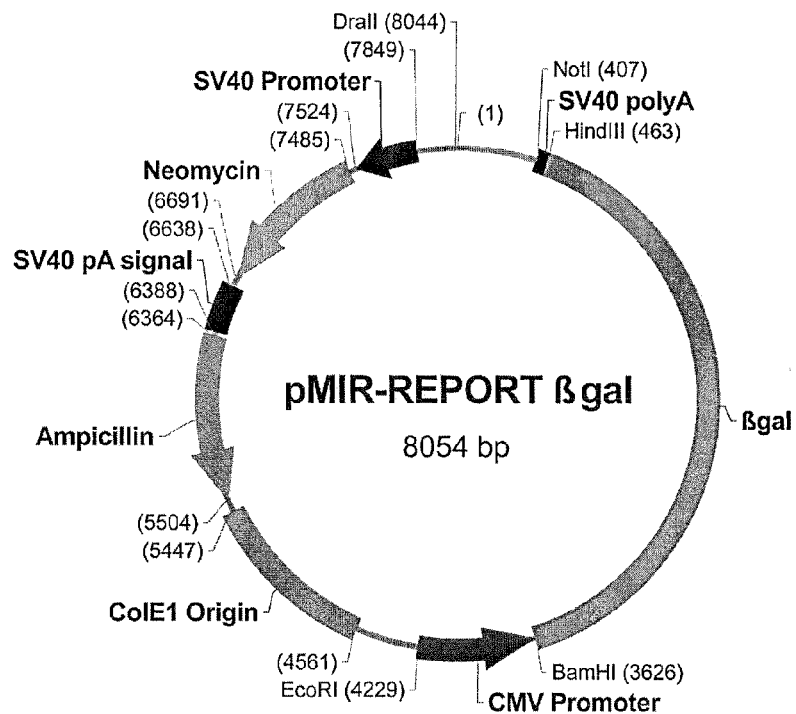

FIG. 2A-FIG. 2B provide schematic diagrams depicting expression reporter vectors used in various working examples. FIG. 2A shows a map of the pMIR-REPORT™ miRNA Expression Reporter Vector (Ambion/Applied Biosystems) containing the firefly luciferase reporter gene. The coding region of various genes of interest (GOI's) was inserted into the HindIII (nucleotide position 463) and SpeI (nucleotide position 525) restriction endonuclease sites within the multi-cloning site (MCS) located at the 3′ end of the luciferase gene. FIG. 2B shows a map of the pMIR-REPORT™ Beta-gal Control Vector (Ambion/Applied Biosystems) containing the β-galactosidase reporter gene. The control vector was co-transfected with the pMIR-REPORT™ miRNA Expression Reporter Vector carrying the GOI and used as a transfection normalization control.

Figure 3A:
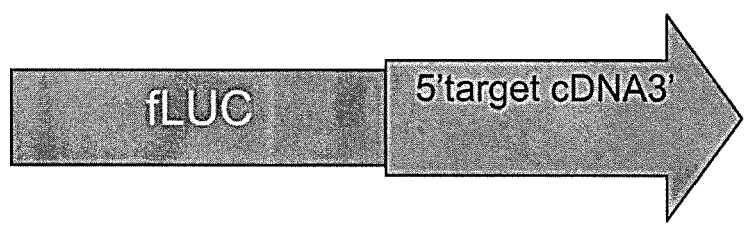
Figure 3B:
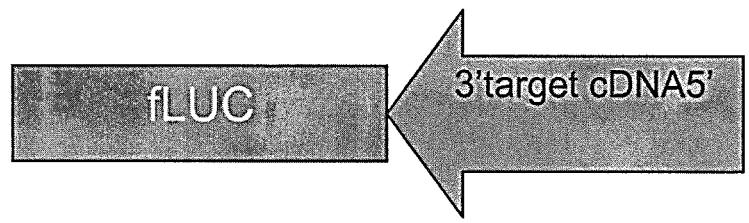

FIG. 3A-FIG. 3B provide schematic diagrams depicting the directional relationship between mRNA of a cloned GOI and the mRNA of the luciferase gene in the pMIR-REPORT™ miRNA expression vector. FIG. 3A provides the forward orientation, i.e., the 5′-end of the GOI mRNA is proximal to the 3′-end of the fLuc mRNA. FIG. 3B provides the reverse orientation, i.e., the 5′-end of the GOI mRNA is distal to the 3′-end of the fLuc mRNA.

FIG. 4A-FIG. 4E provide results of strand assays as described in Examples 2 and 3 for siRNAs having unmodified Format A and modification formats as indicated.

Figure 4A:
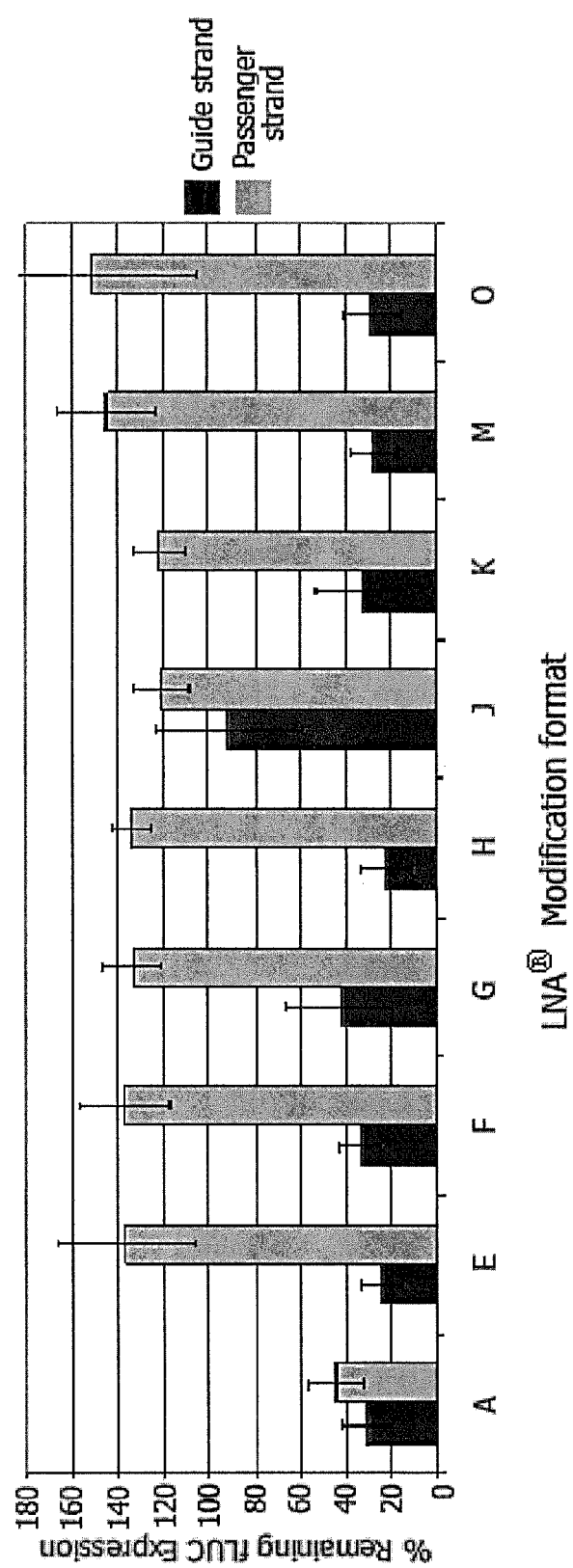

FIG. 4A provides the amount of normalized reporter protein present after carrying out RNAi studies for siRNAs having modification formats as indicated. The dark bars represent knockdown activity by the guide strand and the light bars represent knockdown activity by the passenger strand. To display the distribution of the strandedness results of the modified siRNA strands, the data of FIG. 4B-FIG. 4E are provided in a box plot format, also referred to as a "box and whisker" plot. The dark horizontal bar of a "box and whisker" plot represents the median value of the dataset, the box represents the distribution of the data at the lower quartile and the upper quartile of the dataset, the dotted lines (whiskers) represent the smallest and largest values of the dataset, and the ovals represent outliers in the dataset for each modification format.

Figure 4B:
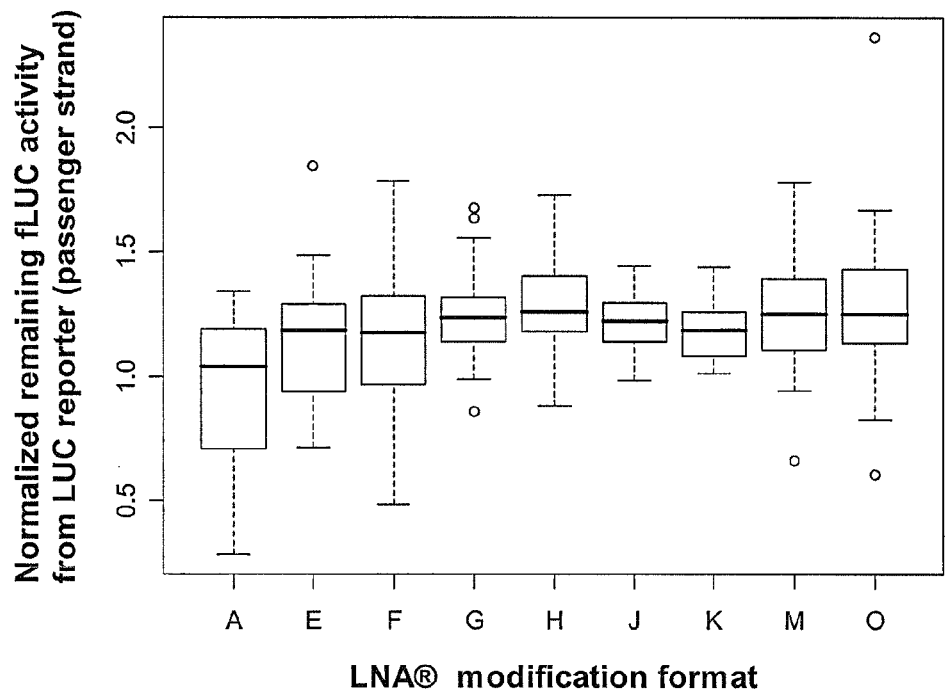

FIG. 4B provides the knockdown activity of the siRNA passenger strand measured by the following formula: Passenger strand activity P=(fLUC activity remaining from reverse clone treated with test siRNA/βgal activity)/(fLUC activity remaining from reverse clone treated with Neg control siRNA/βgal activity). Wilcoxon-test (paired) results comparing each modified format to the unmodified format are as follows: Format E, 0.1434; Format F, 0.1011; Format G, 0.0002052; Format H, 0.0001755; Format J, 0.0002052; Format K, 0.006516; Format M, 0.002246; Format O, 0.0009626.

Figure 4C:
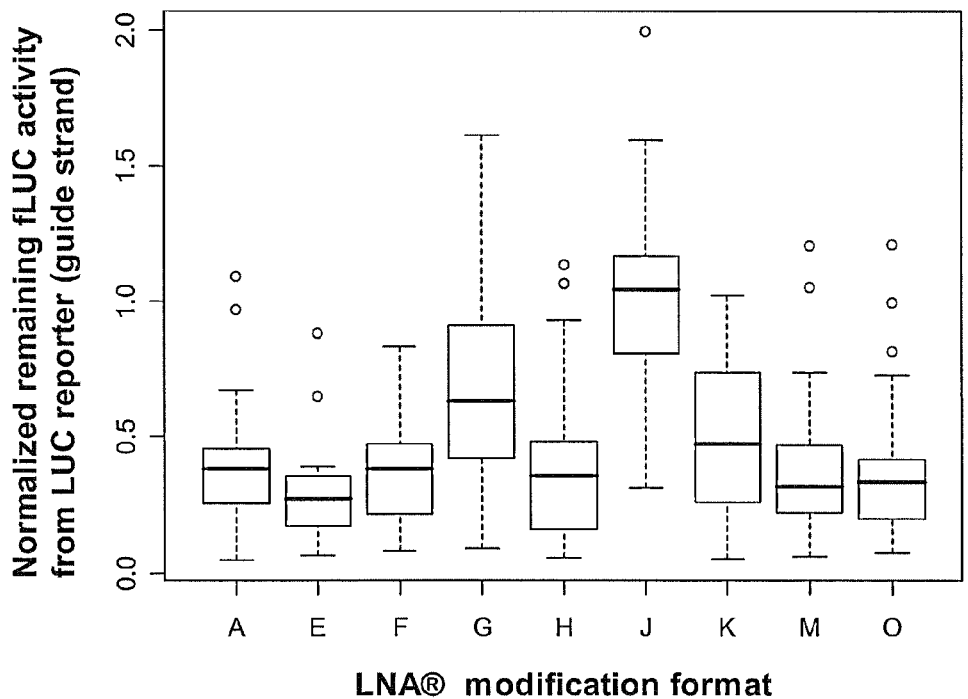

FIG. 4C provides the knockdown activity of the guide strand measured by the following formula: Guide strand activity G=(fLUC activity remaining from forward clone treated with test siRNA/βgal activity)/(fLUC activity remaining from forward clone treated with Neg control siRNA/βgal activity). Wilcoxon-test (paired) results comparing each modified format to the unmodified format are as follows: Format E, 0.0001271; Format F, 0.8774; Format G, 0.0006498; Format H, 0.8115; Format J, 0.000006557; Format K, 0.01051; Format M, 0.7898; Format O, 0.8774.

Figure 4D:
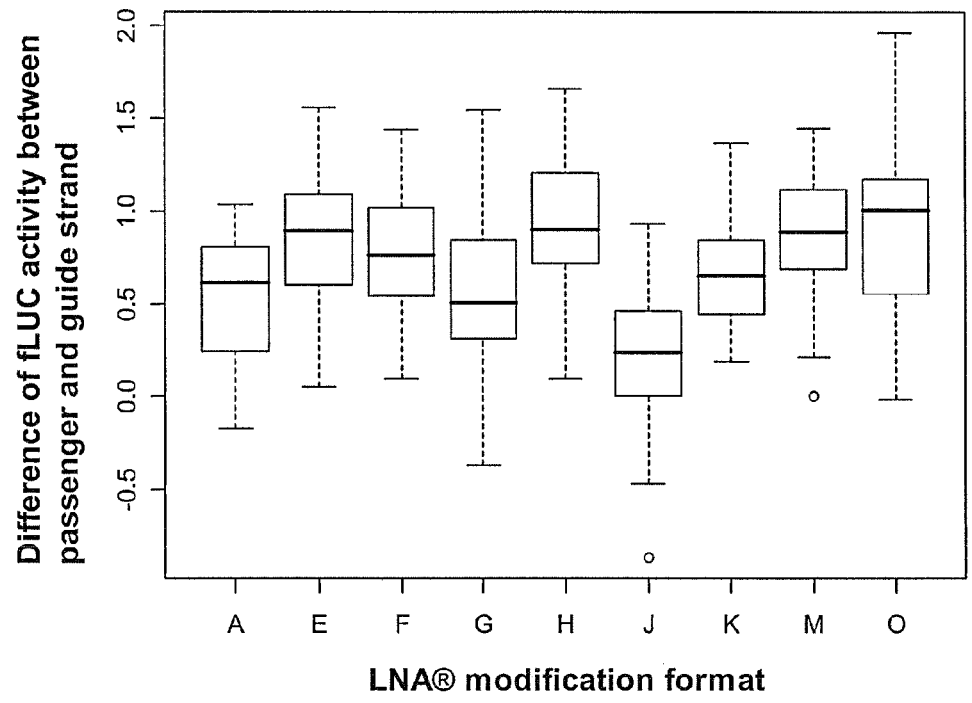

FIG. 4D provides the difference of fLUC activity between the passenger and the guide strands of the siRNAs of FIG. 4B and FIG. 4C. The activity difference was calculated by subtracting the activity of the normalized forward fLUC activity from the normalized reverse fLUC activity or Difference=P−G. Thus, if the passenger strand is less active (less knockdown, i.e., higher luciferase activity) than the guide strand (greater knockdown, i.e., lower luciferase activity), the difference of activity value is expected to be greater than 0. Values less than 0 indicate that the passenger strand is more active than the guide strand. Wilcoxon-test (paired) results comparing each modified format to the unmodified format are as follows: Format E, 0.00792; Format F, 0.06043; Format G, 0.9664; Format H, 0.0014; Format J, 0.008715; Format K, 0.6634; Format M, 0.002516; Format O, 0.0006498.

Figure 4E:
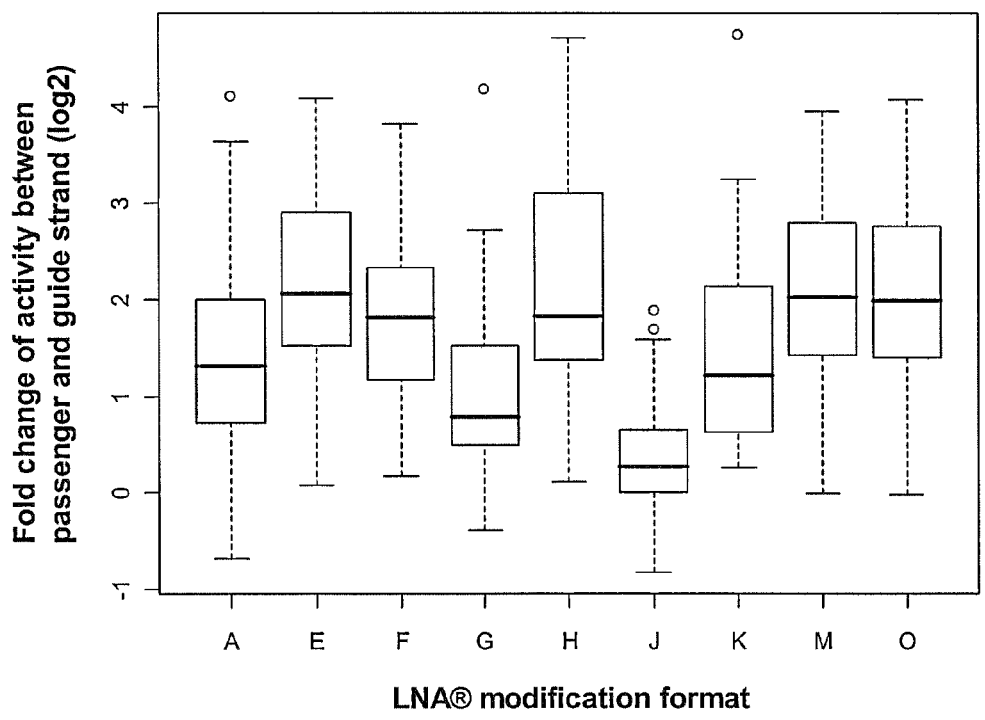

FIG. 4E demonstrates the activity fold change calculated as $(\log_2(P)-\log_2(G))$ which provides a measure of the impact of the modification format on the guide strand as compared to the impact of the format on the passenger strand for the siRNAs of FIG. 4D. Thus, the larger the activity fold change, the greater the guide strand bias of the siRNA. Wilcoxon-test (paired) results comparing each modified format to the unmodified format are as follows: Format E, 0.0002781; Format F, 0.08937; Format G, 0.2076; Format H, 0.01944; Format J, 0.0003223; Format K, 0.8553; Format M, 0.002516; Format O, 0.003504.

Figure 5A:
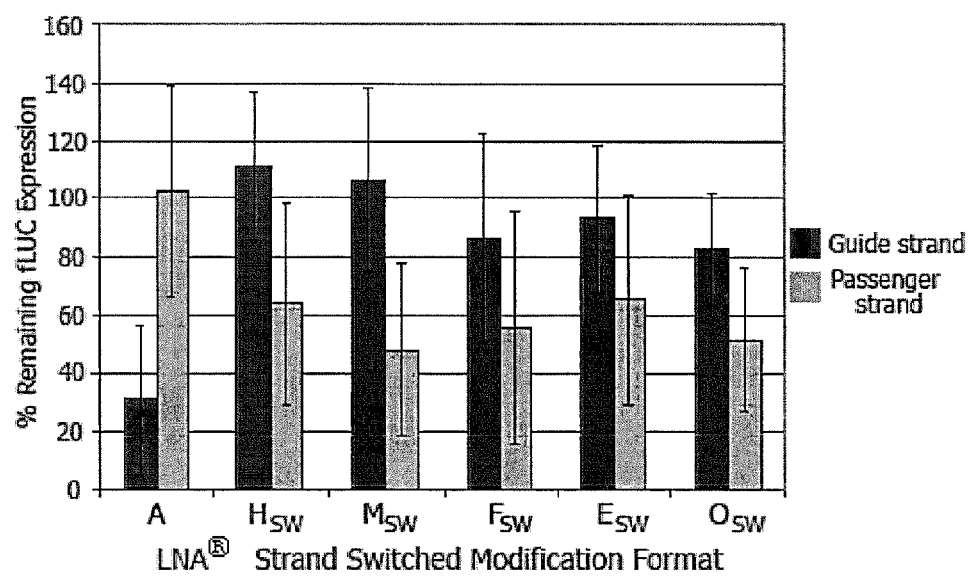
Figure 5B:
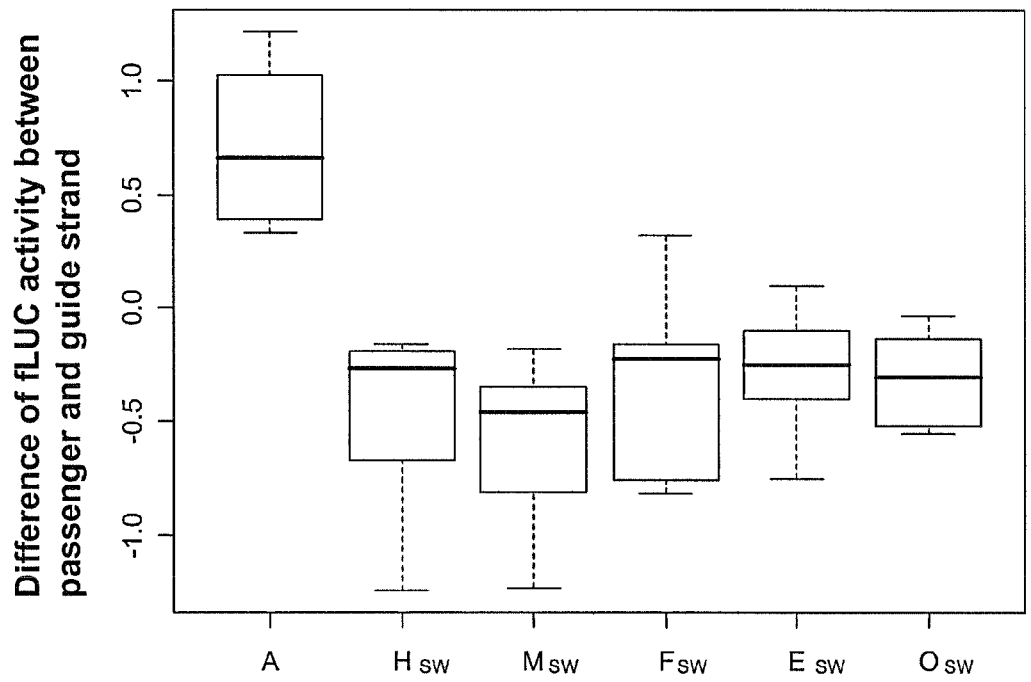
Figure 5C:
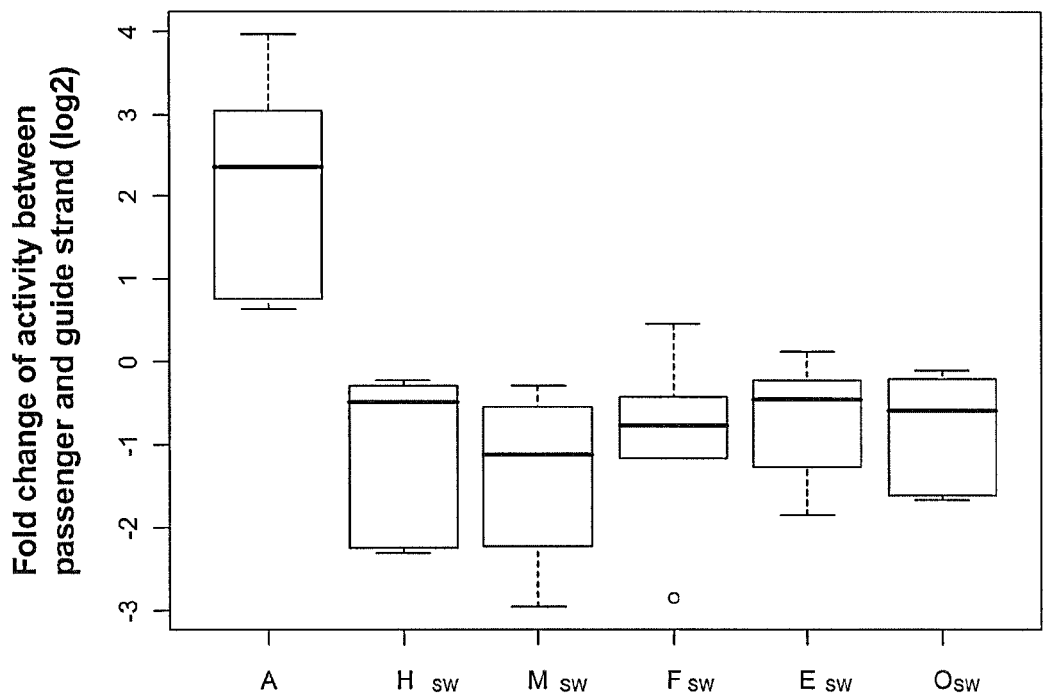

FIG. 5A-FIG. 5C provide results as described in Example 3 for studies in which the modification formats were strand-switched as compared to the studies of FIG. 4A-FIG. 4E. That is, for modification F, for example, the 1, 20, 21 modification of the passenger (sense) strand was introduced into the guide (antisense) strand and the 20, 21 modification of the guide (antisense) strand was introduced into the passenger (sense) strand.

FIG. 5A provides the amount of normalized reporter protein present after carrying out RNAi studies for 12 different siRNAs having the modifications of the strands switched. The dark bars represent knockdown activity by the guide strand and the light bars represent knockdown activity by the passenger strand.

FIG. 5B provides the difference in activity between the passenger strand and guide strand for the siRNAs of FIG. 5A in a box plot format. Wilcoxon-test (paired) results comparing each modified format to the unmodified format are identical for all formats at 0.03125.

FIG. 5C provides the fold change of activity between the passenger strand and the guide strand for the siRNAs of FIG. 5B. Wilcoxon-test (paired) results comparing each modified format to the unmodified format are identical for all formats at 0.03125.

Figure 6A:
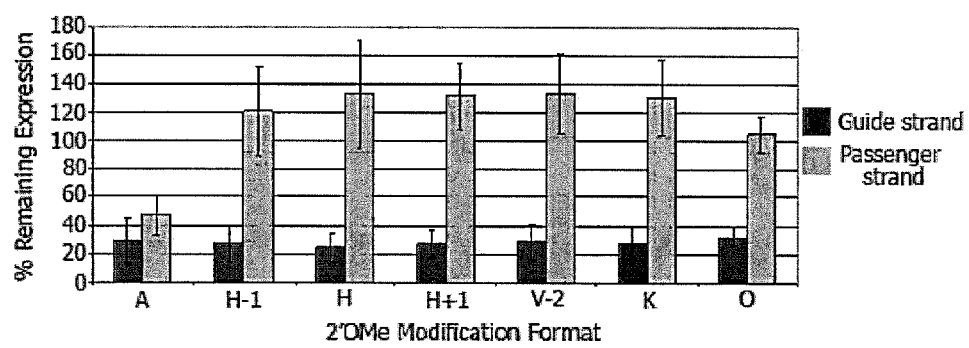
Figure 6B:
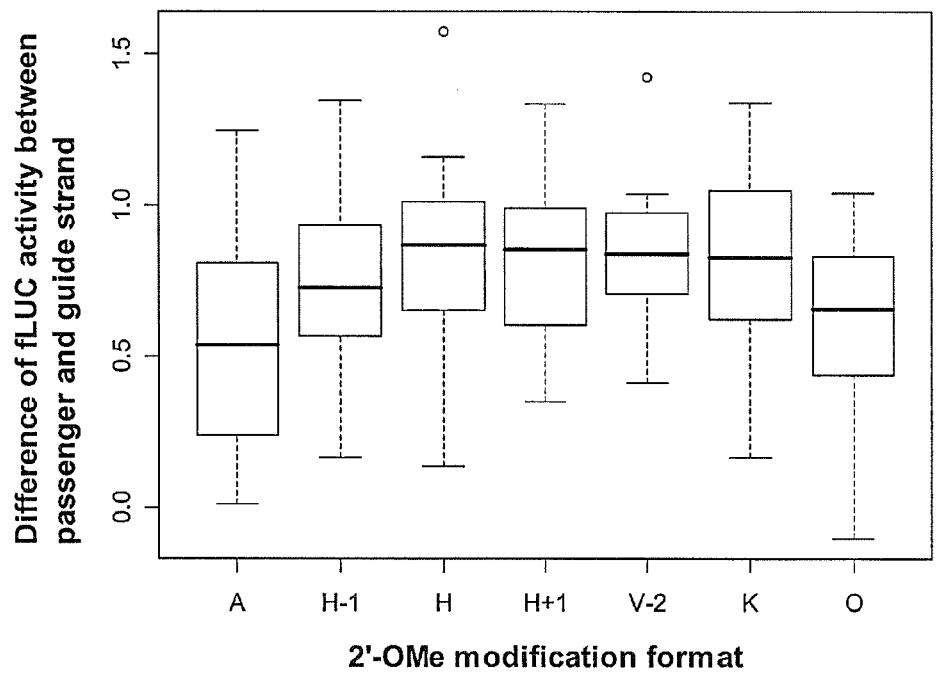
Figure 6C:
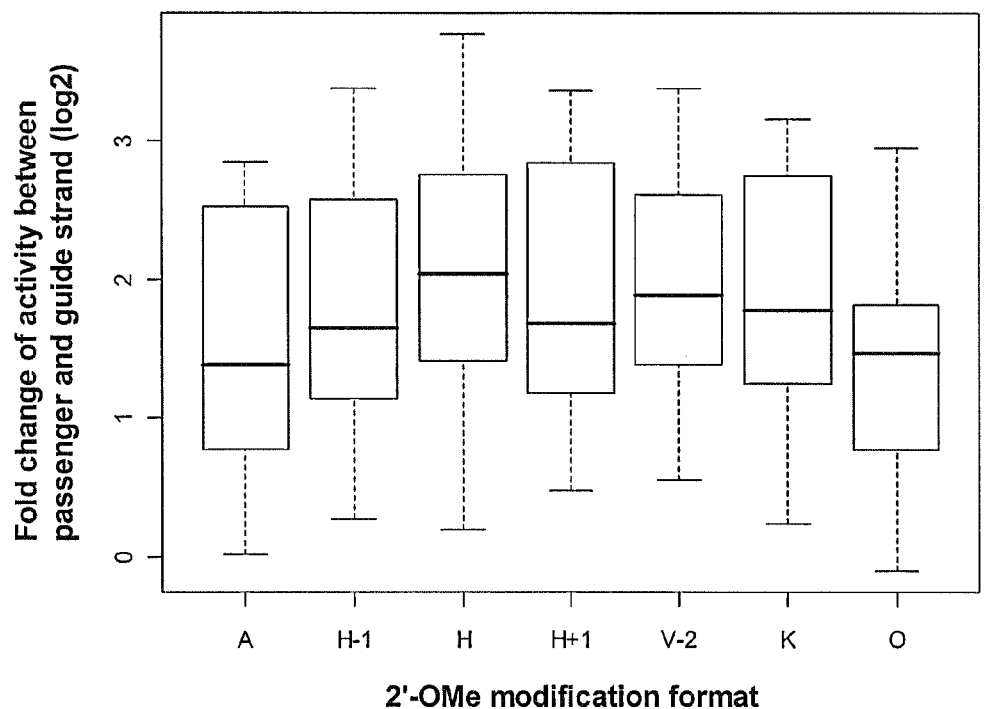

FIG. 6A-FIG. 6C provide results of strand assays as described in Example 3 for studies in which modified nucleotides of modification formats were 2'-O methylated.

FIG. 6A provides the amount of normalized reporter protein present after carrying out RNAi studies for 6 different siRNAs having the modifications as indicated. The dark bars represent knockdown activity by the guide strand and the light bars represent knockdown activity by the passenger strand.

FIG. 6B provides, in a box plot format, the difference of fLUC activity between the passenger strand and the guide strand for the set of siRNAs of FIG. 6A plus an additional set of 18 different siRNAs as described in Example 3. Wilcoxon-test (paired) results comparing each modified format to the unmodified format are as follows: Format H−1, 0.001918; Format H, 0.00001574; Format H+1, 0.001091; Format V−2, 0.0002131; Format K, 0.0003619; Format O, 0.406.

FIG. 6C provides the fold change of activity between the passenger strand and the guide strand for the siRNAs of FIG. 6B. Wilcoxon-test (paired) results comparing each modified format to the unmodified format are as follows: Format H−1, 0.02514; Format H, 0.00001574; Format H+1, 0.007443; Format V−2, 0.0001464; Format K, 0.0003619; Format O, 0.5446.

Figure 7A:
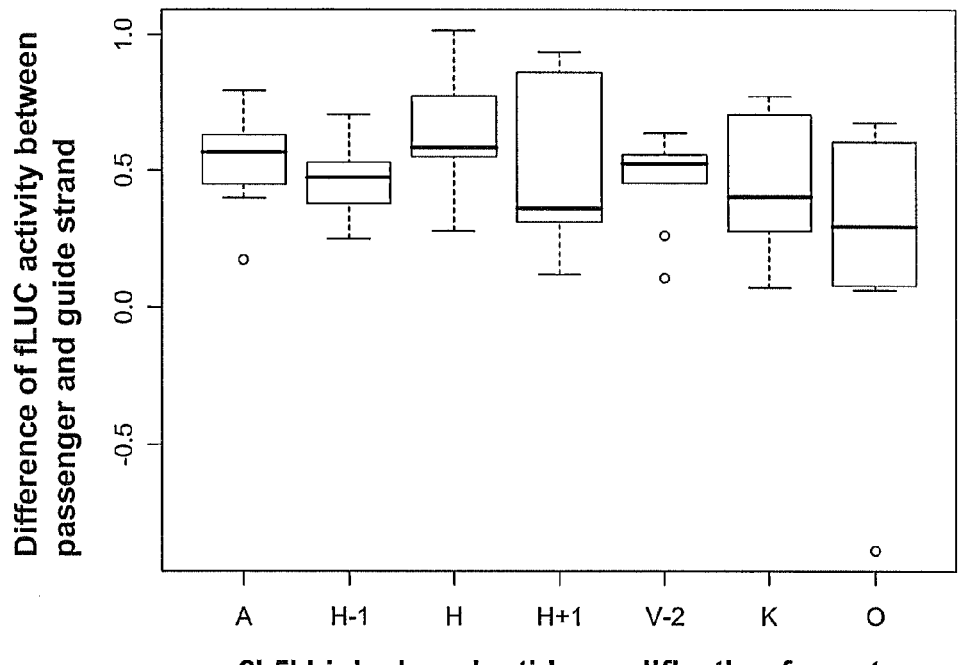
Figure 7B:
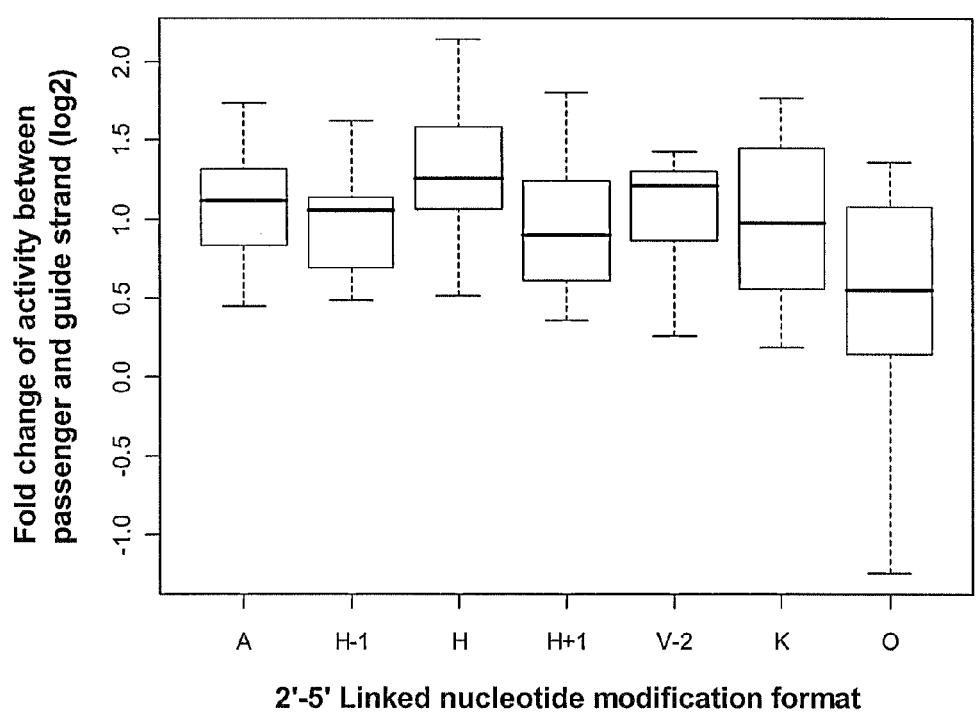

FIG. 7A-FIG. 7B provide results of strand assays as described in Example 3 for studies in which modified nucleotides of modification formats were 2',5'-linked nucleotides.

FIG. 7A provides the difference in guide and passenger strand knockdown activity for siRNAs having unmodified Format A and siRNAs having Modification Formats H−1, H, H+1, V−2, K and O. Wilcoxon-test (paired) results comparing each modified format to the unmodified format are as follows: Format H−1, 0.3594; Format H, 0.07422; Format H+1, 0.5703; Format V−2, 0.4258; Format K, 0.2031; Format O, 0.01953.

FIG. 7B provides the fold change of knockdown activity between the passenger strand and the guide strand for the siRNAs of FIG. 7A. Wilcoxon-test (paired) results comparing each modified format to the unmodified format are as follows: Format H−1, 0.3008; Format H, 0.01953; Format H+1, 0.2031; Format V−2, 0.4961; Format K, 0.1921; Format O, 0.00909.

Figure 8:
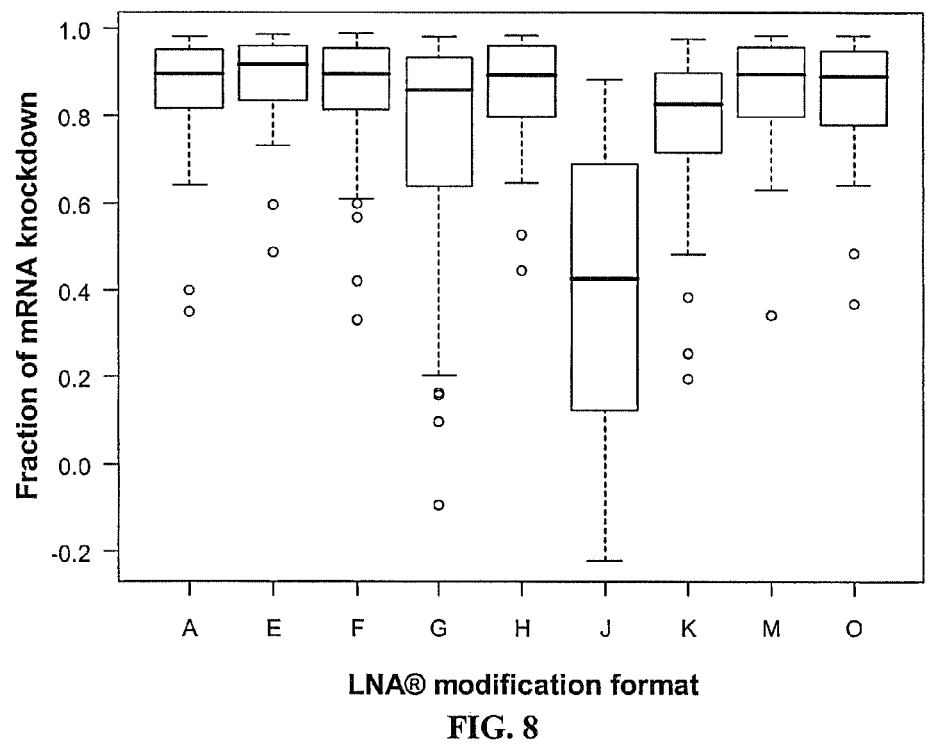

FIG. 8 provides knockdown activity data for six siRNAs for each of 8 endogenous targets. Each of the 48 siRNAs have modification formats as indicated, which formats incorporated bicyclo-modified nucleotides as described in Example 4. Wilcoxon-test (paired) results comparing each modified format to the unmodified format are as follows: Format E, 0.000000008657; Format F, 0.4631; Format G, 0.000009698; Format H, 0.5569; Format J, 0.00000000191; Format K, 0.00001336; Format M, 0.7269; Format O, 0.0593.

Figure 9A:
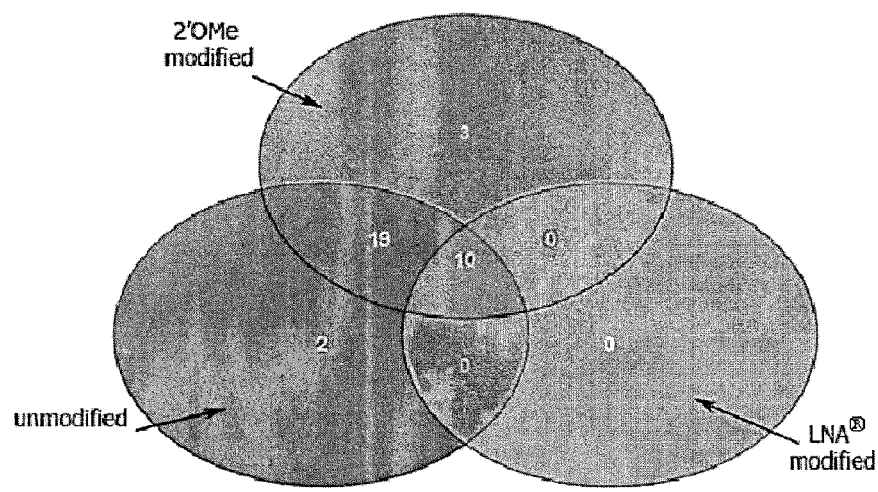
Figure 9B:
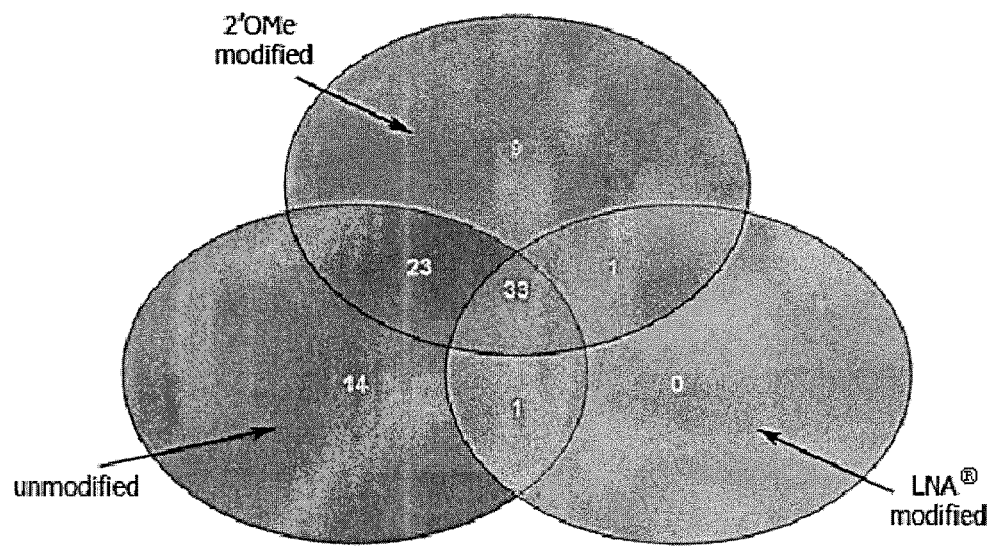
Figure 9C:
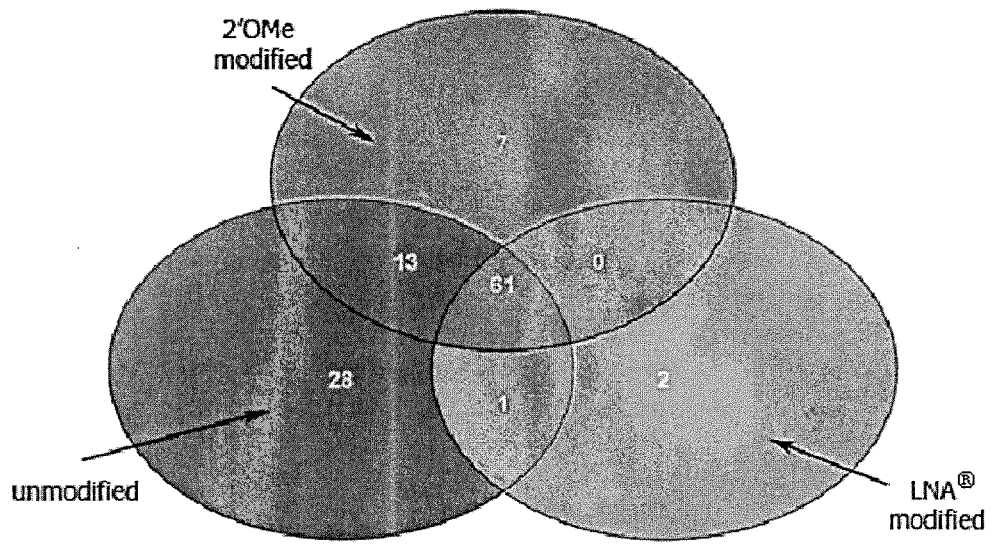

FIG. 9A-FIG. 9C provide Venn diagrams of the intersection of 2-fold differentially expressed genes between unmodified, 2'-O-methyl- or bicyclo-modified siRNAs as determined by microarray analysis and as described by Example 5. For each diagram, the lower left set (red if in color) indicates the genes changed 2-fold or greater in the unmodified siRNA treated samples, the upper set (blue if in color) indicates the genes changed 2-fold or greater in the 2'-O-methyl Format H modified siRNA treated samples, and the lower right set (green if in color) indicates the genes changed 2-fold or greater in the bicyclo modified nucleotide (LNA®) Format H modified siRNA treated samples.

FIG. 10A-FIG. 10E provide data on the impact of LNA® modification formats on on-target and off-target phenotypes in cell biology studies. The negative control (Neg) is a scrambled non-targeting siRNA for which mitosis or apoptosis quantitation is normalized to a value of 1.0. See Example 6.

Figure 10A:
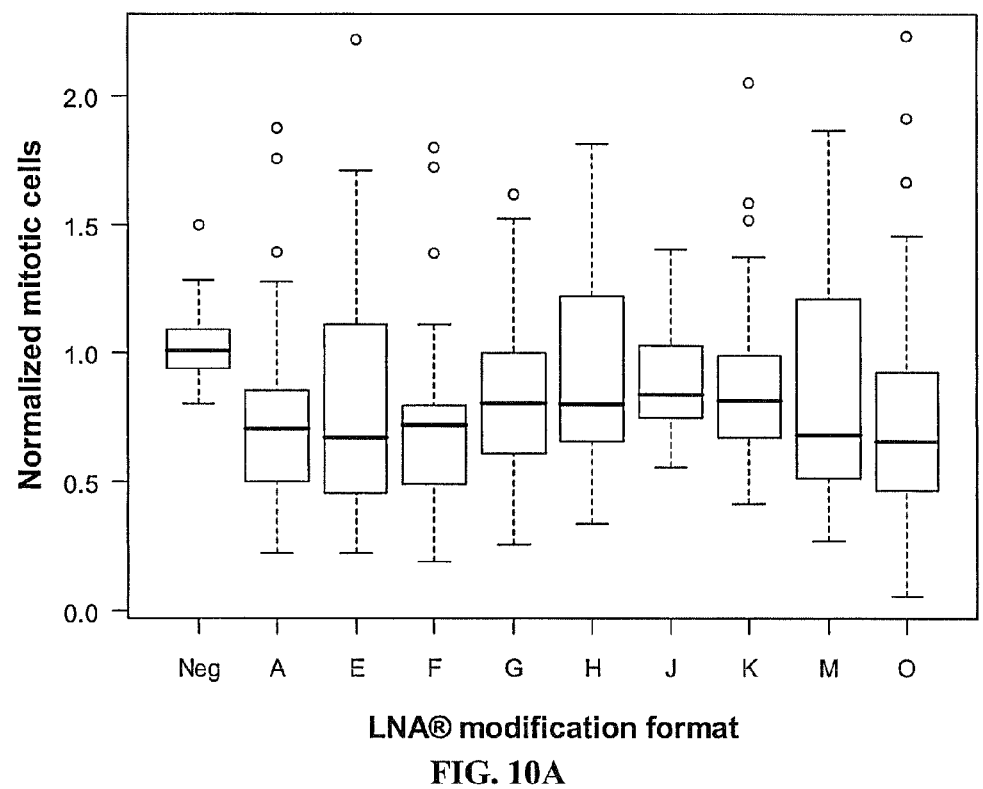

FIG. 10A provides a box plot of normalized mitotic cells resulting from silencing by siRNA having LNA® modification Formats E, F, G, H, J, K, M and O for a set of gene targets, the knockdown of a subset of which is expected to increase mitosis, a subset of which is expected to have no effect on mitosis, and a subset of which is expected to decrease mitosis as described by Example 6. Wilcoxon-test (paired) results comparing each modified format to the unmodified siRNA format are as follows: Format E, 0.805; Format F, 0.5483; Format G, 0.3215; Format H, 0.004561; Format J, 0.000952; Format K, 0.01974; Format M, 0.1007; Format O, 0.9438.

Figure 10B:
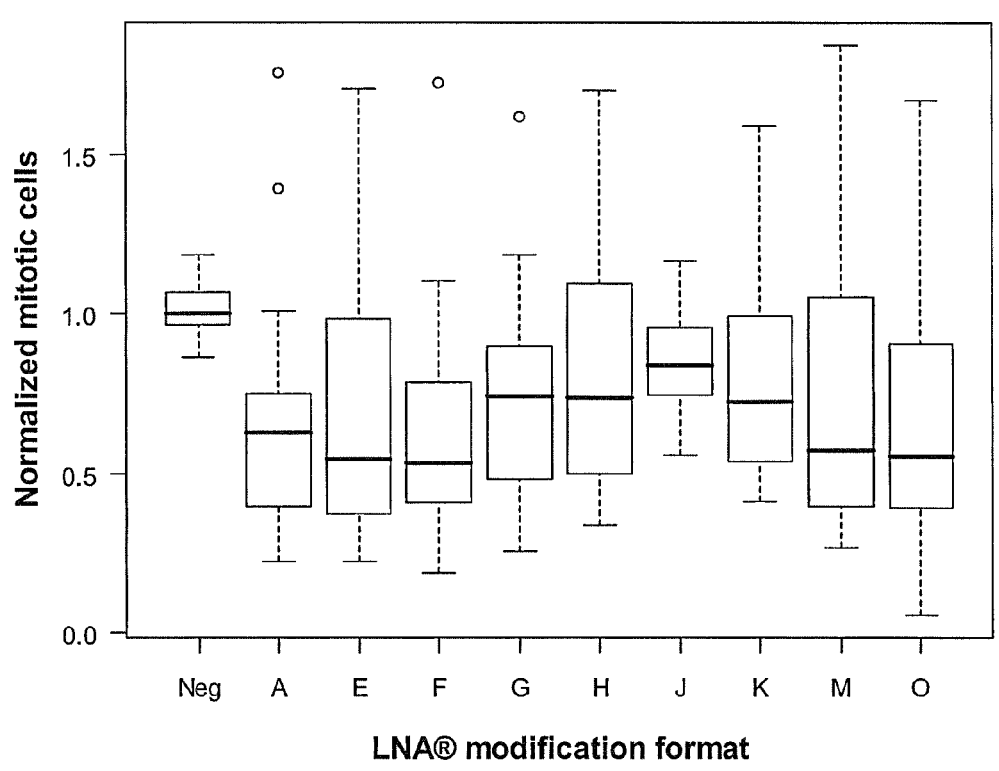

FIG. 10B provides a box plot as for FIG. 10A for a subset of genes, knockdown of which is expected to decrease mitosis. Wilcoxon-test (paired) results comparing each modified format to the unmodified siRNA format are as follows: Format E, 0.3247; Format F, 0.4683; Format G, 0.1815; Format H, 0.03423; Format J, 0.01387; Format K, 0.09874; Format M, 0.5509; Format O, 0.6705.

Figure 10C:
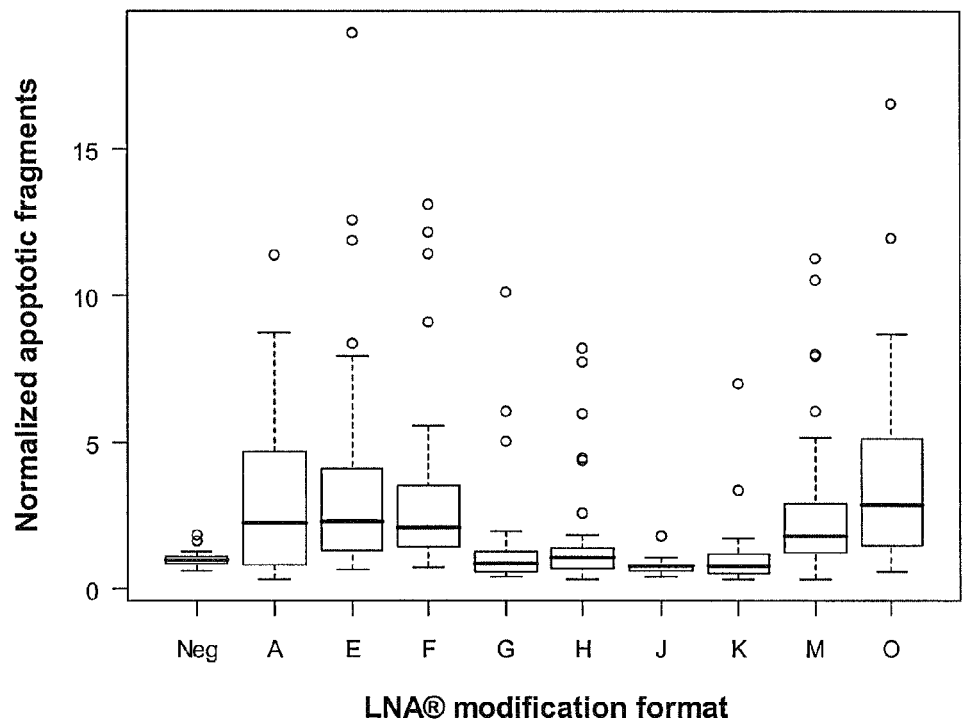

FIG. 10C provides a box plot of normalized apoptotic fragments resulting from silencing by siRNA having LNA® modification Formats E, F, G, H, J, K, M and O for a set of gene targets, the knockdown of a subset of which is expected to increase apoptosis and a subset of which is expected to have no effect on apoptosis as described in Example 6. Wilcoxon-test (paired) results comparing each modified format to the unmodified siRNA format are as follows: Format E, 0.2641; Format F, 0.5366; Format G, 0.0001888; Format H, 0.0000102; Format J, 0.00000263; Format K, 0.000000553; Format M, 0.5366; Format O, 0.05753.

Figure 10D:
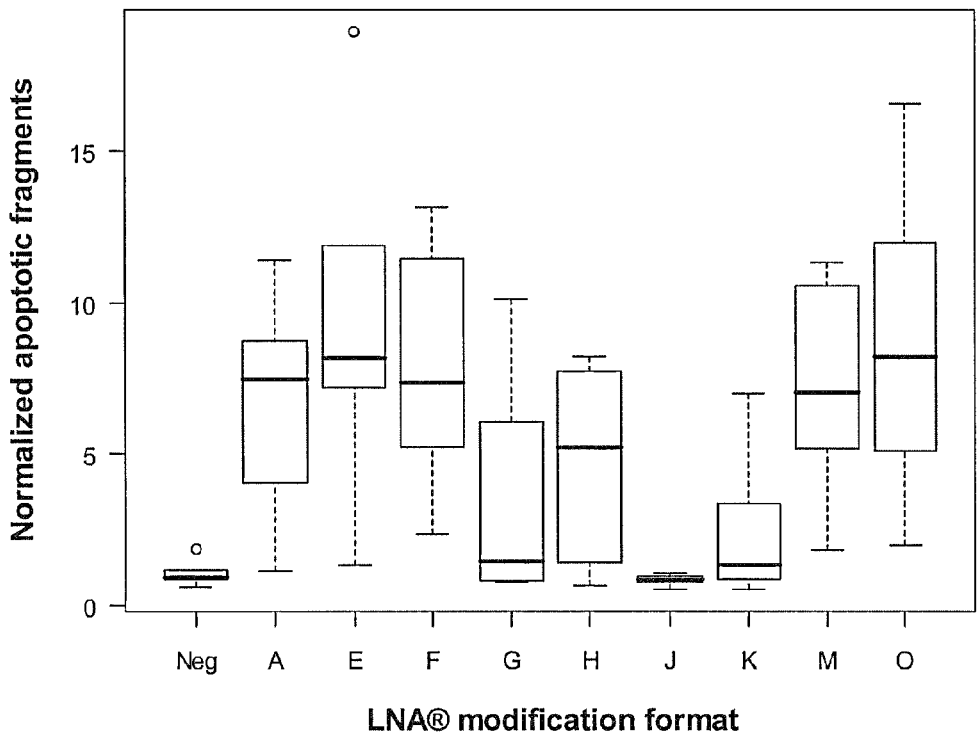

FIG. 10D provides a box plot as for FIG. 10C for a subset of genes, knockdown of which is expected to increase apoptosis as described in Example 6. Wilcoxon-test (paired) results comparing each modified format to the unmodified siRNA format are as follows: Format E, 0.2188; Format F, 0.4375; Format G, 0.3125; Format H, 0.2188; Format J, 0.03125; Format K, 0.03125; Format M, 1; Format O, 0.2188.

Figure 10E:
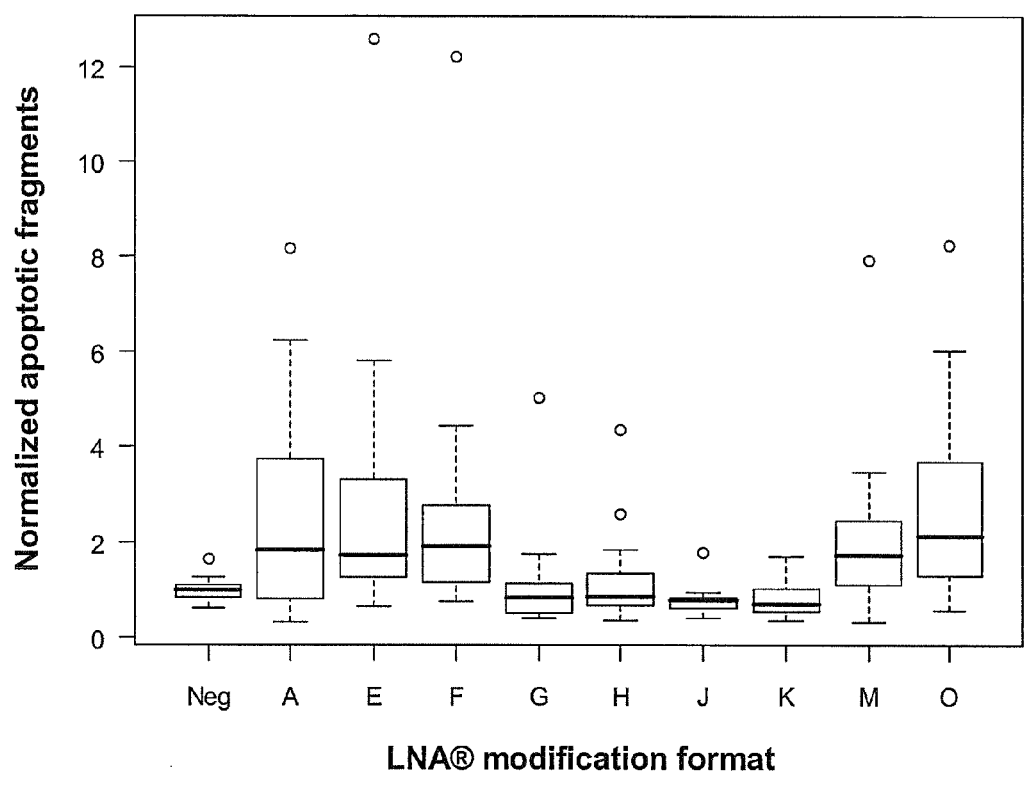

FIG. 10E provides a box plot as for FIG. 10C for a subset of genes, knockdown of which is expected to have no effect on apoptosis as described in Example 6. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median and greater distribution of data as compared to the Neg control. Wilcoxon-test (paired) results comparing each modified format to the unmodified siRNA format are as follows: Format E, 0.5303; Format F, 0.804; Format G, 0.00005488; Format H, 0.00001347; Format J, 0.0001253; Format K, 0.00003023; Format M, 0.441; Format O, 0.1551.

FIG. 11A-FIG. 11F provide data on the impact of 2'-O-methylated modification formats on on-target and off-target phenotypes in cell biology studies. The negative control (Neg) is a scrambled non-targeting siRNA for which mitosis or apoptosis quantitation is normalized to a value of 1.0. See Example 6.

Figure 11A:
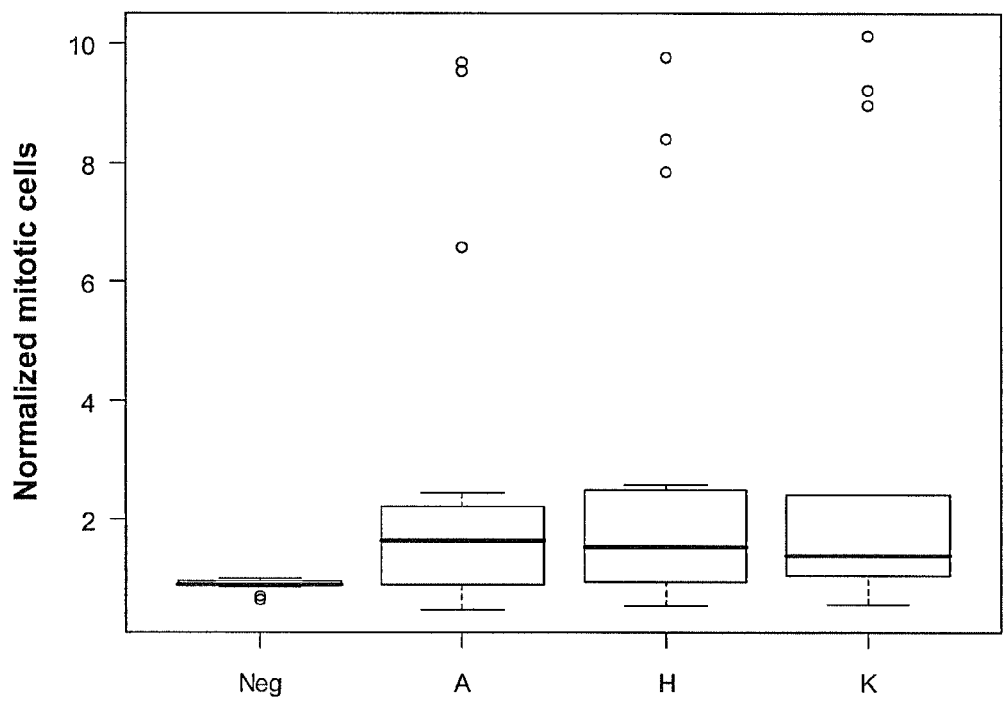

FIG. 11A provides a box plot of normalized mitotic cells resulting from silencing by siRNA having unmodified Format A, and having 2'-O-methyl modification Formats H and K for a set of gene targets, the knockdown of a subset of which is expected to increase mitosis, and a subset of which is expected to have no effect on mitosis as described by Example 6. Wilcoxon-test (paired) results comparing each modified format to the unmodified siRNA format are as follows: Format H, 0.3529; Format K, 0.3289.

Figure 11B:
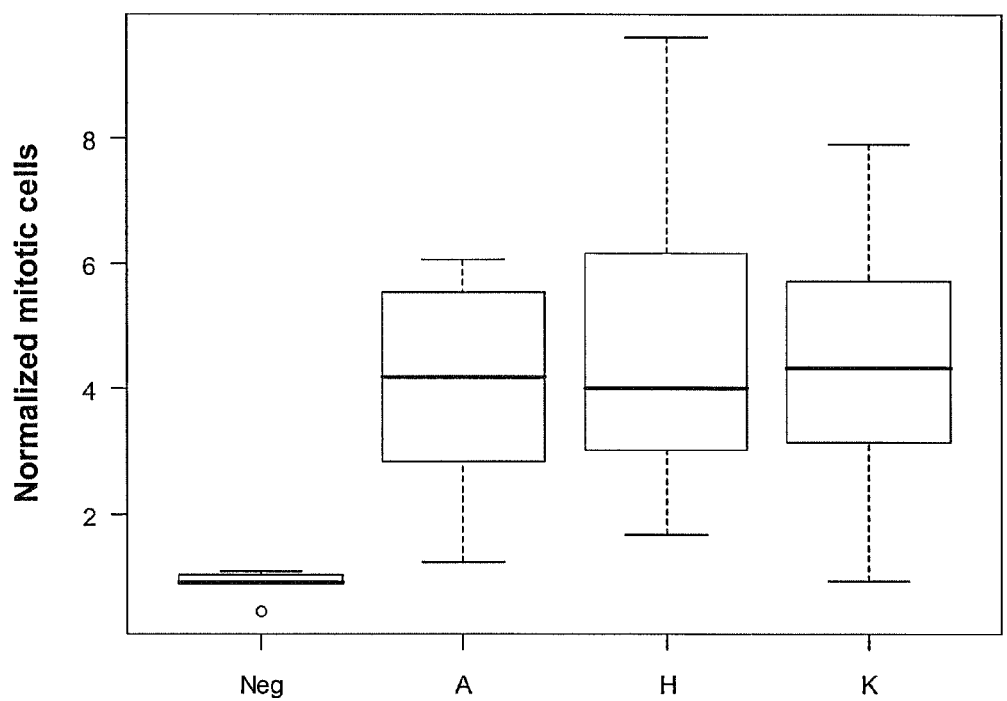
Figure 11C:
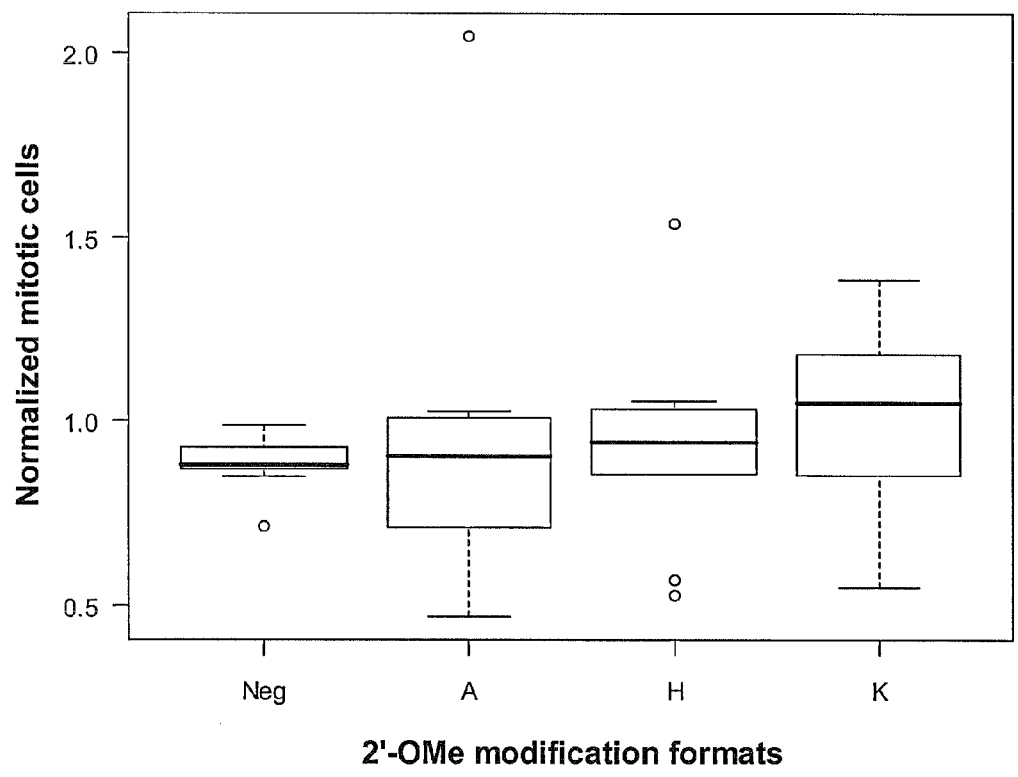

FIG. 11B provides a box plot as for FIG. 11A for the subset of genes, knockdown of which is expected to increase mitosis. Wilcoxon-test (paired) results comparing each modified format to the unmodified siRNA format are as follows: Format H, 0.3125; Format K, 0.5469.

FIG. 11C provides a box plot as for FIG. 11A for the subset of genes, knockdown of which is expected to have no effect on mitosis. However, siRNAs that have empirically demonstrated mitosis off-target effects were specifically chosen for study to determine if such siRNAs, when modification-formatted, would eliminate or reduce the off-target effects. That the siRNAs have off-target effects is evidenced by the box plot for unmodified Format A which has a greater distribution of data as compared to the Neg control. Wilcoxon-test (paired) results comparing each modified format to the unmodified siRNA format are as follows: Format H, 0.9102; Format K, 0.4961.

Figure 11D:
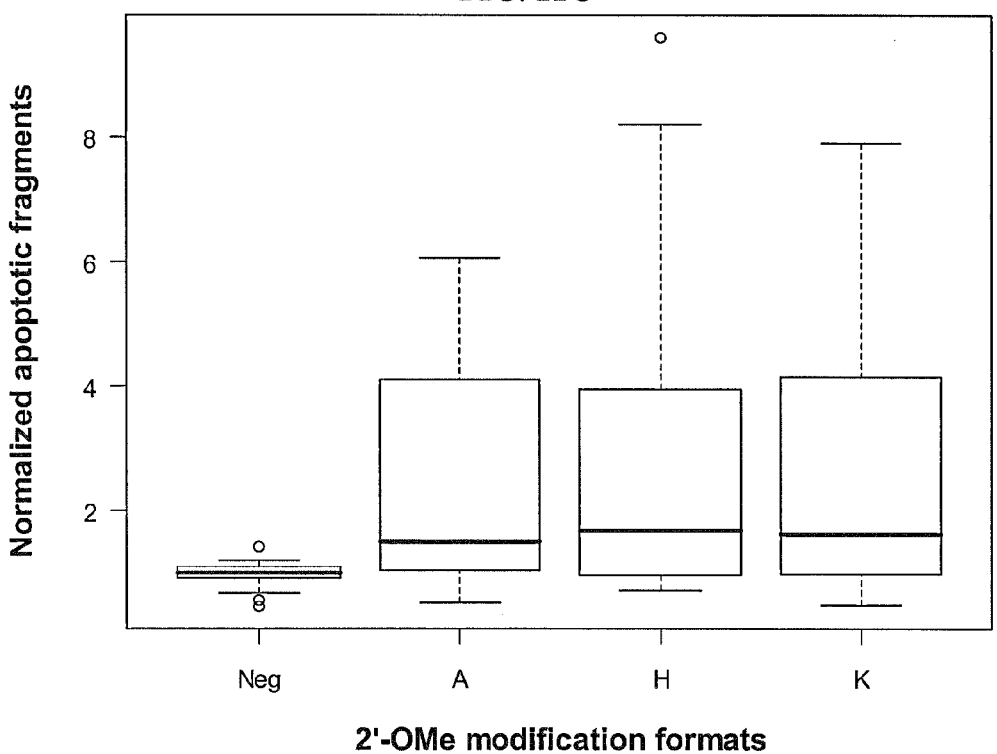

FIG. 11D provides a box plot of normalized apoptotic fragments resulting from silencing by siRNA having 2'-O-methyl modification Formats H and K for a set of gene targets, the knockdown of a subset of which is expected to increase apoptosis and a subset of which is expected to have no effect on apoptosis as described in Example 6. Wilcoxon-test (paired) results comparing each modified format to the unmodified siRNA format are as follows: Format H, 0.3529; Format K, 0.3529.

Figure 11E:
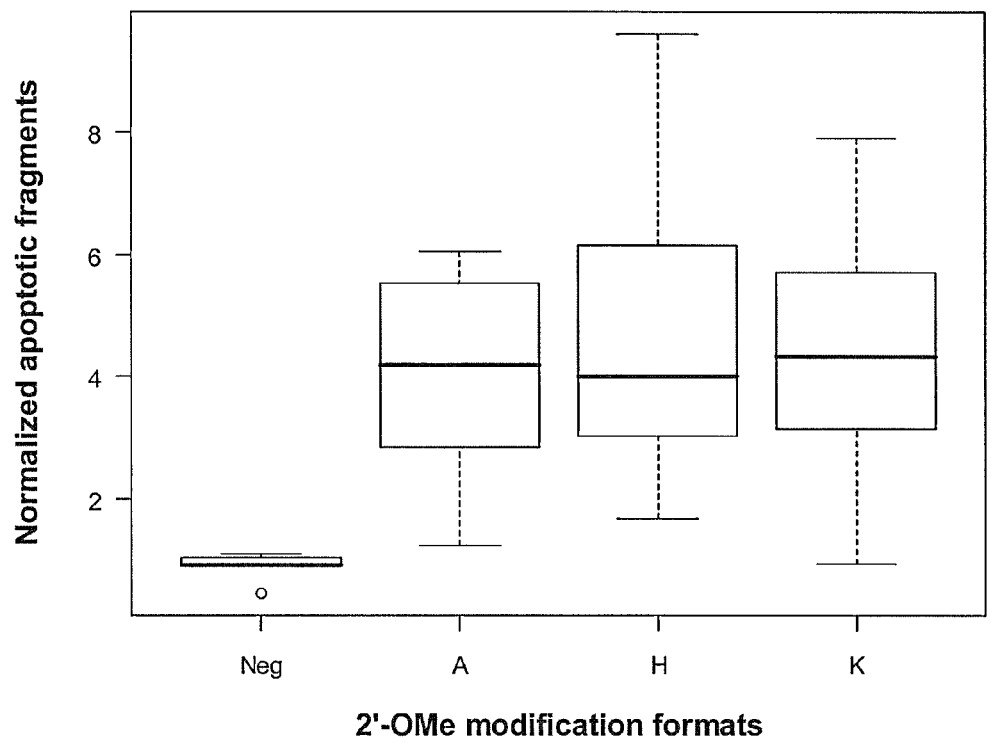

FIG. 11E provides a box plot as for FIG. 11D for the subset of genes, knockdown of which is expected to increase apoptosis as described in Example 6. Wilcoxon-test (paired) results comparing each modified format to the unmodified siRNA format are as follows: Format H, 0.3125; Format K, 0.5469.

Figure 11F:
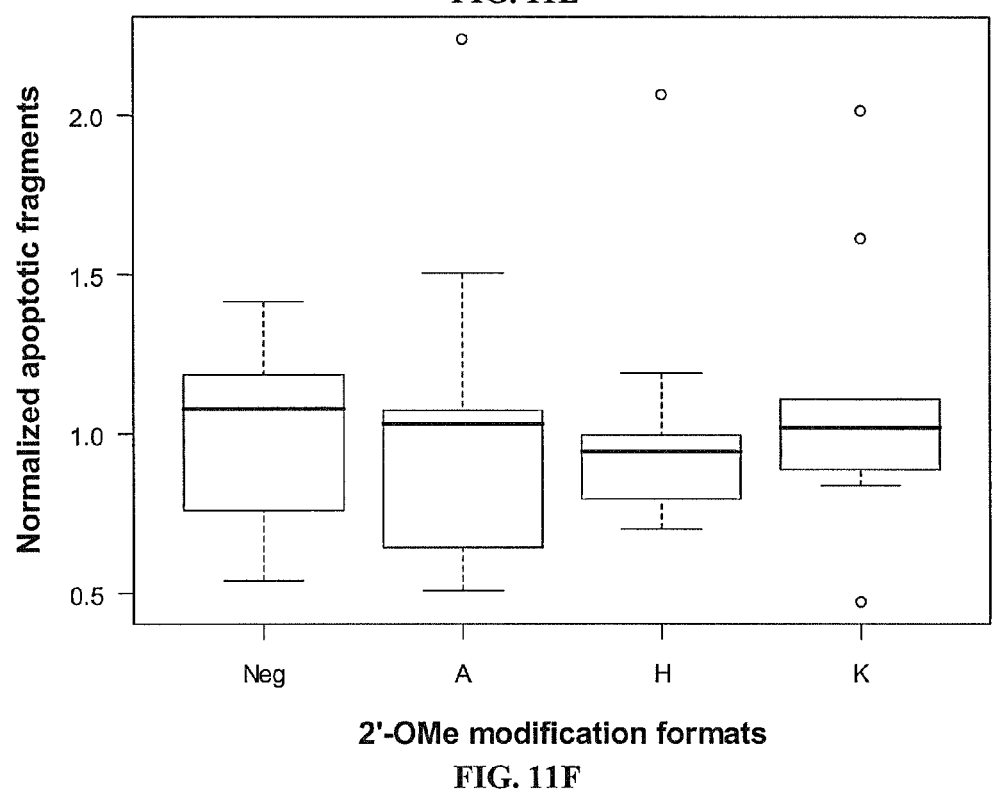

FIG. 11F provides a box plot as for FIG. 11D for the subset of genes, knockdown of which is expected to have no effect on apoptosis as described by Example 6. However, siRNAs that have empirically demonstrated apoptosis off-target effects were specifically chosen for study to determine if such siRNAs, when modification-formatted, would eliminate or reduce the off-target effects. Wilcoxon-test (paired) results comparing each modified format to the unmodified siRNA format are as follows: Format H, 0.9102; Format K, 0.7344.

Figures 1, 12A:
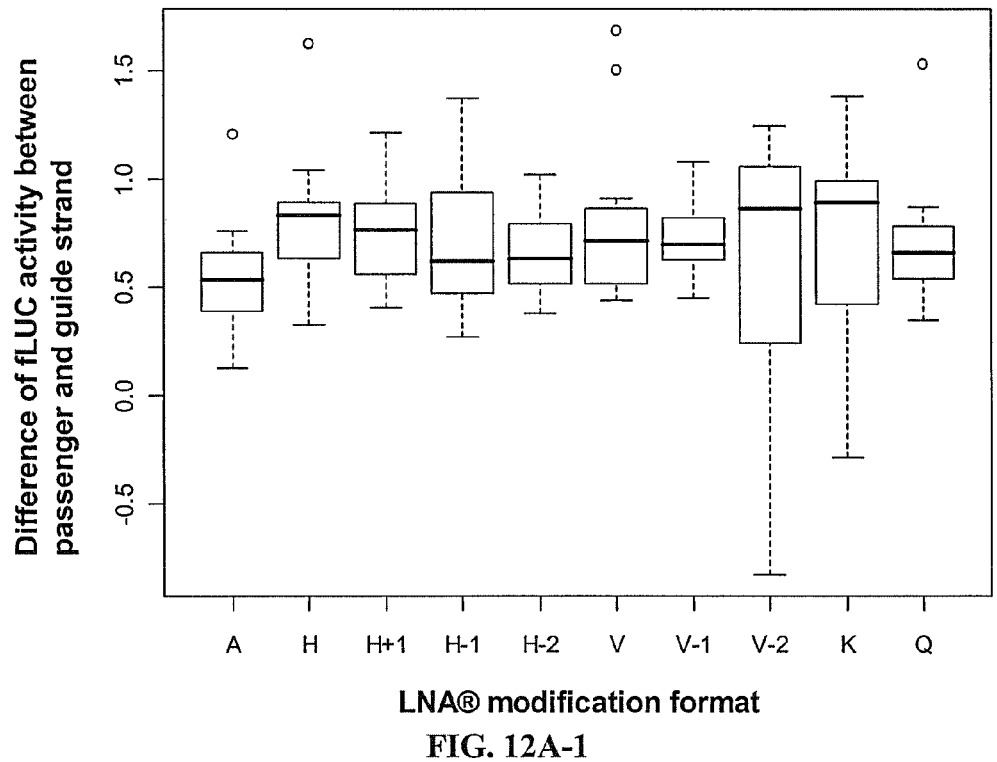

FIG. 12A-1 provides the difference in activity between the passenger strand and guide strand calculated as P–G with P and G defined as for FIG. 4B and FIG. 4C for the unmodified format A and for test formats H, H+1, H–1, H–2, V, V–1, V–2, K and Q where the modification is LNA® residues. Wilcoxon-test (paired) results comparing each modified format to the unmodified format are as follows: Format H, 0.04199; Format H+1, 0.123; Format H–1, 0.1748; Format H–2, 0.2402; Format V, 0.06738; Format V–1, 0.05371; Format V–2, 0.5771; Format K, 0.4648; Format Q, 0.1016.

Figures 2, 12A:
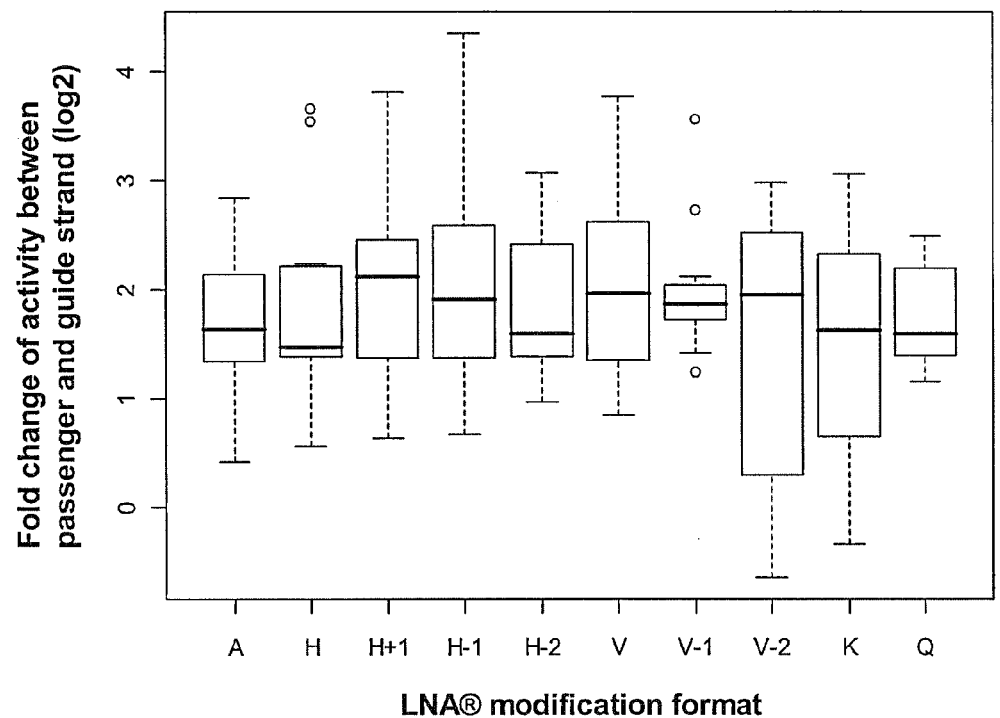

FIG. 12A-2 provides the fold change of activity between the passenger strand and the guide strand for the siRNAs of FIG. 12A-1. Wilcoxon-test (paired) results comparing each modified format to the unmodified format are as follows: Format H, 0.3652; Format H+1, 0.2783; Format H–1, 0.2402; Format H–2, 0.4131; Format V, 0.2061; Format V–1, 0.1016; Format V–2, 0.7002; Format K, 0.6377; Format Q, 0.7002.

Figure 12B:
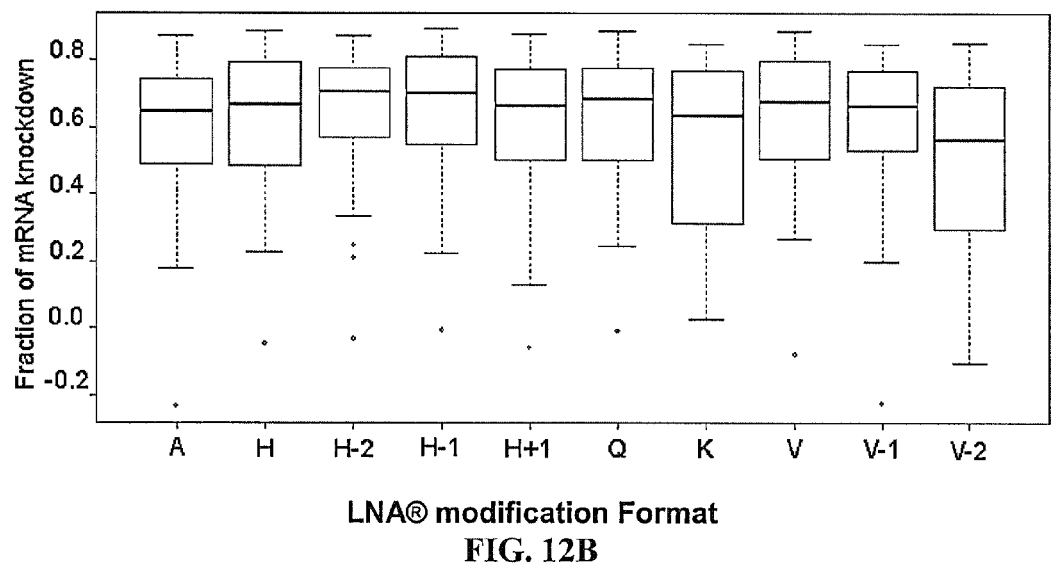

FIG. 12B provides knockdown activity data for endogenous targets for siRNAs having unmodified Format A and for LNA® modification Formats H, H–2, H–1, H+1, Q, K, V, V–1, and V–2 as described in Example 6. Wilcoxon-test (paired) results comparing each modified format to the unmodified format are as follows: Format H, 0.029598160; Format H–2, 0.004296849; Format H–1, 0.000833165; Format H+1, 0.052779900; Format Q, 0.011454170; Format K, 0.745852000; Format V, 0.005660834; Format V–1, 0.998100800; Format V–2, 0.374661100.

Figure 12C:
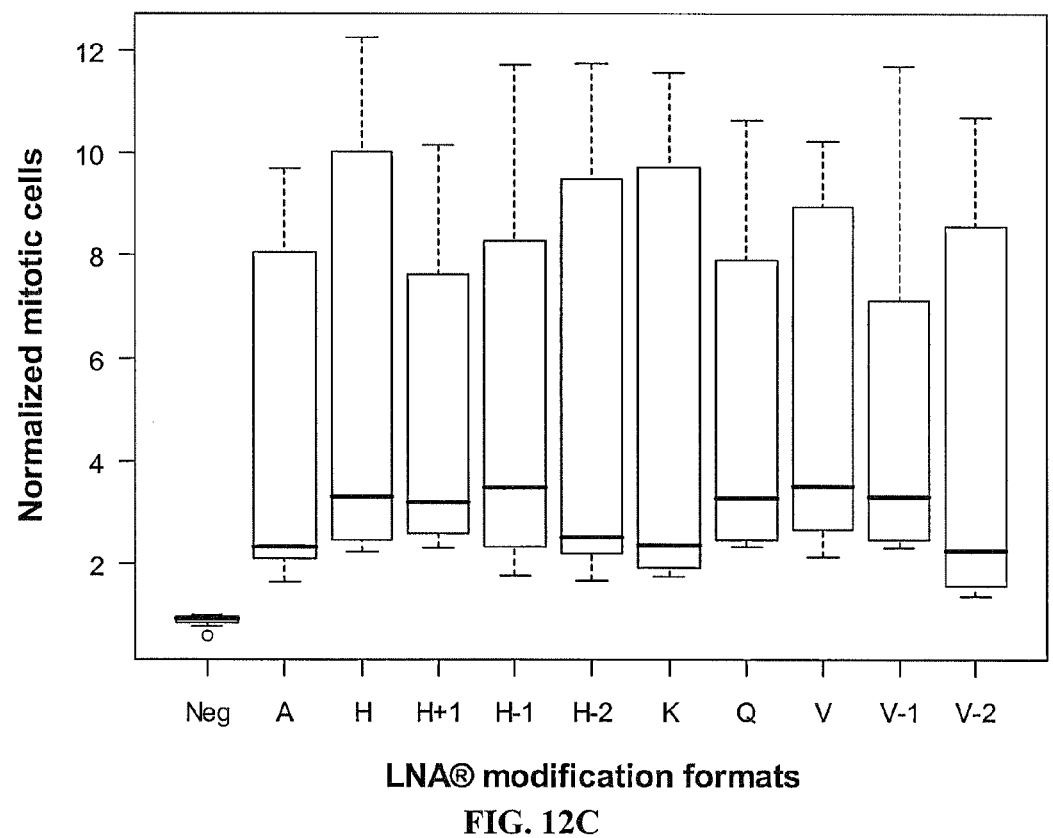

FIG. 12C provides a box plot of normalized mitotic cells resulting from silencing by siRNA having unmodified Format A and for LNA® modification Formats H, H+1, H–1, H–2, K, Q, V, V–1, and V–2, for a set of gene targets, the knockdown of which is expected to increase mitosis as described by Example 6. The negative control (Neg) is a scrambled non-targeting siRNA for which mitosis quantitation is normalized to a value of 1.0. Wilcoxon-test (paired) results comparing each modified format to the unmodified siRNA format are as follows: Format H, 0.01563; Format H+1, 0.1953; Format H–1, 0.07813; Format H–2, 0.07813; Format V, 0.05469; Format V–1, 0.1953; Format V–2, 1; Format K, 0.1953; Format Q, 0.1953.

Figure 12D:
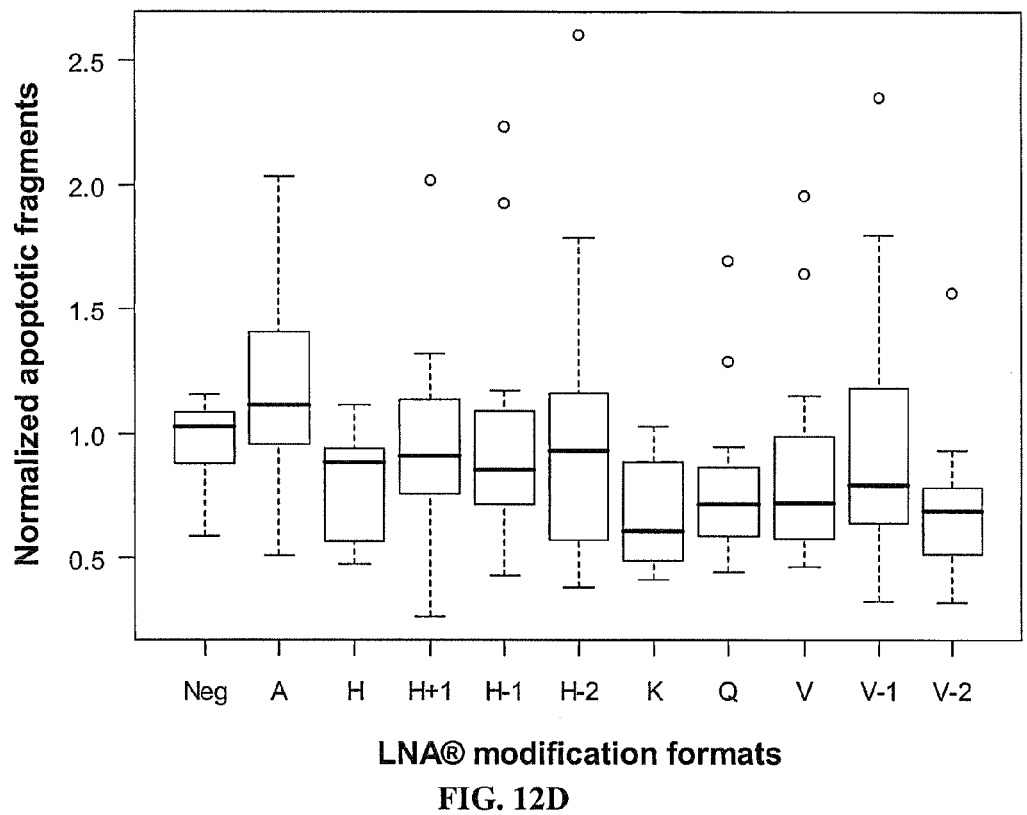

FIG. 12D provides a box plot of normalized apoptotic fragments resulting from silencing by siRNA having unmodified Format A and for LNA® modification Formats H, H+1, H–1, H–2, K, Q, V, V–1, and V–2, for a set of gene targets, the knockdown of which is expected to have no effect on apoptosis. The negative control (Neg) is a scrambled non-targeting siRNA for which apoptosis quantitation is normalized to a value of 1.0. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median and greater distribution of data as compared to the Neg control. Wilcoxon-test (paired) statistical significance calculations for normalized apoptotic fragments as a % of control comparing the unmodified Format A control to the respective modification format are: Format H, 0.04199; Format H+1, 0.2061; Format H−1, 0.2783; Format H−2, 0.6377; Format V, 0.05371; Format V−1, 0.4648; Format V−2, 0.006836; Format K, 0.01855; Format Q, 0.024.

Figures 1, 13A:
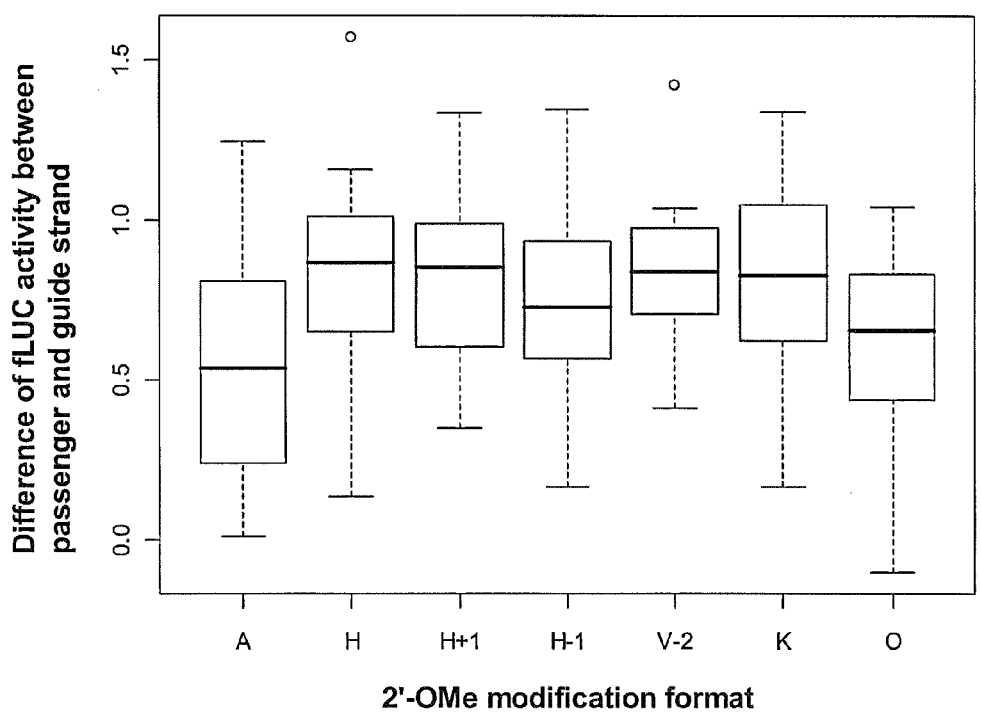
Figures 2, 13A:
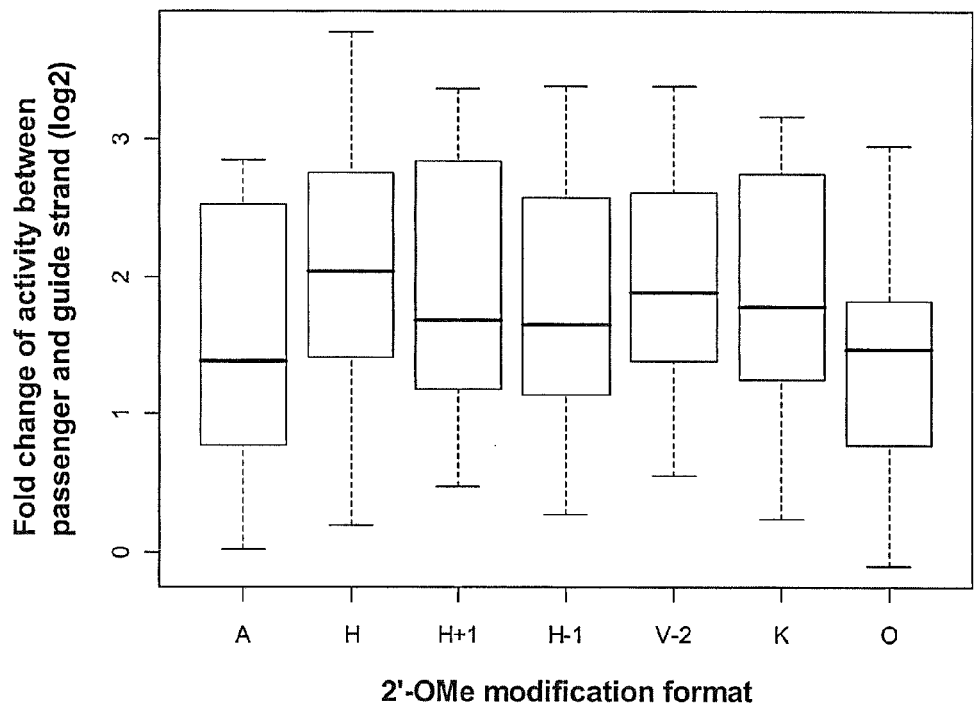

FIG. 13A-1 provides the difference in activity between the passenger strand and guide strand calculated as P−G with P and G defined as for FIG. 4B and FIG. 4C for siRNAs having unmodified Format A and modification Formats H, H+1, H−1, V−2, K and O where the modification is 2'-O-methyl modified nucleotides. Wilcoxon-test (paired) results comparing each modified format to the unmodified format are as follows: Format H, 0.00001574; Format H+1, 0.001091; Format H−1, 0.001918; Format V−2, 0.0002131; Format K, 0.0003619; Format O, 0.406.

FIG. 13A-2 provides the fold change of activity between the passenger strand and the guide strand for the siRNAs of FIG. 13A-1. Wilcoxon-test (paired) results comparing each modified format to the unmodified format are as follows: Format H, 0.00001574; Format H+1, 0.007443; Format H−1, 0.02514; Format V−2, 0.0001464; Format K, 0.0003619; Format O, 0.5446.

Figure 13B:
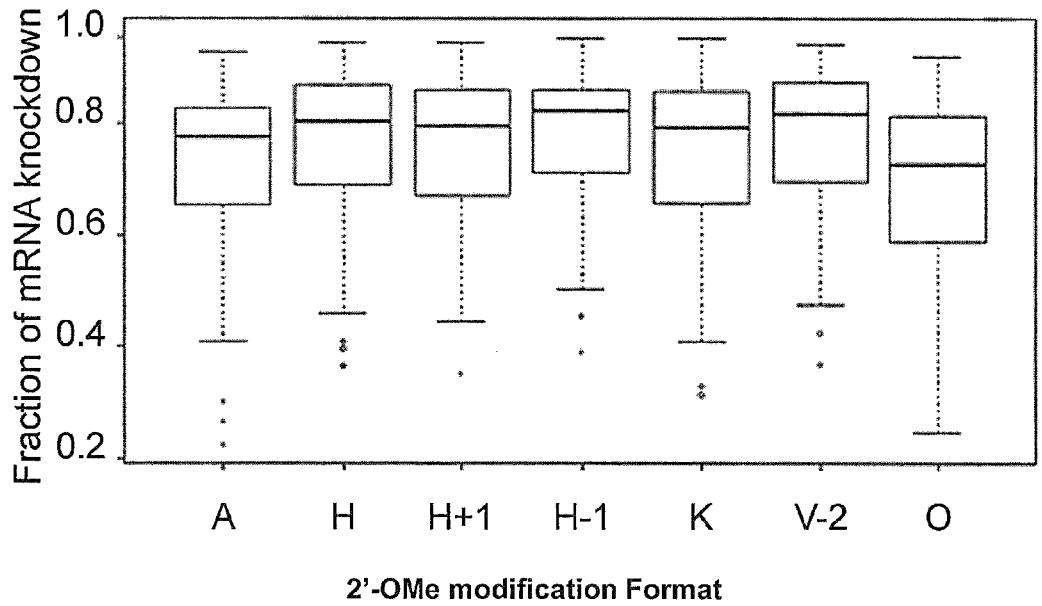

FIG. 13B provides knockdown activity data for endogenous targets for siRNAs having unmodified Format A and modification Formats H, H+1, H−1, K, V−2, and O where the modification is 2'-O-methyl modified nucleotides. Wilcoxon-test (paired) results comparing each modified format to the unmodified format are as follows: Format H, 3.47E-06; Format H+1, 0.001957517; Format H−1, 8.79E-09; Format K, 0.005446013; Format V−2, 1.95E-09; and Format O, 0.9972392.

Figure 13C:
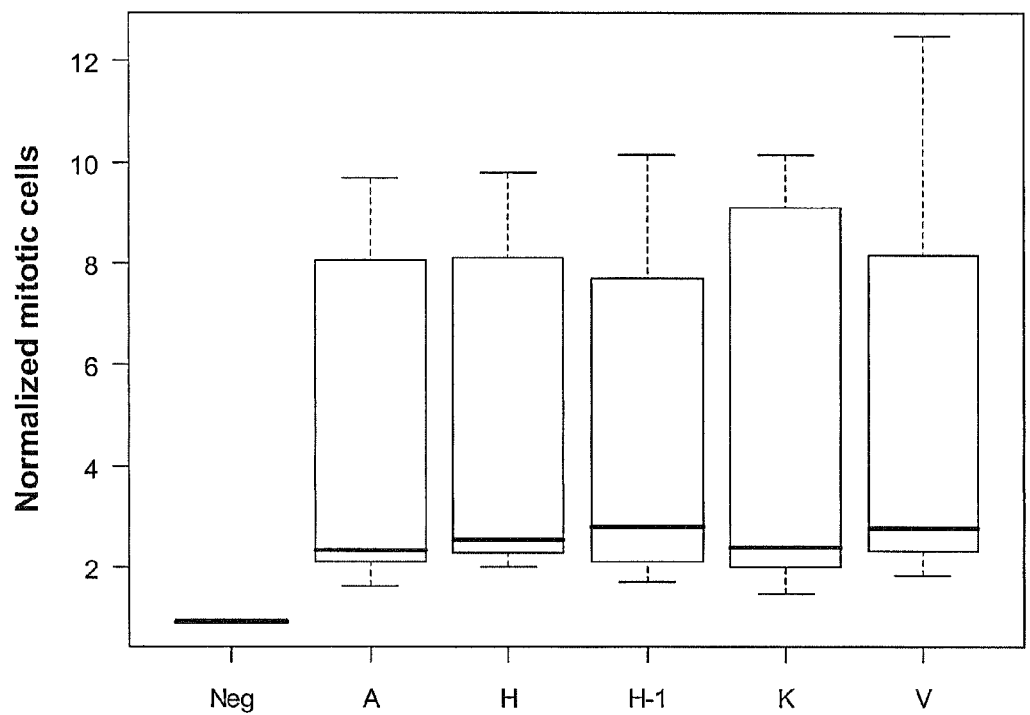

FIG. 13C provides a box plot of normalized mitotic cells resulting from silencing by siRNA having unmodified Format A and for modification Formats H, H−1, K and V having 2'-O-methyl modified nucleotides for a set of gene targets, the knockdown of which is expected to increase mitosis as described by Example 6. Wilcoxon-test (paired) results comparing each modified format to the unmodified format are as follows: Format H, 0.1953; Format H−1, 0.6406; Format V, 0.1953; Format K, 0.6406.

Figure 13D:
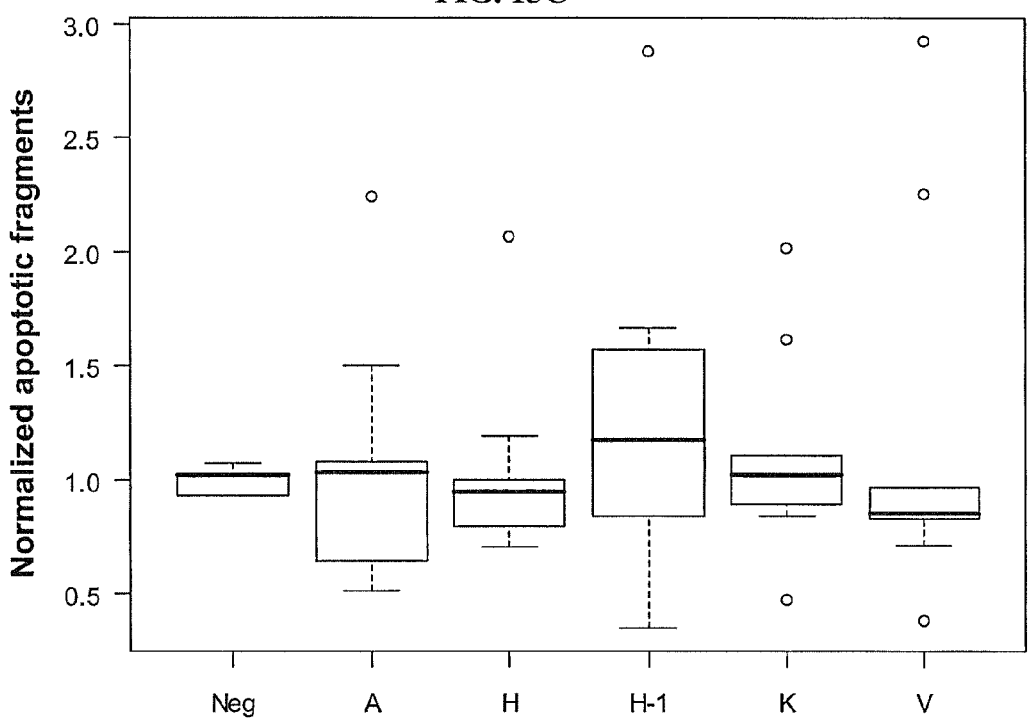

FIG. 13D provides a box plot of normalized apoptotic fragments resulting from silencing by siRNAs having unmodified Format A and for modification Formats H, H−1, V and K having 2'-O-methyl modified nucleotides for a set of gene targets, the knockdown of which is expected to have no effect on apoptosis as described by Example 6. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has greater distribution of data as compared to the Neg control. Wilcoxon-test (paired) results comparing the unmodified Format A to each modification format are: Format H, 0.9102; Format H−1, 0.25; Format V, 0.6523; Format K, 0.7344.

Figure 14A:
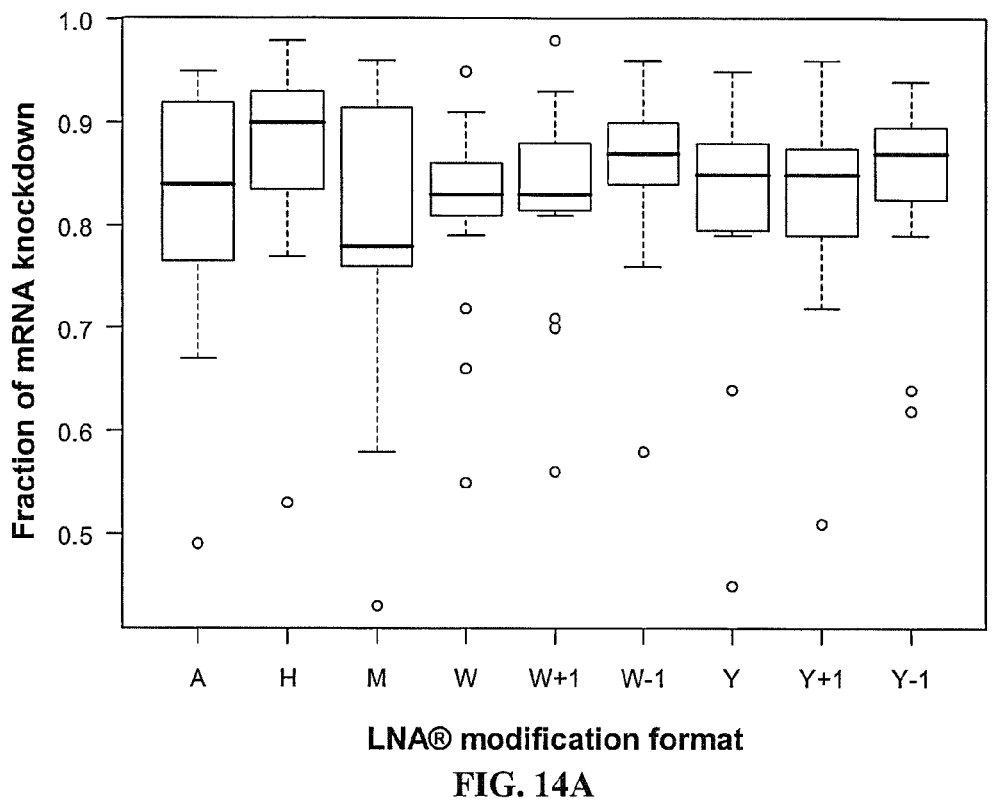

FIG. 14A provides a box plot of mRNA knockdown activity for endogenous targets for siRNAs having unmodified Format A and for LNA® modification Formats H, M, W, W+1, W−1, Y, Y+1, and Y−1. Wilcoxon-test (paired) statistical significance calculations comparing the unmodified Format A to each modification format are: Format H, 0.005302; Format M, 0.02475; Format W, 1; Format W+1, 0.8423; Format W−1, 0.5096; Format Y, 0.932; Format Y+1, 0.887; Format Y−1, 0.5891.

Figure 14B:
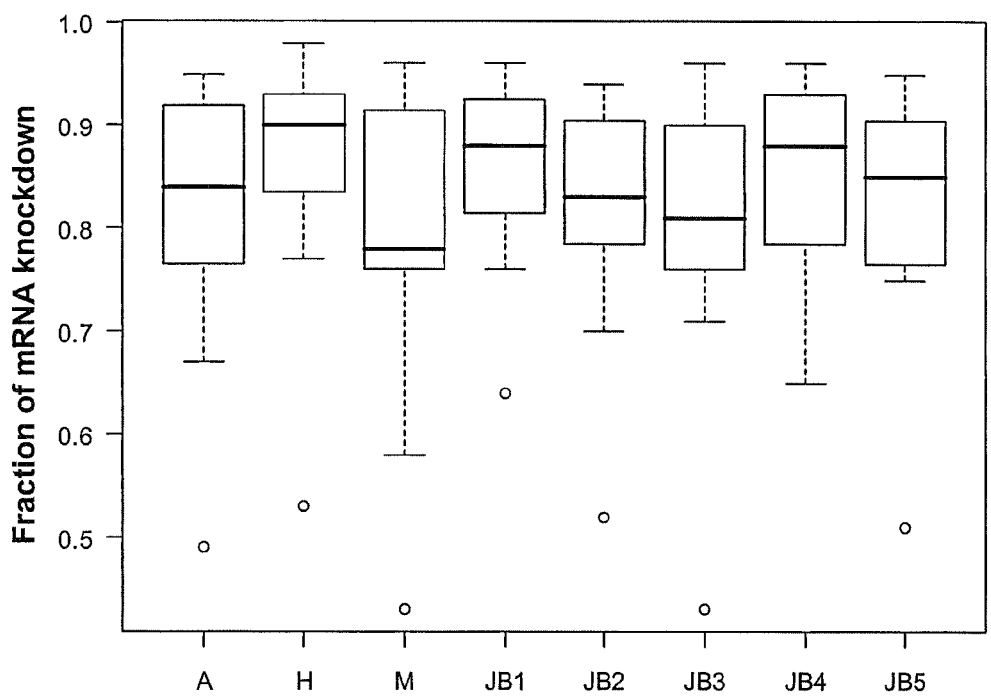

FIG. 14B provides a box plot of mRNA knockdown activity for endogenous targets for siRNAs having unmodified Format A and for LNA® modification Formats H, M, JB1, JB2, JB3, JB4, and JB5. Wilcoxon-test (paired) statistical significance calculations comparing the unmodified Format A to each modification format are: Format H, 0.005302; Format M, 0.02475; Format JB1, 0.009613; Format JB2, 0.7259; Format JB3, 0.4213; Format JB4, 0.04904; Format JB5, 0.972.

FIG. 15A-FIG. 15D provide data on the impact of siRNAs having unmodified Format A and for LNA® modification Formats H, M, W, W+1, W−1, Y, Y+1, and Y−1 on on-target and off-target phenotypes in cell biology studies. See Example 6.

Figure 15A:
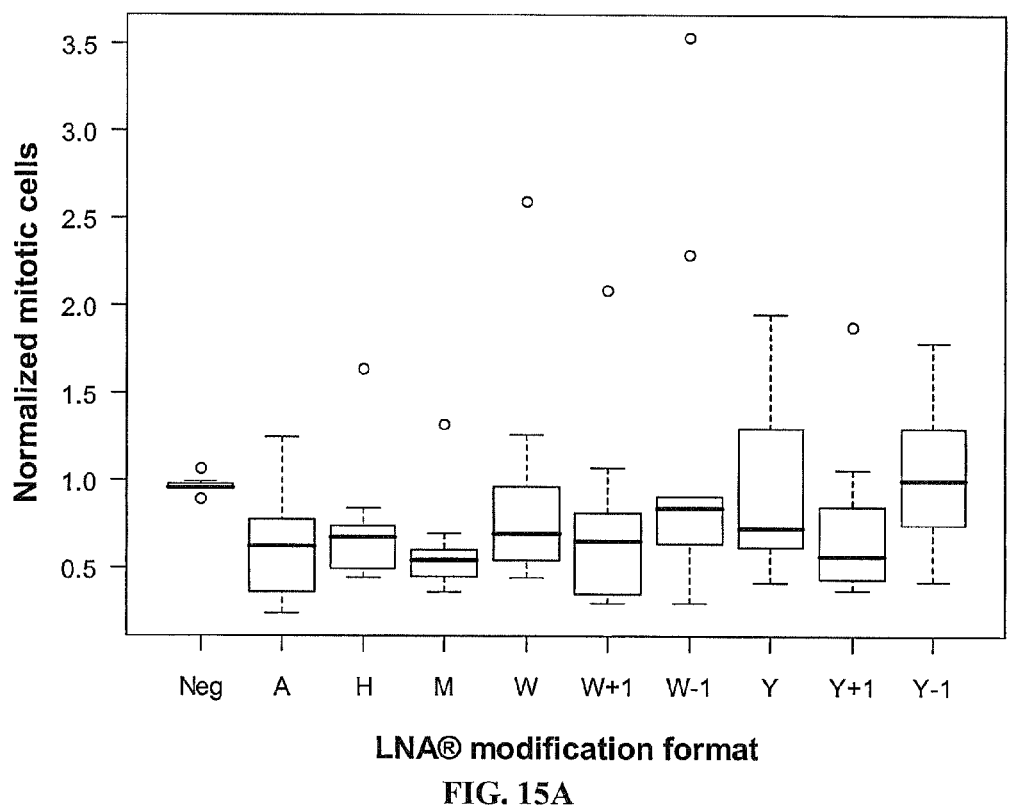

FIG. 15A provides a box plot of normalized mitotic cells as described in Example 6 for a set of gene targets, knockdown of which is expected to decrease mitosis as described by Example 6. The negative control (Neg) is a scrambled non-targeting siRNA for which mitosis quantitation is normalized to a value of 1.0. Wilcoxon-test (paired) results comparing each modified format to the unmodified siRNA format are as follows: Format H, 0.4961; Format M, 1; Format W, 0.01953; Format W+1, 0.5703; Format W−1, 0.07422; Format Y, 0.03906; Format Y+1, 0.4961; Format Y−1, 0.09766.

Figure 15B:
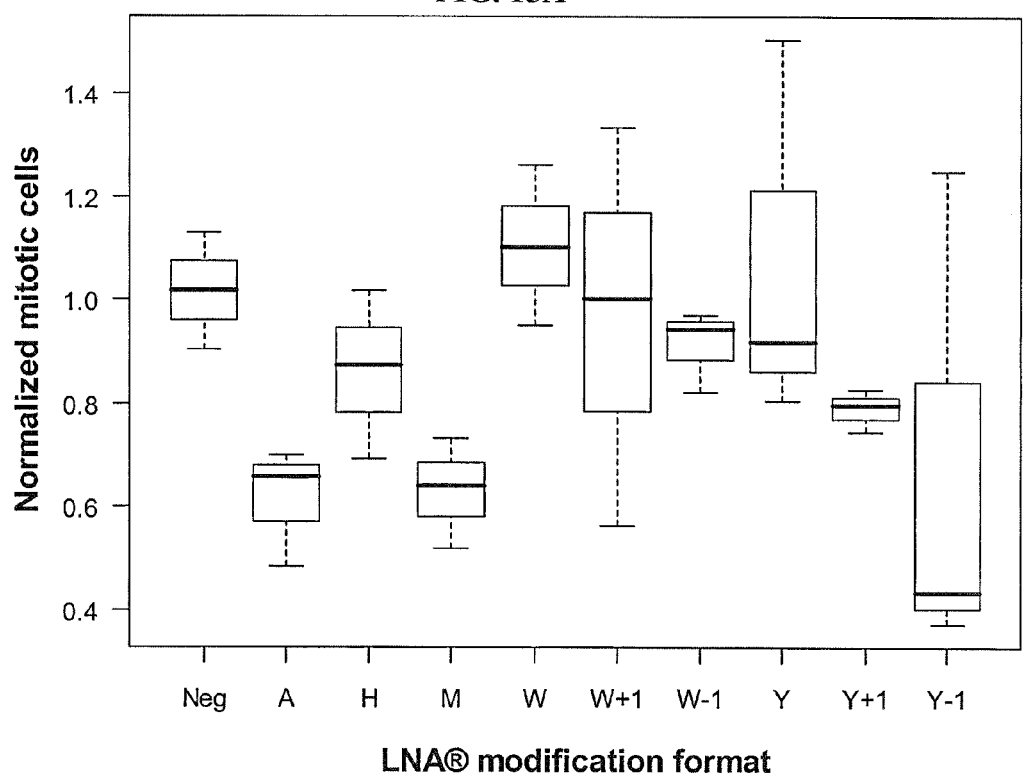

FIG. 15B provides a box plot as for FIG. 15A for a set of gene targets, knockdown of which is not expected to affect mitosis. However, siRNAs that have empirically demonstrated mitosis off-target effects were specifically chosen for study to determine if such siRNAs, when modification-formatted, would eliminate or reduce the off-target effects. That the siRNAs have off-target effects is evidenced by the box plot for unmodified Format A which has a median value of about 0.7 as compared to the Neg control. Wilcoxon-test (paired) statistical significance calculations comparing the unmodified Format A control to each modification format are: Format H, 0.5; Format M, 0.75; Format W, 0.25; Format W+1, 0.25; Format W−1, 0.25; Format Y, 0.25; Format Y+1, 0.25; Format Y−1, 1.

Figure 15C:
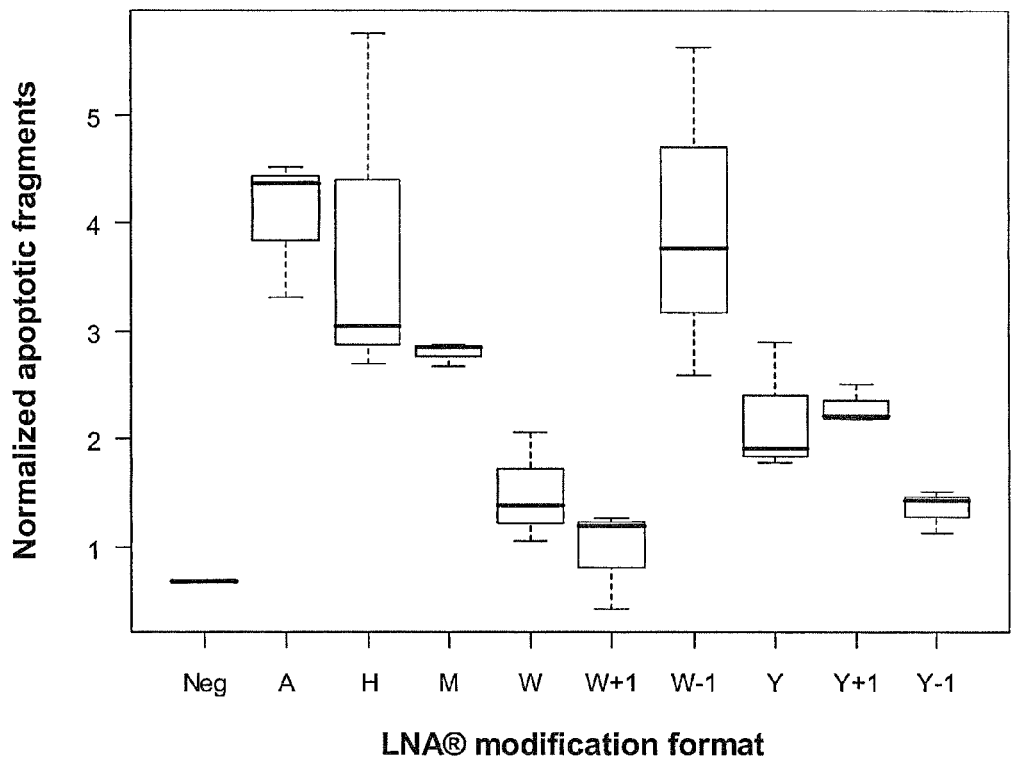

FIG. 15C provides a box plot of normalized apoptotic fragments for a set of gene targets, knockdown of which is expected to increase apoptosis as described in Example 6. Wilcoxon-test (paired) results comparing each modified format to the unmodified siRNA format are as follows: Format H, 0.75; Format M, 0.25; Format W, 0.25; Format W−1, 1; Format W+1, 0.25; Format Y, 0.25; Format Y−1, 0.25; Format Y+1, 0.25.

Figure 15D:
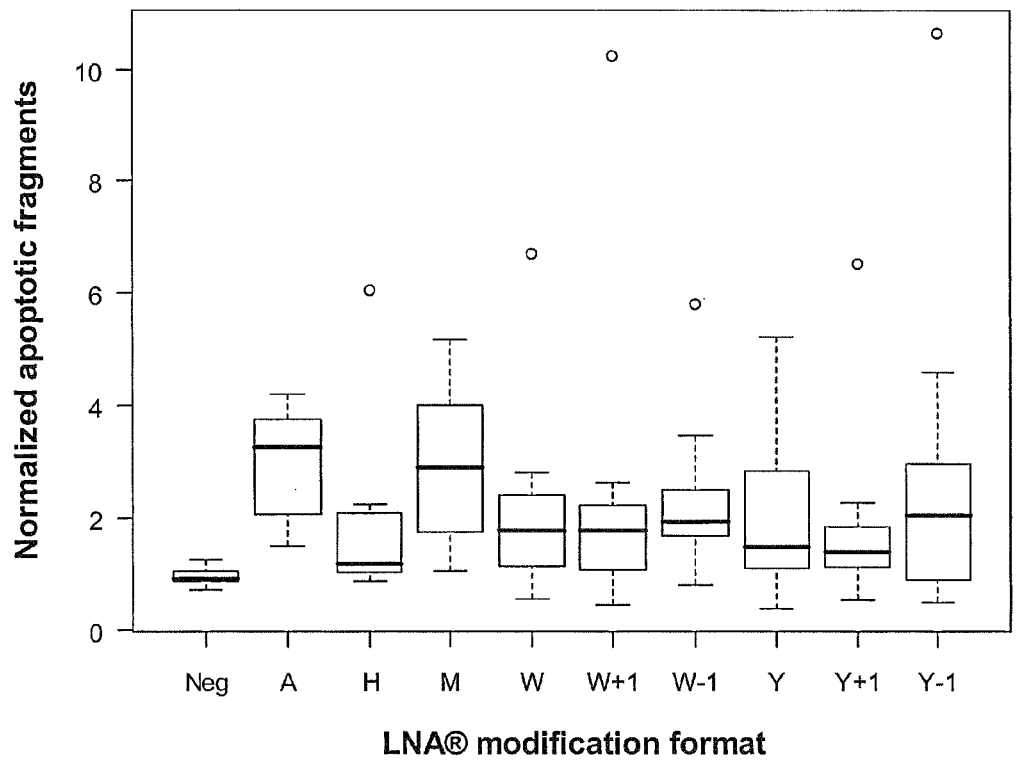

FIG. 15D provides a box plot as for FIG. 15C for a subset of gene targets, knockdown of which is not expected to have an effect on apoptosis. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has a median value of greater than 3.5 and greater distribution of data as compared to the Neg control. Wilcoxon-test (paired) results comparing each modified format to the unmodified siRNA format are as follows: Format H, 0.01221; Format M, 0.8501; Format W, 0.07715; Format W+1, 0.06396; Format W−1, 0.1763; Format Y, 0.03418; Format Y+1, 0.021; Format Y−1, 0.2036.

FIG. 16A-FIG. 16D provide data on the impact of siRNAs having unmodified Format A and for LNA® modification Formats H, M, JB1, JB2, JB3, JB4 and JB5 on on-target and off-target phenotypes in cell biology studies. See Example 6.

Figure 16A:
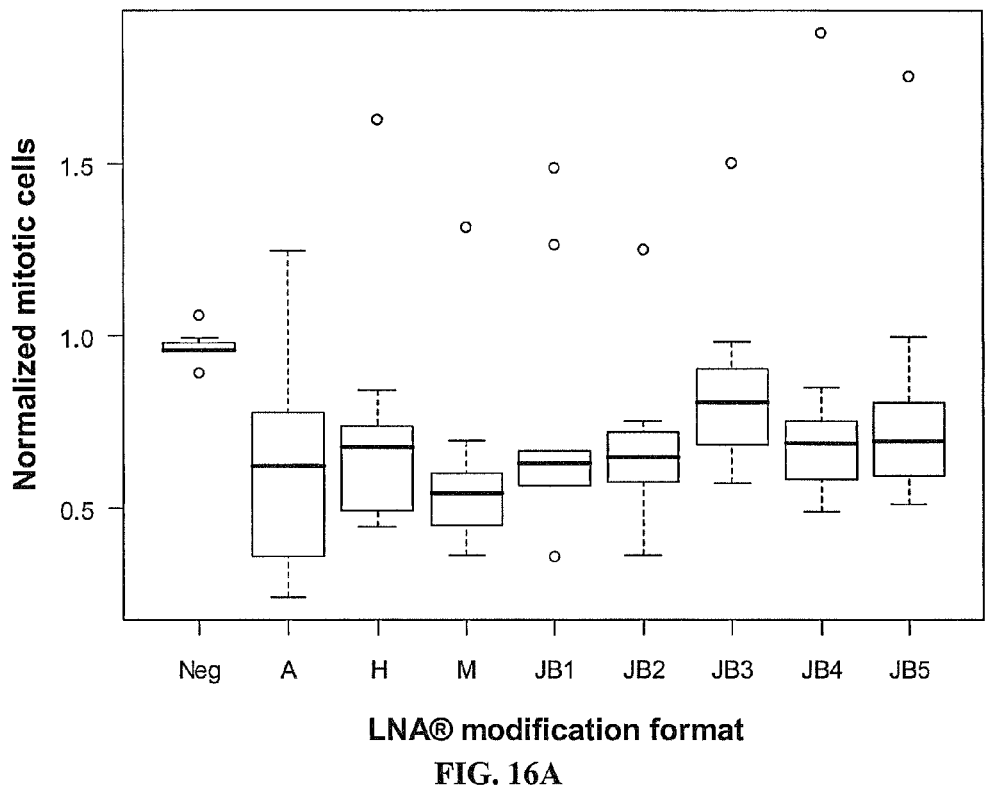

FIG. 16A provides a box plot of normalized mitotic cells for a set of gene targets, knockdown of which is expected to decrease mitosis. Wilcoxon-test (paired) results comparing each modified format to the unmodified siRNA format are as follows: Format H, 0.4961; Format M, 1; Format JB1, 0.3594; Format JB2, 0.6523; Format JB3, 0.02734; Format JB4, 0.1641; Format JB5, 0.2031.

Figure 16B:
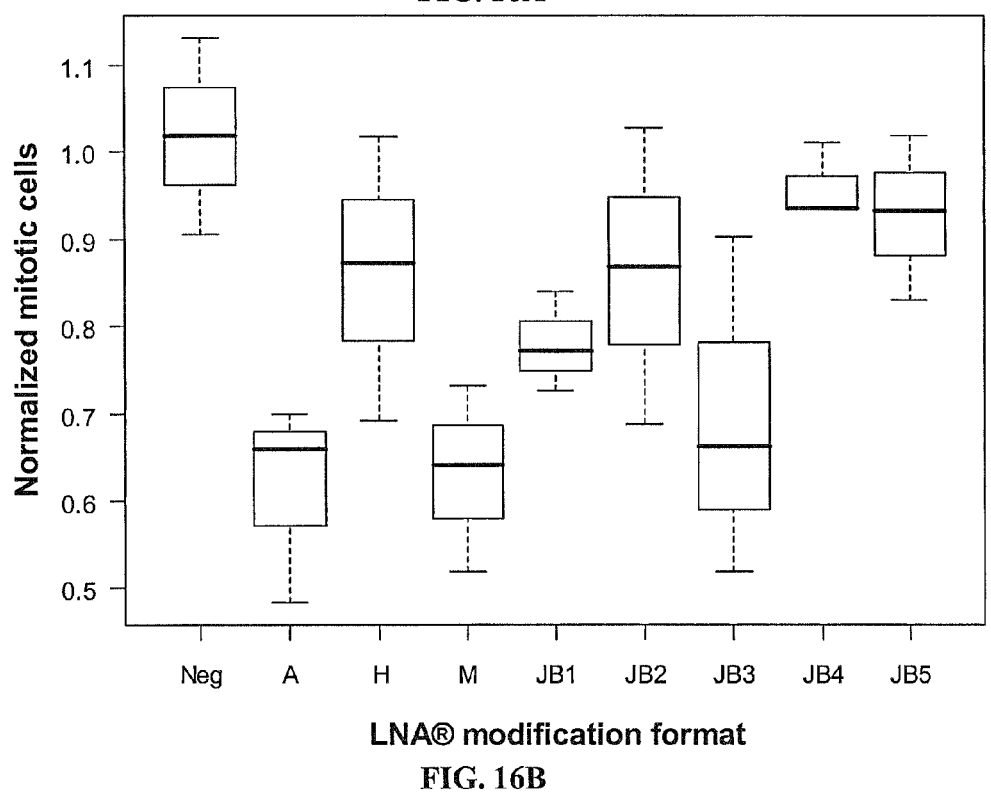

FIG. 16B provides a box plot as for FIG. 16A for a set of gene targets, knockdown of which is not expected to affect mitosis. However, siRNAs that have empirically demonstrated mitosis off-target effects were specifically chosen for study to determine if such siRNAs, when modification-formatted, would eliminate or reduce the off-target effects. That the siRNAs have off-target effects is evidenced by the box plot for unmodified Format A which has a median value of about 0.65 thereby displaying a decrease in mitosis as compared to the Neg control. Wilcoxon-test (paired) results comparing the unmodified Format A control to each modification format are: Format H, 0.5; Format M, 0.75; Format JB1, 0.25; Format JB2, 0.25; Format JB3, 0.75; Format JB4, 0.25; Format JB5, 0.25.

Figure 16C:
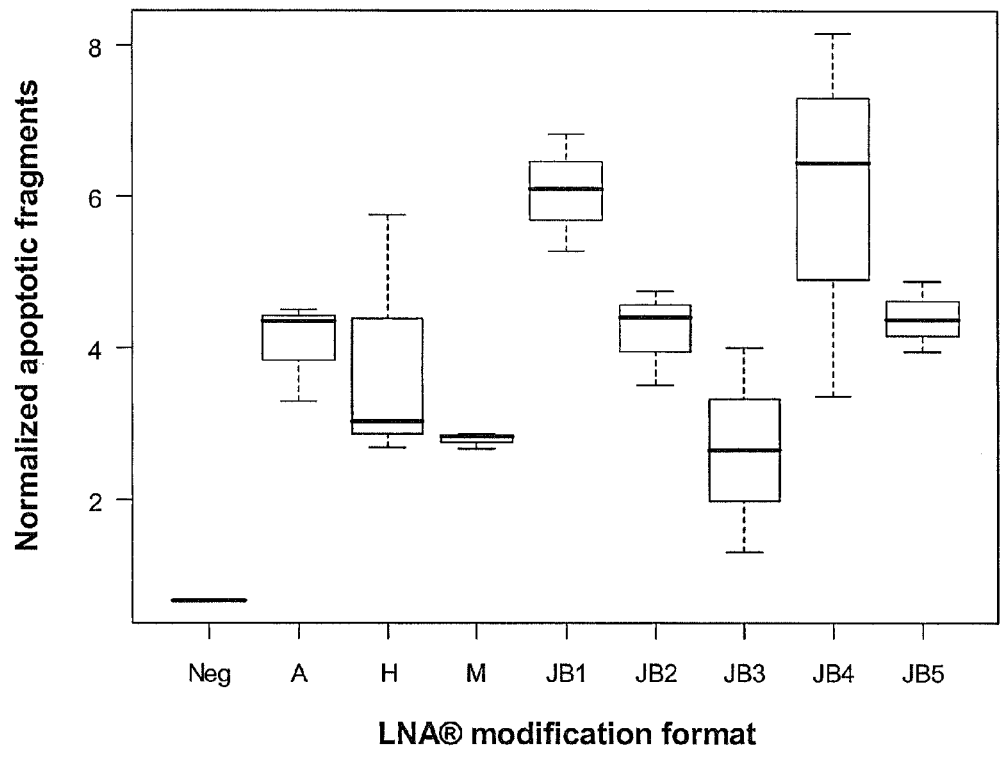

FIG. 16C provides a box plot of normalized apoptotic fragments resulting from silencing for a set of gene targets, the knockdown of which is expected to increase apoptosis as described in Example 6. Wilcoxon-test (paired) results comparing each modified format to the unmodified siRNA format are as follows: Format H, 0.75; Format M, 0.25; Format JB1, 0.25; Format JB2, 0.25; Format JB3, 0.25; Format JB4, 0.5; Format JB5, 0.75.

Figure 16D:
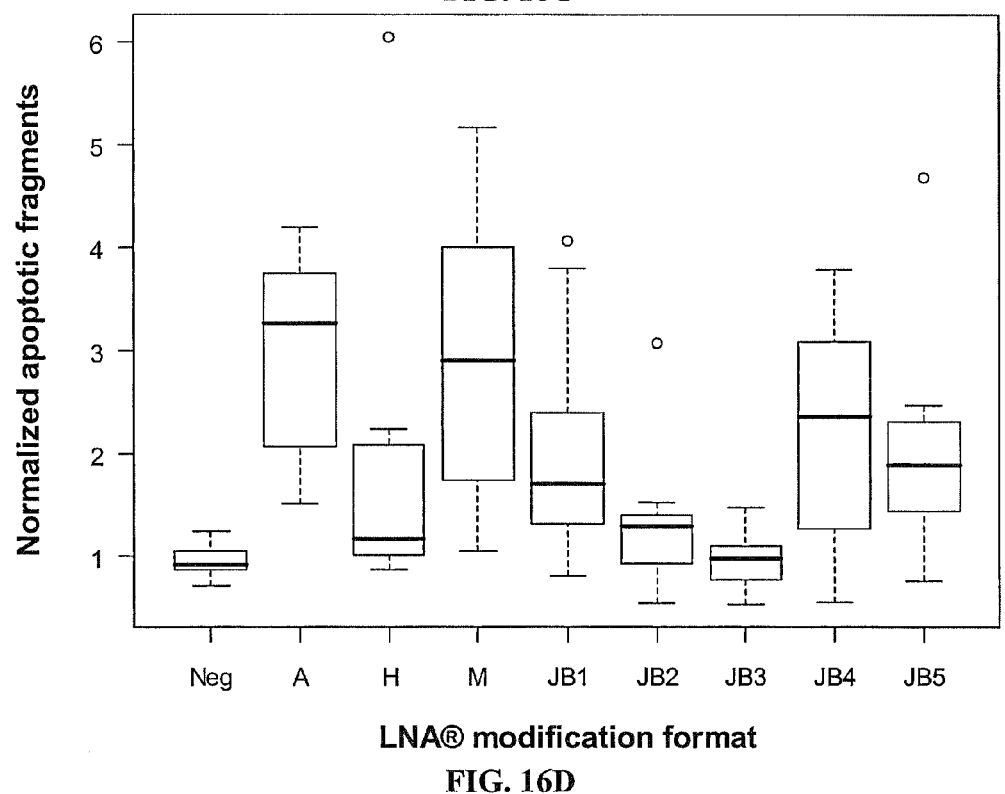

FIG. 16D provides a box plot as for FIG. 16C for a set of gene targets, knockdown of which is not expected to have an effect on apoptosis. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median value of greater than 3 and greater distribution of data as compared to the Neg control treated samples. Wilcoxon-test (paired) results comparing each modified format to the unmodified siRNA format are as follows: Format H, 0.01221; Format M, 0.8501; Format JB1, 0.0009766; Format JB2, 0.0004883; Format JB3, 0.0004883; Format JB4, 0.003418; Format JB5, 0.003418.

Figure 17:
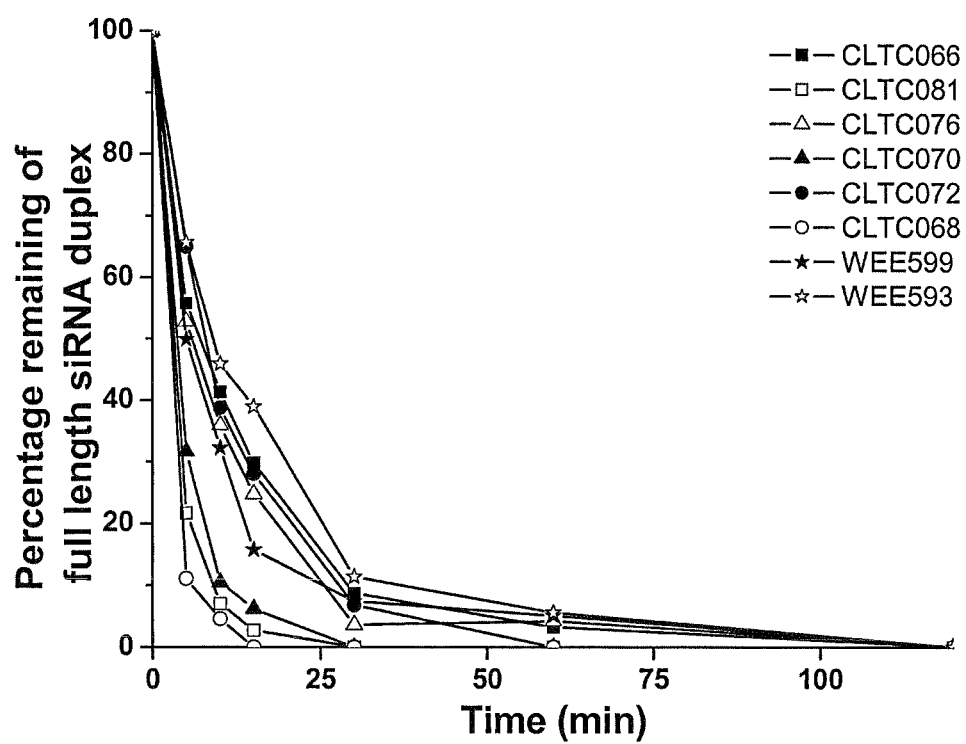

FIG. 17 provides an assay for serum stability as a function of time for unmodified siRNAs in 90% serum at 37° C. The percentage of the remaining full length siRNA duplex is shown for 8 different siRNAs at 0, 5, 10, 15, 30, 60, 120 minutes incubation.

Figure 18A:
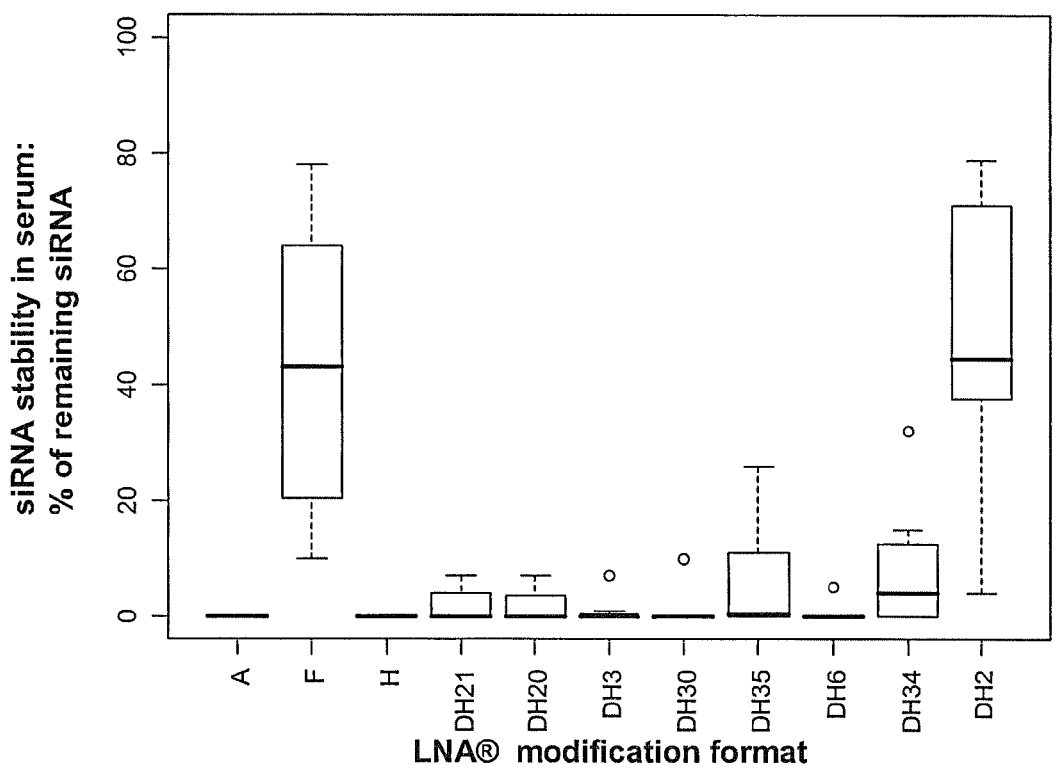

FIG. 18A provides a box plot of % of siRNAs that remain full length when treated with 90% serum under conditions described in Example 7. Data are provided for the unmodified Format A siRNA, siRNA modification Format F which format is cited as siLNA5 by Elmen et al. (*Nucleic Acids Research* 33:1, 439-447, 2005) and is used herein as a reference control for stability, and siRNA having modification Formats H, DH21, DH20, DH3, DH30, DH35, DH6, DH34, and DH2 where the modifications are LNA® residues. Wilcoxon-test (paired) results comparing Format F to each modification format are: Format H, 0.007813; Format DH21, 0.007813; Format DH20, 0.007813; Format DH3, 0.007813; Format DH30, 0.007813; Format DH35, 0.01563; Format DH6, 0.007813; Format DH34, 0.02488; Format DH2, 0.2049.

Figure 18B:
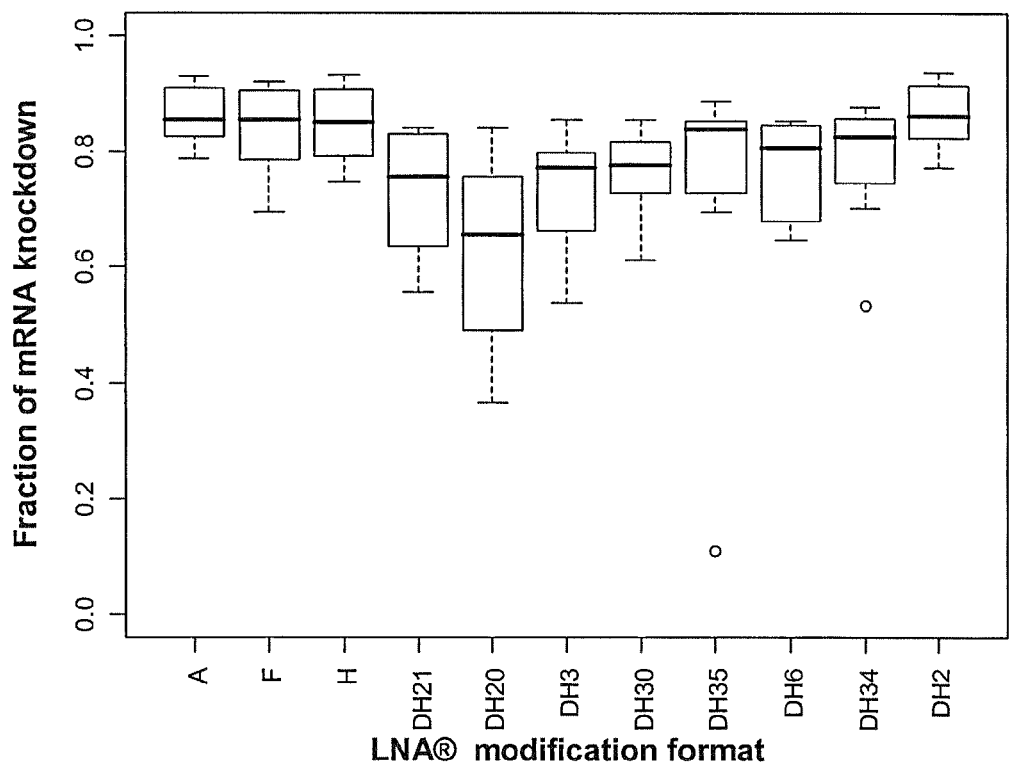

FIG. 18B provides a box plot of the fraction of mRNA knockdown, relative to Neg control siRNA, by LNA® modified siRNAs in Formats A, F, H, DH21, DH20, DH3, DH30, DH35, DH6, DH34, DH2 as described by Example 7. Wilcoxon-test (paired) statistical significance calculations comparing the unmodified Format A control to each modification format are: Format F, 0.05469; Format H, 0.3828; Format DH21, 0.007813; Format DH20, 0.007813; Format DH3, 0.007813; Format DH30, 0.007813; Format DH35, 0.01563; Format DH6, 0.007813; Format DH34, 0.03906; Format DH2, 0.6406.

Figure 19A:
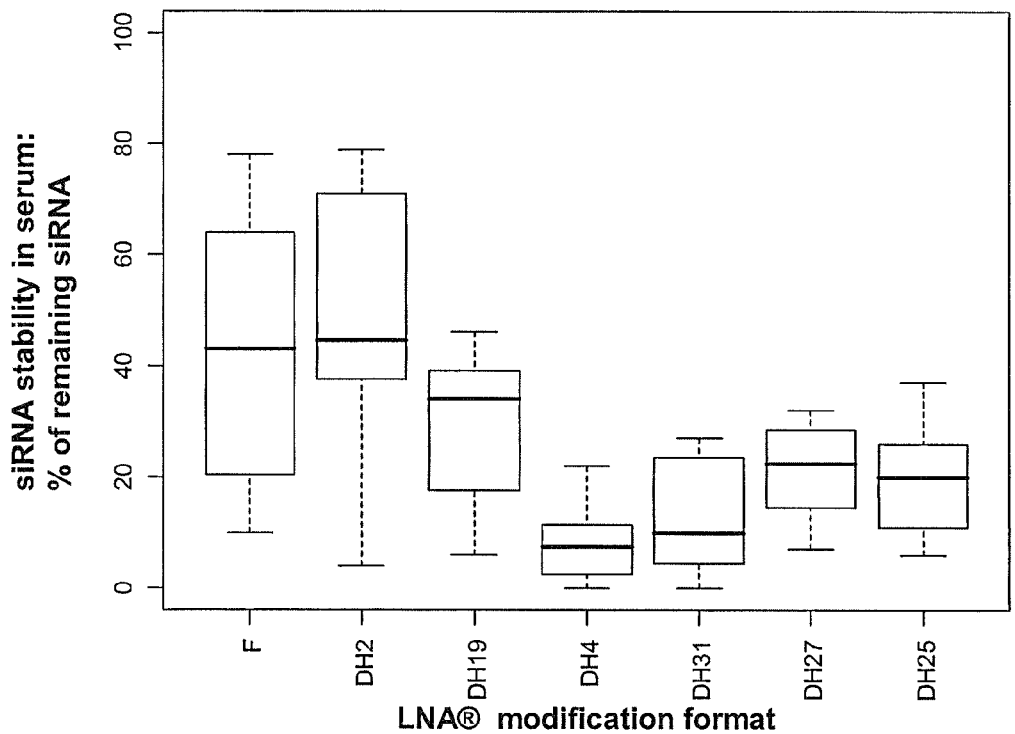

FIG. 19A provides a box plot of % of siRNAs that remain full length when treated with 90% serum under conditions described in Example 7. Data are provided for modification Formats F, DH2, DH19, DH4, DH31, DH27, and DH25 where the modifications are LNA® residues. Wilcoxon-test (paired) statistical significance calculations comparing Format F to each modification format are: Format DH2, 0.2049; Format DH19, 0.1953; Format DH4, 0.02249; Format DH31, 0.01563; Format DH27, 0.1094; Format DH25, 0.1094.

Figure 19B:
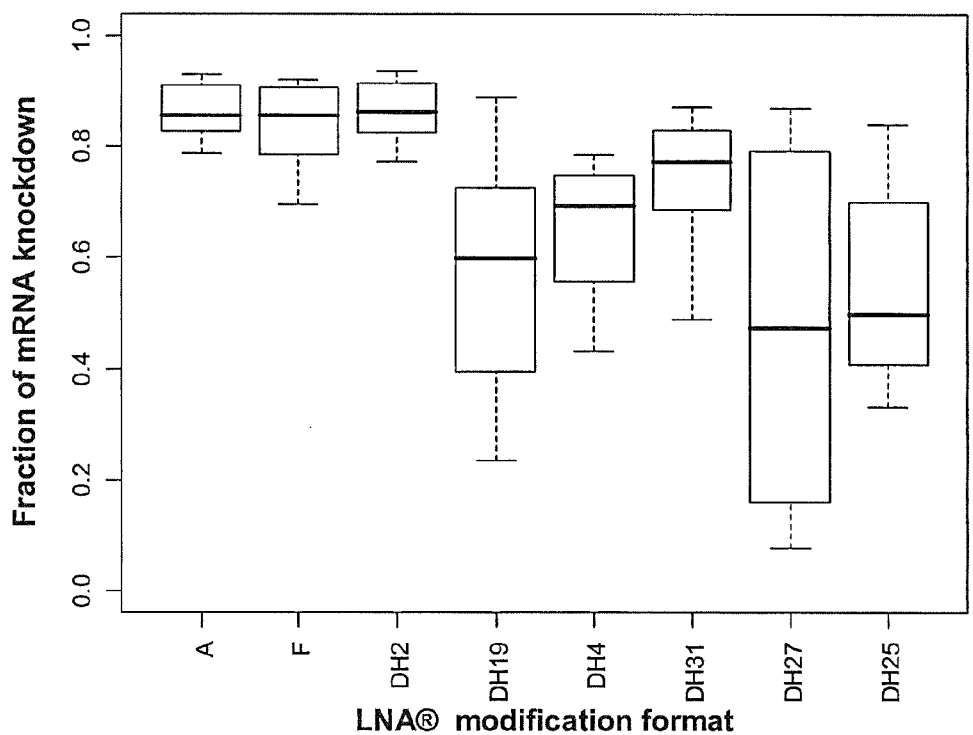

FIG. 19B provides a box plot of the fraction of mRNA knockdown, relative to Neg control siRNA, by LNA® modified siRNA in Formats F, DH2, DH19, DH4, DH31, DH27, and DH25 as described by Example 7. Wilcoxon-test (paired) statistical significance calculations comparing the unmodified Format A control to each modification format are: Format F, 0.05469; Format DH2, 0.6406; Format DH19, 0.01563; Format DH4, 0.007813; Format DH31, 0.01563; Format DH27, 0.01563; Format DH25, 0.007813.

Figure 20A:
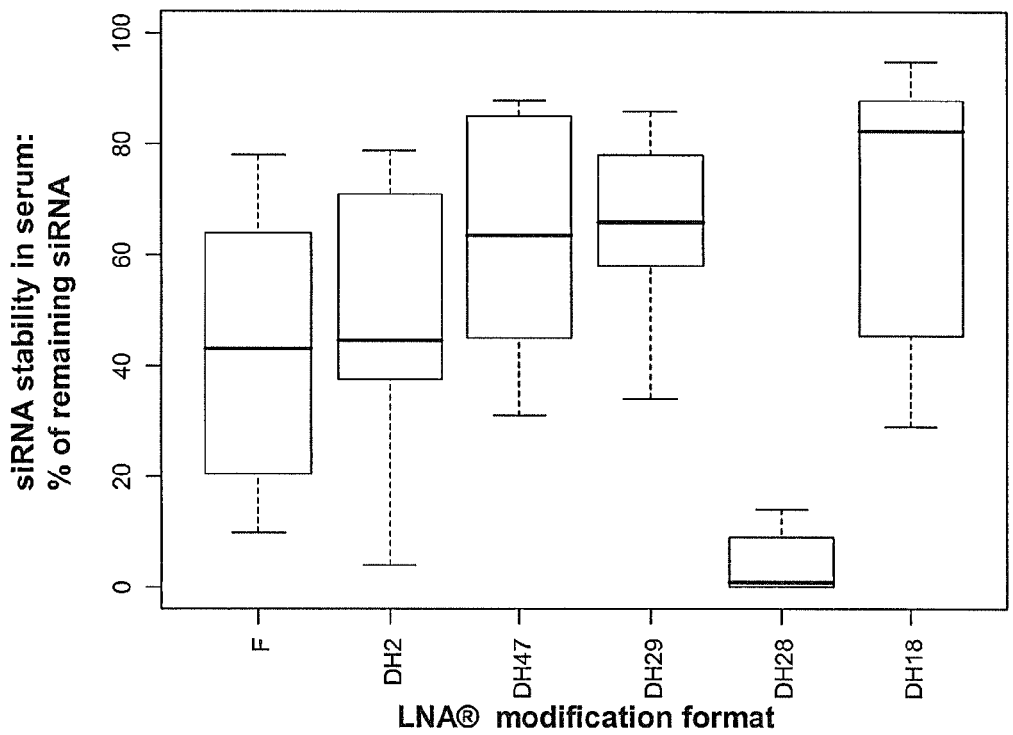

FIG. 20A provides a box plot of % of siRNAs that remain full length when treated with serum under conditions described in Example 7. Data are provided for modification Formats F, DH2, DH47, DH29, DH28 and DH18 where the modifications are LNA® residues. Wilcoxon-test (paired) statistical significance calculations comparing Format F to each modification format are: Format DH2, 0.2049; Format DH47, 0.03906; Format DH29, 0.07813; Format DH28, 0.01415; Format DH18, 0.06836.

Figure 20B:
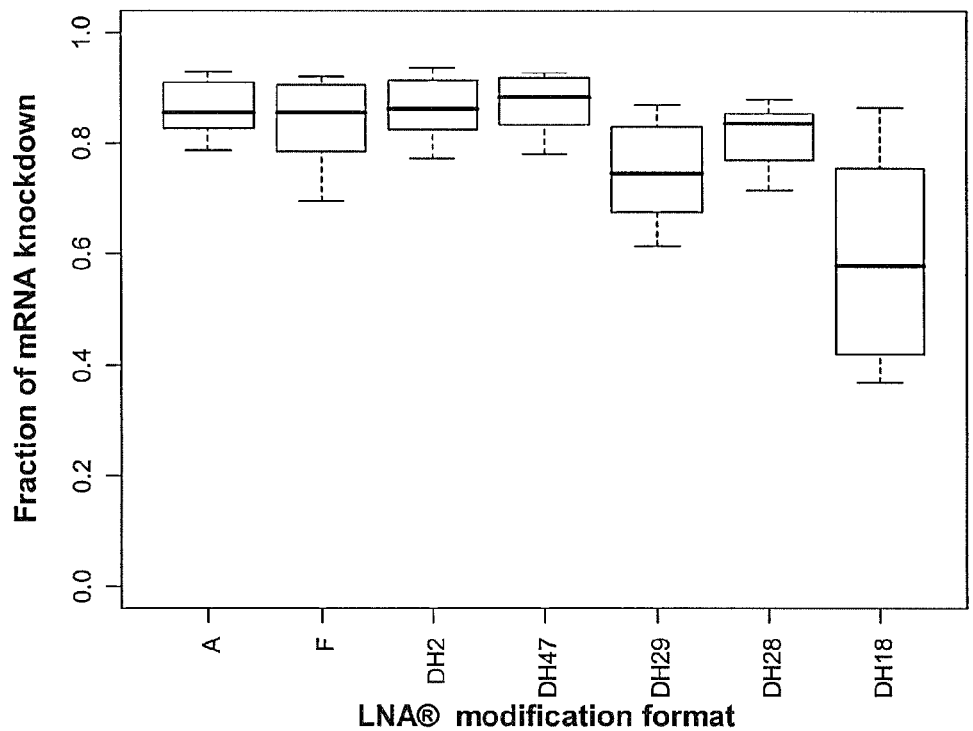

FIG. 20B provides a box plot of the fraction of mRNA knockdown, relative to Neg control siRNA, by LNA® modified siRNA in Formats F, DH2, DH47, DH29, DH28 and DH18 as described by Example 7. Wilcoxon-test (paired) statistical significance calculations comparing the unmodified Format A control to each modification format are: F, 0.05469; Format DH2, 0.6406; Format DH47, 0.3125; Format DH29, 0.02249; Format DH28, 0.01563; Format DH18, 0.01563.)

Figure 21A:
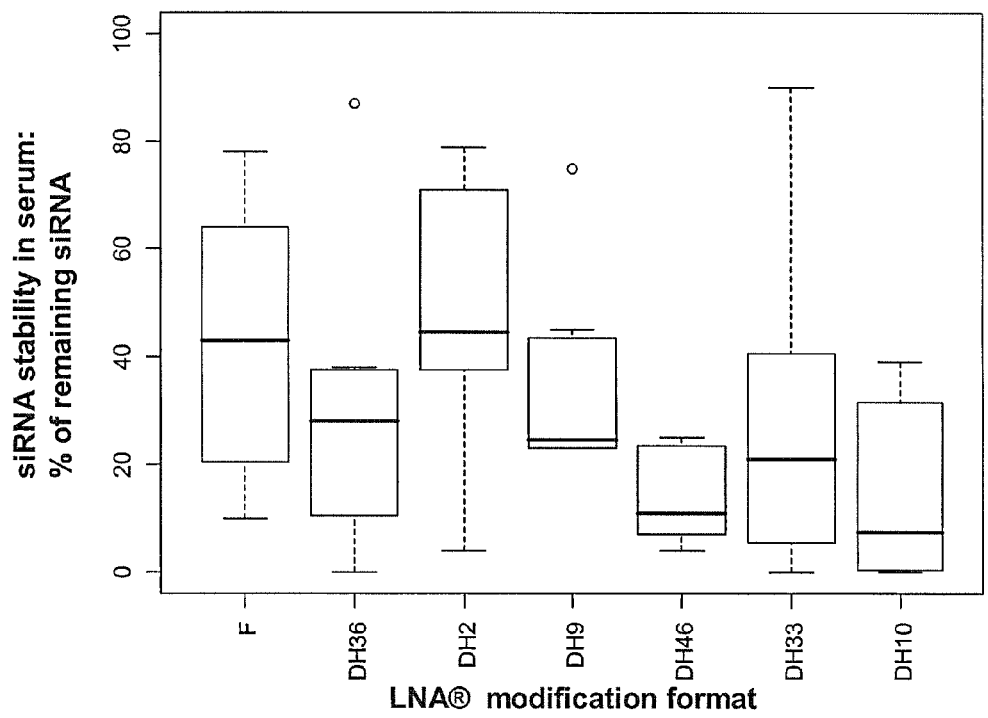

FIG. 21A provides a box plot of % of siRNAs that remain full length when treated with serum under conditions described in Example 7. Data are provided for modification Formats F, DH36, DH2, DH9, DH46, DH33 and DH10 where the modifications are LNA® residues. Wilcoxon-test (paired) statistical significance calculations comparing Format F to each modification format are: Format DH36, 0.1609; Format DH2, 0.2049; Format DH9, 0.5534; Format DH46, 0.02071; Format DH33, 0.1508; Format DH10, 0.05469.

Figure 21B:
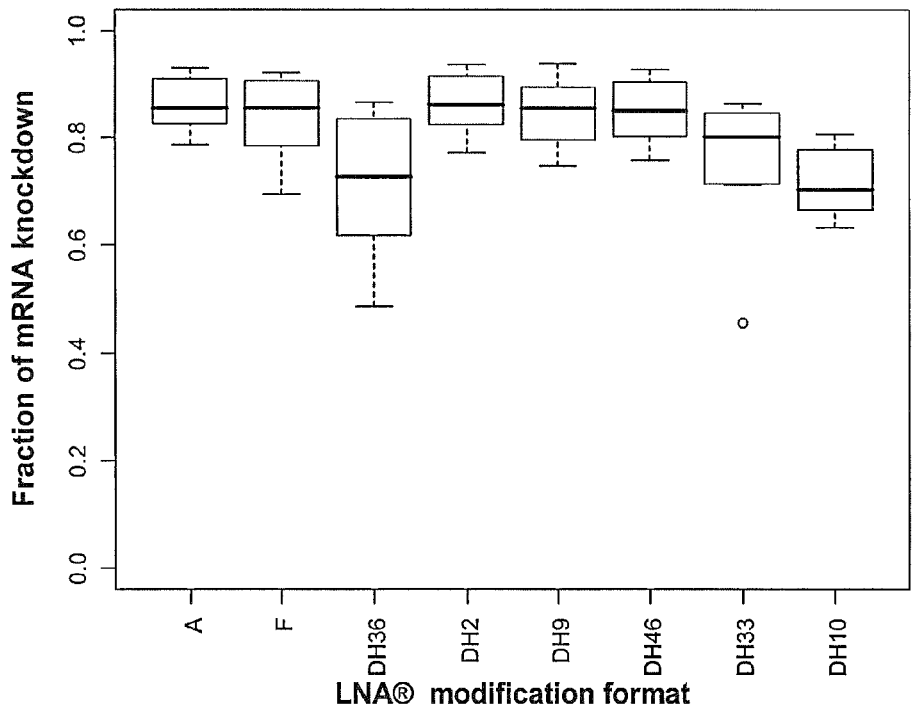

FIG. 21B provides a box plot of the fraction of mRNA knockdown, relative to Neg control siRNA, by LNA® modified siRNAs in Formats F, DH36, DH2, DH9, DH46, DH33 and DH10 as described by Example 7. Wilcoxon-test (paired) statistical significance calculations comparing unmodified Format A control to each modification format are: Format F, 0.05469; Format DH36, 0.01563; Format DH2, 0.6406; Format DH9, 0.1484; Format DH46, 0.1484; Format DH33, 0.007813; Format DH10, 0.007813.

Figure 22A:
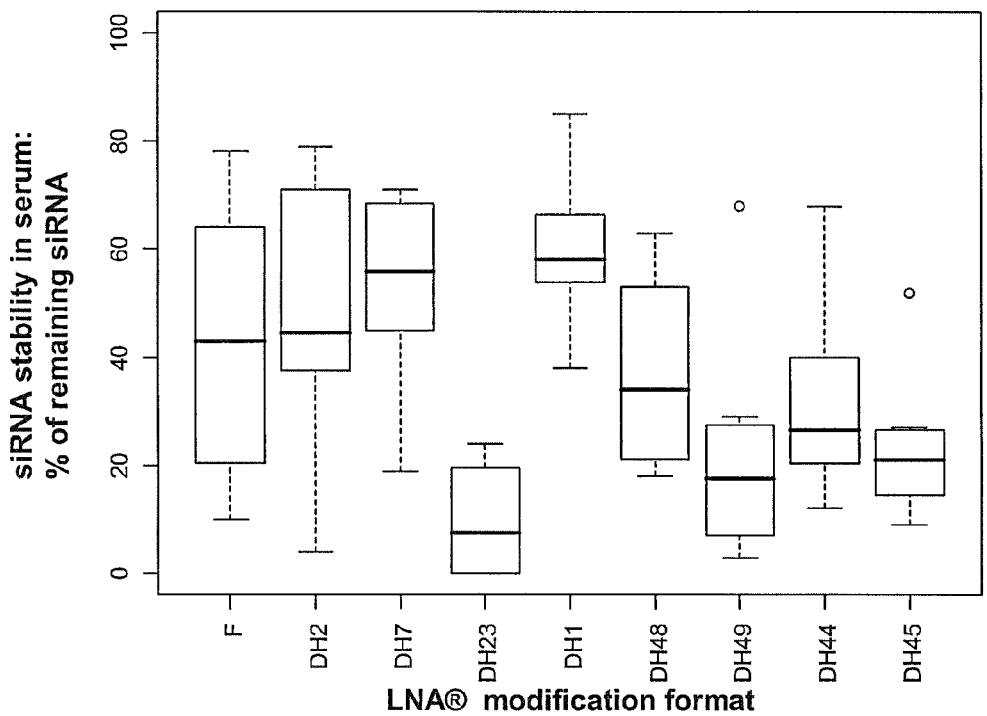

FIG. 22A provides a box plot of % of siRNAs that remain full length when treated with serum under conditions described in Example 7. Data are provided for modification Formats F, DH2, DH7, DH23, DH1, DH48, DH49, DH44 and DH45 where the modifications are LNA® residues. Wilcoxon-test (paired) statistical significance calculations comparing Format F to each modification format are: Format DH2, 0.2049; Format DH7, 0.3828; Format DH23, 0.03461; Format DH1, 0.1484; Format DH48, 0.6406; Format DH49, 0.1410; Format DH44, 0.3125; Format DH45, 0.1052.

Figure 22B:
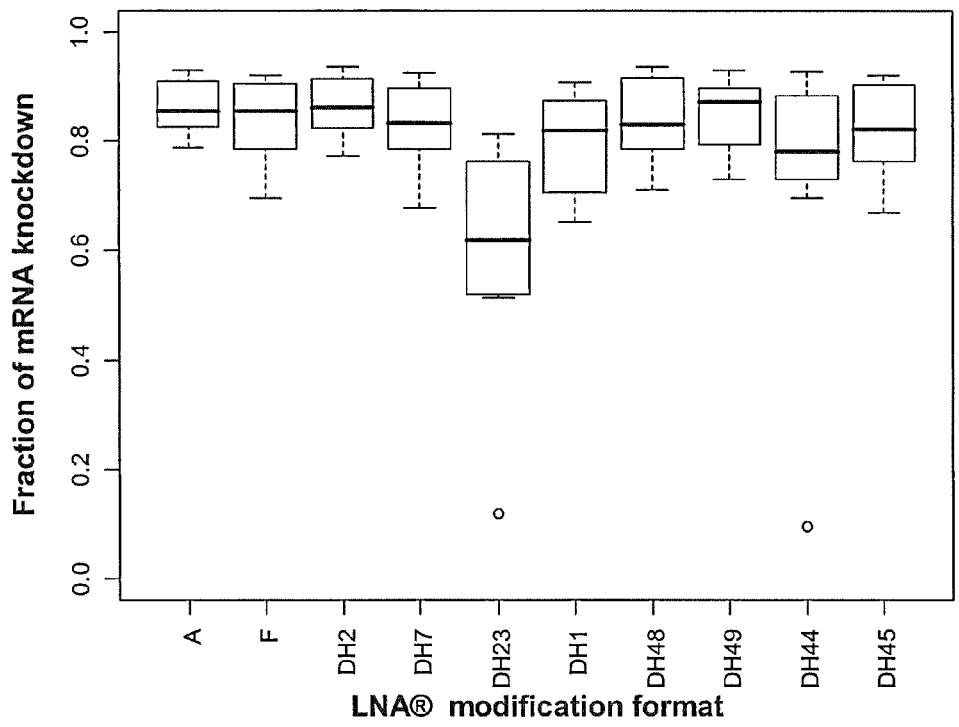

FIG. 22B provides a box plot of the fraction of mRNA knockdown, relative to Neg control siRNA, by LNA® modified siRNAs in Formats F, DH2, DH7, DH23, DH1, DH48, DH49, DH44 and DH45 as described by Example 7. Wilcoxon-test (paired) statistical significance calculations comparing unmodified Format A to each modification format are: Format F, 0.05469; Format DH2, 0.6406; Format DH7, 0.05469; Format DH23, 0.007813; Format DH1, 0.007813; Format DH48, 0.1953; Format DH49, 0.4609; Format DH44, 0.007813; Format DH45, 0.01563.

Figure 23A:
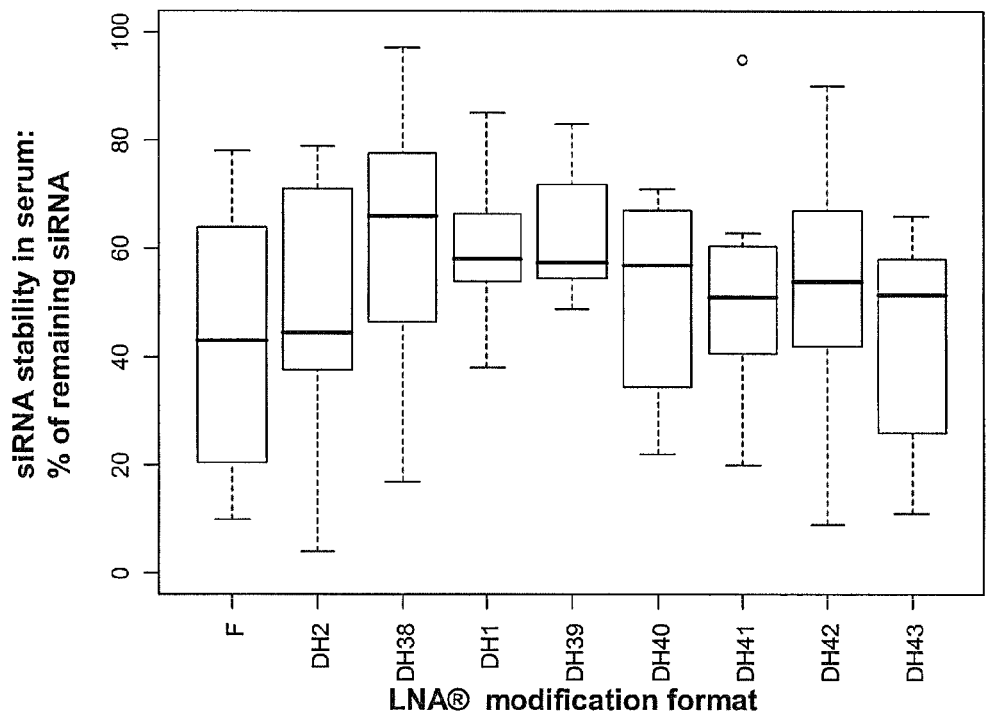

FIG. 23A provides a box plot of % of siRNAs that remain full length when treated with serum under conditions described in Example 7. Data are provided for modification Formats F, DH2, DH38, DH1, DH39, DH40, DH41, DH42 and DH43 where the modifications are LNA® residues. Wilcoxon-test (paired) statistical significance calculations comparing Format F to each modification format are: Format DH2, 0.2049; Format DH38, 0.04206; Format DH1, 0.1484; Format DH39, 0.07813; Format DH40, 0.2500; Format DH41, 0.2620; Format DH42, 0.1094; Format DH43, 0.3621.

Figure 23B:
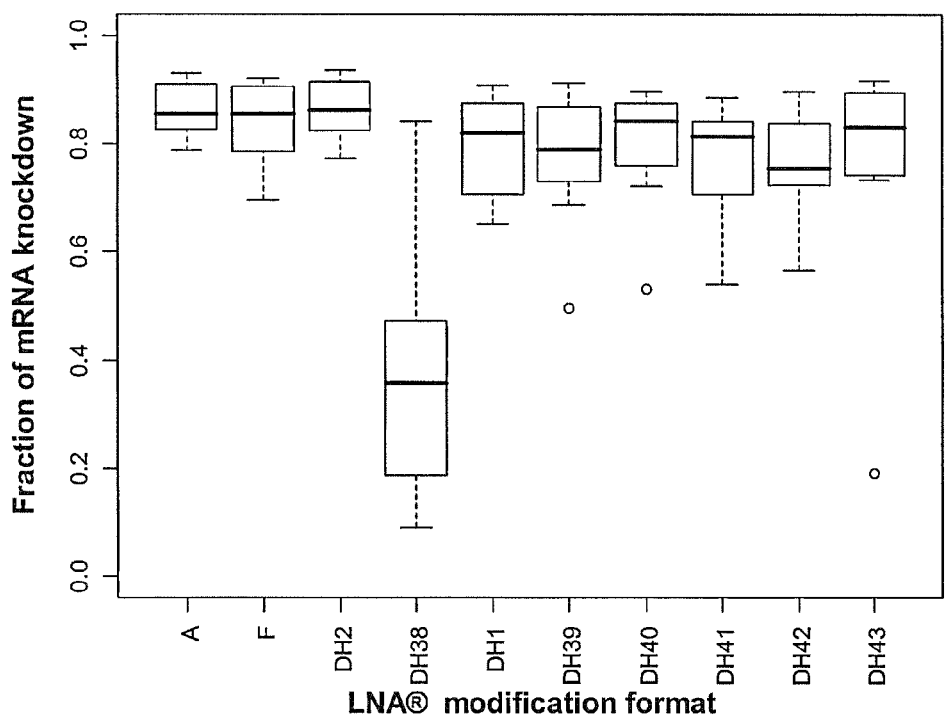

FIG. 23B provides a box plot of the fraction of mRNA knockdown, relative to Neg control siRNA, by LNA® modified siRNAs in Formats F, DH2, DH38, DH1, DH39, DH40, DH41, DH42 and DH43 as described by Example 7. Wilcoxon-test (paired) statistical significance calculations comparing unmodified Format A to each modification format are: Format F, 0.05469; Format DH2, 0.6406; Format DH38, 0.007813; Format DH1, 0.007813; Format DH39, 0.007813; Format DH40, 0.01563; Format DH41, 0.007813; Format DH42, 0.007813; Format DH43, 0.02344.

Figure 24:
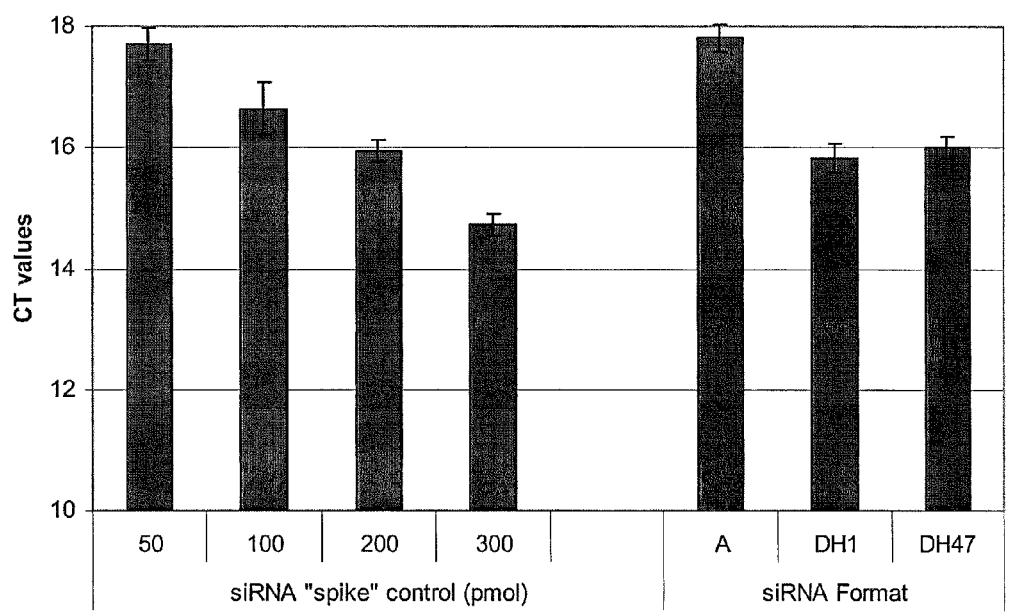

FIG. 24 provides quantification of in vivo presence of stabilized siRNAs. The amount of siRNA present in livers from spiked control animals is compared to the amount of siRNA present in livers from test animals injected with unmodified Format A siRNA and LNA® modification-formatted stabilized siRNAs having Format DH1 or Format DH47. CT is cycle threshold.

DESCRIPTION OF VARIOUS EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "at least one" means that more than one can be present. Also, the use of "comprise", "contain", and "include", or modifications of those root words, for example but not limited to, "comprises", "contained", and "including", are not intended to be limiting and means "including the following elements but not excluding others." The term "consists essentially of," or "consisting essentially of," as used herein, excludes other elements from having any essential significance to the combination. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context. The term "surrogate" as used herein means a product that is indicative of presence of another product. For example, an amplification product is a surrogate for a nucleic acid that has been amplified.

As used herein, "modification format," for a siRNA means a pattern of modified nucleotides and "other-than modified" nucleotides as exemplified by the patterns or formats set forth by FIG. 1A-FIG. 1K. Modified nucleotides are described below. "Other-than modified" means an unmodified nucleotide or a modified nucleotide having a modification other than the modification of the modified nucleotide in a particular format.

As used herein, "sequence-independent modification," means that modified nucleotides and modification formats provided by embodiments may be applied to any siRNA sequence without regard to the particular sequence of that siRNA.

An "on-target" event, as used herein, means that the mRNA of a target gene is impacted, i.e., knocked-down, by the siRNA designed to target that gene as evidenced by reduced expression, reduced levels of mRNA, or loss or gain of a particular phenotype. An "on-target" event can be verified via another method such as using a drug that is known to affect the target, or such as rescuing a lost phenotype by introduction of the target mRNA from an ortholog, for example.

An "off-target event," as used herein, means any event other than the desired event in RNA interference. An example of an off-target event is where a mRNA of a gene that is not targeted is impacted, i.e., knocked-down, by an siRNA. Such "off-target events" cannot be rescued by supplying the target mRNA from an appropriately related ortholog. "Off-target events" may be due to interaction with another mRNA, endogenous RNA, a DNA, or a protein in a way that alters non-target expression. Such off-target events may be due to, for example, mismatch base pairing between a nucleotide sequence incorporated into the RISC and a non-target mRNA, or non-specific interactions within the cellular mileau. Inappropriate RISC binding, inappropriate RISC-mediated interactions, and inappropriate RISC-mediated cleavage may contribute to off-target events. Off-target events also may be due to cytotoxic responses, an interferon response, a microRNA effect, or interaction with non-coding RNA. The most common off-target event is likely the undesired incorporation of the passenger (sense) strand into the RISC complex. However, the off-target events that are affected by siRNAs are not entirely predictable and tend to be non-specific. Off-target events give rise to off-target effects and the terms are used interchangeably herein.

The term "potency," as used herein, is a measure of the concentration of an individual or a pool of siRNA required to knock down its target mRNA to 50% of the starting mRNA level. Generally, potency is described in terms of IC50, the concentration of siRNA required for half maximum (50%) mRNA inhibition. Potency is determined herein by transfecting a range of siRNA concentrations (e.g., at least six ranging from 100 nM to 10 pm) and performing qRT-PCR analysis on the samples. The results are plotted and the IC50 is determined by extrapolating against the concentration where 50% of mRNA knockdown is achieved. A curve-fitting program is used to determine the concentration of siRNA needed to achieve 50% knockdown of the mRNA target. As used herein, the term "potency" is used interchangeably with the term "knockdown activity" which is a measure of the amount of decrease of mRNA after exposure to a test siRNA as compared to the amount of mRNA present after exposure to a negative control siRNA.

The term "efficacy," as used herein, is the percent of siRNA that produces a minimum threshold of mRNA knockdown. The term efficacy is commonly applied to a collection of siRNAs or to the predictive power of a siRNA design algorithm. Efficacy is measured by qRT-PCR or vector-based measurements of siRNA knockdown of a target mRNA, which results are expressed as the % of siRNAs that produce a minimum threshold of knockdown, e.g., % of siRNA that knockdown at 70% or better.

The term "specificity," as used herein, is a measure of the precision with which a siRNA impacts gene regulation at the mRNA level or protein level, or the true phenotype exhibited by knockdown of the target gene function. Specificity is measured by determining the number of genes that are changed relative to a certain threshold as a result of transfection of the siRNA, are not the intended target, and are not known to be in the signal transduction pathway of the target gene. The industry standard threshold is a 2-fold change. In cell biology studies, highly specific siRNAs to a particular target result in overlapping phenotypes with little to no unexpected phenotypes. Poor specificity siRNAs result in a phenotype due to off-target effects.

"Improved" potency refers to a siRNA having a lower IC50 or a higher percentage knockdown at the same concentration than another siRNA, "improved" specificity refers to a siRNA that impacts fewer genes than another siRNA, and "improved" efficacy refers to a group of siRNAs generated using an algorithm where a larger percentage of the siRNA group produces a minimum designated amount of knockdown as compared to another siRNA group generated using a different algorithm.

For studies herein, test results are compared to control results, and all results are normalized to a nonsense siRNA designed to be non-targeting. The Wilcoxon test for paired samples is the non-parametric equivalent of the paired samples t-test. The Wilcoxon test ranks the absolute values of the differences between the paired data in sample 1 and sample 2 and calculates a statistic on the number of negative and positive differences (differences are calculated as sample 2-sample 1). The software used is the "R Package" available at no charge from cran.org.

The term "nucleotide" generally refers to a phosphate ester of a nucleoside, either as a monomer or within a dinucleotide, oligonucleotide or polynucleotide. A nucleoside generally is a purine base or a pyrimidine base linked to the C-1' carbon of a ribose (a ribonucleoside) or of a deoxyribose (deoxyribonucleoside). Naturally occurring purine bases generally include adenine (A) and guanine (G). Naturally occurring pyrimidine bases generally include cytosine (C), uracil (U) and thymine (T). When the nucleoside base is a purine, the ribose or deoxyribose is attached to the nucleobase at the 9-position of the purine, and when the nucleobase is a pyrimidine, the ribose or deoxyribose is attached to the nucleobase at the 1-position of the pyrimidine. A ribonucleotide is a phosphate ester of a ribonucleoside and a deoxyribonucleotide is a phosphate ester of a deoxyribonucleoside. The term "nucleotide" is generic to both ribonucleotides and deoxyribonucleotides. A dinucleotide generally has two nucleotides covalently bonded via a 3'-5'phosphodiester linkage. An oligonucleotide generally has more than two nucleotides and a polynucleotide generally refers to polymers of nucleotide monomers. Applicants have used the terms "nucleotide" and "nucleoside" interchangeably herein for convenience although one of ordinary skill in the art readily understands, from the context in which the terms appear, which term is applicable.

Nucleotide monomers are linked by "internucleoside or internucleotide linkages," e.g., phosphodiester linkages where, as used herein, the term "phosphodiester linkage" refers to phosphodiester bonds or bonds including phosphate analogs thereof, including associated counterions, e.g., $H^+$, $NH_4^+$, $Na^+$, if such counterions are present. Further internucleoside or internucleotide linkages are described below. Whenever an oligonucleotide is represented by a sequence of letters, it will be understood that the nucleotides are in 5' to 3' order from left to right unless otherwise noted or it is apparent to the skilled artisan from the context that the converse was intended. Descriptions of how to synthesize oligonucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530. Oligonucleotides can be of any length.

"Base pairing," as used herein, refers to standard Watson-Crick base pairing. Base pairings found commonly in double-stranded (duplex) nucleic acids are G:C, A:T, and A:U. Such base pairs are referred to as complementary base pairs and one base is complementary to its paired base. Nucleotide analogs as described infra are also capable of forming hydrogen bonds when paired with a complementary nucleotide or nucleotide analog.

As used herein, the terms "complementary" or "complementarity" are used not only in reference to base pairs but also in reference to anti-parallel strands of oligonucleotides related by the Watson-Crick base-pairing rules, to nucleic acid sequences capable of base-pairing according to the standard complementary rules, or being capable of hybridizing to a particular nucleic acid segment under relatively stringent conditions. For example, the sequence 5'-AGTTC-3' is complementary to the sequence 5'-GAACT-3'. The terms "completely complementary" or "100% complementary" and the like refer to complementary sequences that have perfect pairing of bases between the anti-parallel strands (no mismatches in the polynucleotide duplex). Nucleic acid polymers can be complementary across only portions of their entire sequences. The terms "partial complementarity," "partially complementary," "incomplete complementarity" or "incompletely complementary" and the like refer to any alignment of bases between anti-parallel polynucleotide strands that is less than 100% perfect (e.g., there exists at least one mismatch in the polynucleotide duplex). Furthermore, two sequences are said to be complementary over a portion of their length if there exists one or more mismatches, gaps or insertions in their alignment.

Furthermore, a "complement" of a target polynucleotide refers to a polynucleotide that can combine in an anti-parallel association with at least a portion of the target polynucleotide. The anti-parallel association can be intramolecular, e.g., in the form of a hairpin loop within a nucleic acid molecule, or intermolecular, such as when two or more single-stranded nucleic acid molecules hybridize with one another. The term "corresponding to" when in reference to nucleic acids, means that a particular sequence is sufficiently complementary to an anti-parallel sequence such that the two sequences will anneal and form a duplex under appropriate conditions.

As used herein, a "passenger (sense)" strand, region, or oligonucleotide refers to a nucleotide sequence that has the same nucleotide sequence of at least a portion of the sense strand of DNA or of the nucleotide sequence of at least a portion of mRNA. A "passenger (sense) strand" includes a sense region of a polynucleotide that forms a duplex with a complementary guide (antisense) region of another polynucleotide. A hairpin single-stranded oligonucleotide (shRNA) may also contain a passenger (sense) region and a guide (antisense) region within the same molecule, the regions forming a duplex structure joined by a loop sequence or loop linker moiety as described further below. A hairpin can be in either a left-handed orientation (i.e., 5'-antisense-loop-sense-3') or a right-handed orientation (i.e., 5'-sense-loop-antisense-3').

As used herein, a "siRNA" refers to a short interfering RNA duplex that induces gene silencing via a RNA interference (RNAi) pathway. Short interfering RNAs can vary in length, and can contain at most one or two mismatched base pairs between the antisense and sense regions, and between the antisense region and a target mRNA sequence. Each siRNA can include 15 to 30 base pairs, or 18 to 25 base pairs, or 19 to 22 base pairs or 21 base pairs or 19 base pairs. In some embodiments, siRNAs have, independently, 1, 2, 3, 4, or 5 unpaired overhanging nucleotides on the 5' end, the 3' end, or both the 5' end and the 3' end. In some embodiments, siRNAs have blunt ends. In addition, the term "siRNA" includes duplexes of two separate strands, as well as single strands that can form hairpin structures (a shRNA). A shRNA may have a loop sequence of nucleotides such as 4 to 30, or 6 to 20 or 7 to 15 nucleotides or may comprise non-nucleotide moieties such as hydrocarbon linking regions, or a combination thereof. A shRNA may comprise mismatches or bulges.

In some embodiments, the present teachings comprise modified nucleotides that have enhanced affinity for base pairing as compared to non-modified nucleotides or that contribute enhanced affinity to the nucleotide sequence of which it is part. Modified nucleotides, as contemplated herein, shift the conformational equilibrium of an RNA toward the northern (C3'-endo) conformation consistent with the A-form geometry of RNA duplexes. DNA:RNA duplexes can also be stabilized thereby. In some embodiments, enhanced affinity for base pairing is achieved by constructing a passenger (sense) oligonucleotide having a bicyclonucleotide, tricyclonucleotide or a 2'-modified nucleotide.

In some embodiments, modified nucleotides for siRNA include, independently, modified sugar portions, modified base portions, modified internucleoside portions, or a combination of any of these modified portions.

In some embodiments, modified nucleotides include modified sugar portions including, but not limited to, 2'-halo where halo is chloro, fluoro, bromo or iodo; arabino or 2'-fluoro in an arabinose conformation (FANA); 2'—H, —SH, —NH$_2$, —CN, azide; or —OR, —R, —SR, —NHR, or —N(R)$_2$, wherein R is alkyl, alkenyl, alkynyl, alkoxy, oxyalkyl, alkoxyalkyl, alkylamine, where the alkyl portion is C1-C6.

Further 2' modifications include 2'-O—(CH$_2$)$_4$NH$_2$; 2'-O-anthraquinolylalkyl where alkyl comprises methyl or ethyl; 2'-O—(CH$_2$)$_2$—OCH$_3$; 2'-O—(CH$_2$CH$_2$O)$_n$—CH$_3$ where n is 1-4; 2'-O—CH$_2$—CHR—X where X=OH, F, CF$_3$ or OCH$_3$ and R=H, CH$_3$, CH$_2$OH or CH$_2$OCH$_3$; peptide nucleic acid monomers or derivatives thereof (PNA); 2' modifications where the 2'-position is alkoxy, e.g., methoxy, ethoxy, allyloxy, isopropoxy, butoxy, isobutoxy and phenoxy, and the like.

In some embodiments, modified nucleotides include modified sugar portions or pseudosugars including, but not limited to, bicyclonucleotide structure (a), tricyclonucleotide structure (b), or bicyclonucleotide structure (c):

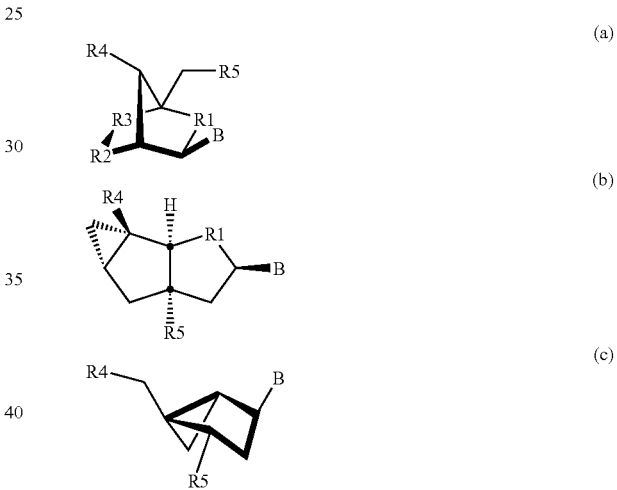

wherein R1 and R2 are independently O, S, CH$_2$, or NR where R is hydrogen or C$_{1-3}$-alkyl; R3 is CH$_2$, CH$_2$—O, CH$_2$—S, CH$_2$—CH$_2$, CH$_2$—CH$_2$—CH$_2$, CH=CH, or CH$_2$—NR where R is hydrogen or C$_{1-3}$-alkyl; R4 and R5 are independently an internucleoside linkage, a terminal group, or a protecting group; at least one of R4 and R5 is an internucleoside linkage; and B is a nucleobase, nucleobase derivative, or nucleobase analog. In some embodiments, R4 and R5 are independently H, OH, phosphate, C$_{1-12}$-alkyl, C$_{1-12}$-alkylamine, C$_{1-12}$-alkenyl, C$_{1-12}$-alkynyl, C$_{1-12}$-cycloalkyl, C$_{1-12}$-aralkyl, aryl, acyl, silyl, an oligonucleotide, a nucleoside bound via an internucleoside linkage, or a combination thereof; and at least one of R4 and R5 is an oligonucleotide, or a nucleoside bound via an internucleoside linkage. The 5' ends may further be derivatized by substituent groups such as phosphate, C$_{1-12}$-alkyl, C$_{1-12}$-alkylamine, C$_{1-12}$-alkenyl, C$_{1-12}$-alkynyl, C$_{1-12}$-cycloalkyl, C$_{1-12}$-aralkyl, aryl, acyl, or silyl. In some embodiments, the 5'-ends are derivatized by C$_{12}$ or C$_6$ substituted groups, or by phosphate, for example.

Bicyclonucleotides include those described above for structures (a) and (c). The bicyclo nucleotides of structure (a) are also termed locked nucleic acids or LNA® and include β-D, and α-L bicyclo nucleotides, bicyclo nucleotides such as xylo-locked nucleic acids (U.S. Pat. No. 7,084,125), L-ribo-locked nucleic acids (U.S. Pat. No. 7,053,207), 1'-2' locked nucleic acids (U.S. Pat. Nos. 6,734,291 and 6,639,059), and 3'-5' locked nucleic acids (U.S. Pat. No. 6,083,482), for example. Bicyclonucleotides of structure (c) and synthesis of oligonucleotides containing such bicyclonucleotides are described in, e.g., Maier et al. (*Nucleic Acids Research* 2004, 32:12, 3642-3650) and Maderia et al. (*Nucleic Acids Research* 2007, 35:6, 1978-1991). Tricyclonucleotides of structure (b) and synthesis of oligonucleotides containing such tricyclonucleotides are described in e.g., Ittig et al. (*Nucleic Acids Research* 2004, 32:1, 346-353).

In some embodiments, nucleotides include modified internucleoside linker portions including, but not limited to, phosphorothioate, phosphorodithioate, phosphoroselenoate, phosphorodiselenoate, phosphoroanilothioate, phosphoranilidate, phosphoramidate, boronophosphates, thioformacetal (—S—CH$_2$—O—CH$_2$—), methylene(methylimino), dimethylhydrazino, phosphoryl linked morpholino, —CH$_2$—CO—NH—CH$_2$—, —CH$_2$—NH—CO—CH$_2$—, and any analogs of phosphate wherein the phosphorous atom is in the +5 oxidation state and one or more of the oxygen atoms is replaced with a non-oxygen moiety, e.g., sulfur. A peptide nucleic acid is a nucleic acid analog in which the backbone comprises synthetic peptide like linkages (amide bonds) usually formed from N-(2-amino-ethyl)-glycine units, resulting in an achiral and uncharged molecule. Exemplary phosphate analogs include associated counterions, e.g., H$^+$, NH$_4^+$, Na$^+$, if such counterions are present.

In some embodiments, nucleotides include modified base portions including, but not limited to, pyrimidine nucleobases and purine nucleobases, and derivatives and analogs thereof, including but not limited to, pyrimidines and purines substituted by one or more of an alkyl, carboxyalkyl, amino, hydroxyl, halo (i.e., fluoro, chloro, bromo, or iodo), thiol or alkylthiol moiety. Alkyl (e.g., alkyl, carboxyalkyl, etc.) moieties comprise from 1 to 6 carbon atoms. Further modified nucleotides contemplated herein include an oxetane-modified base (for a discussion of base constraining oxetane modifications, see U.S. Published Patent Application No. 20040142946).

Pyrimidines, pyrimidine derivatives and pyrimidine analogs include, but are not limited to, bromothymine, 1-methylpseudouracil, 2-thiouracil, 2-thiothymine, 2-thiocytosine, 2-thiopyrimidine, 2-hydroxy-5-methyl-4-triazolopyridine, 3-methylcytosine, 3-(3-amino-3-carboxy-propyl)uracil, 4-acetylcytosine, 4-thiouracil, N4,N4-ethanocytosine, 4-(6-aminohexylcytosine), 5-methylcytosine, 5-ethylcytosine, 5-(C3,C6)-alkynylcytosine, 5-bromouracil, 5-(carboxyhydroxymethyl)uracil, 5-carboxymethylaminomethyl-2-thiouracil, 5-chlorouracil, 5-ethyluracil, 5-fluorouracil, 5-iodouracil, 5-propyluracil, 5-propynyluracil, thiouracil, 5-carboxymethylaminomethyluracil, 5-methylaminomethyluracil, 5-methoxyaminomethyl-2-thiouracil, 5-methoxycarbonylmethyluracil, 5-methoxyuracil, uracil-5-oxyacetic acid-methylester, uracil-5-oxyacetic acid, 5-methyl-2-thiouracil, 5-iodo-2'-deoxyuracil, 5-fluorouracil, 5-methyluracil, tricyclic carbazole-based pyrimidine analogs, tricyclic phenoxazine-based pyrimidine analogs, isocytosine, pseudoisocytosine, dihydrouracil, pseudouracil and universal nucleotides.

In some embodiments, purines, purine derivatives and purine analogs include, but are not limited to, azapurine, azaguanine, azaadenine, deazapurine, deazaguanine, deazaadenine, 1-methylguanine, 1-methyladenine, 1-methylinosine, 2-aminopurine, 2-chloro-6-aminopurine, 2,2-dimethylguanine, 2-methyladenine, 2-methylguanine, 2-methylthio-N6-isopentenyladenine, 2,6-diaminopurine, 6-aminopurine, 6-thioguanine, 6-thioadenine, 6-thiopurine, 6-hydroxyaminopurine, N6-methyladenine, N,N-diemethyladenine, N6-isopentenyladenine, N6,N6-ethano-2,6-diaminopurine, 7-deazaxanthine, 7-deazaguanine, 7-methylguanine, 7-halo-7-deaza purine where halo is bromo, fluoro, iodo or chloro, 7-propyne-7-deaza purine, 8-bromoadenine, 8-hydroxyadenine, 8-bromoguanine, 8-chloroguanine, 8-aminoguanine, 8-hydroxyguanine, 8-methylguanine, 8-thioguanine, 8-oxo-N6-methyladenine, N-((9-β-D-ribofuranosylpurine-6-yl)-carbamoyl)threonine, methylthioadenine, xanthine, hypoxanthine, inosine, wybutoxosine, wybutosine, isoguanine, queuosine, β-D-mannosylqueuosine, β-D-galactosylqueuosine, and universal nucleotides.

A universal base may base pair with more than one type of specific base or with any specific base. In other embodiments, a universal base doesn't hydrogen bond specifically with any base but interacts with adjacent bases on the same nucleic acid strand by hydrophobic stacking. Universal bases include, but are not limited to, indoles such as 7-azaindole, 6-methyl-7-azaindole, propynyl-7-aza-indole, allenyl-7-azaindole, isocarbostyril, propynylisocarbostyril, imidizopyridine, and pyrrollpyrizine.

In some embodiments, modified nucleotides are present in siRNAs in particular patterns, termed herein, "formats," as exemplified by the patterns or formats set forth by FIG. 1A-FIG. 1K. In some embodiments, a chemically synthesized passenger (sense) oligonucleotide has a length of 15 to 30 nucleotides and comprises one of sequence-independent modification format (1), sequence-independent modification format (2), and sequence-independent modification format (3):

(1) 5' $N_p$-m-m-$N_x$-m-m-N-$n_r$ 3', wherein p is 0 or 1; x is 7, 8, 9, 10, or 11; r is 0, 1, or 2; and q is an integer representing the length of the passenger strand minus (p+x+r+4);

(2) 5' $N_p$-m-m-$N_y$-m-$N_z$-m-$N_q$-$n_r$ 3', wherein p is 0 or 1; y is 7, 8, or 9 and z is 1; or y is 7 and z is 2 or 3; r is 0, 1, or 2; and q is an integer representing the length of the passenger strand minus (p+y+z+r+4);

(3) 5'm-$N_1$-m-$N_x$-m-m-$N_q$-$n_r$ 3', wherein x is 8, 9, or 10; r is 0, 1, or 2; and q is an integer representing the length of the passenger strand minus (x+r+5);

wherein each m is independently a bicyclonucleotide or a tricyclonucleotide; each n is independently a deoxynucleotide, modified nucleotide, or ribonucleotide; and when m is a bicyclonucleotide, each N is independently a nucleotide other than a bicyclonucleotide; and when m is a tricyclonucleotide, each N is independently a nucleotide other than a tricyclonucleotide.

In some embodiments, a chemically synthesized passenger (sense) oligonucleotide is provided, the oligonucleotide consists essentially of a length of 15 to 30 nucleotides and consists essentially of one of sequence-independent modification format (1), sequence-independent modification format (2), and sequence-independent modification format (3) as follows:

(1) 5' $N_p$-m-m-$N_x$-m-m-$N_q$-$n_r$ 3', wherein p is 0 or 1; x is 7, 8, 9, 10, or 11; r is 0, 1, or 2; and q is an integer representing the length of the passenger strand minus (p+x+r+4);

(2) 5' $N_p$-m-m-$N_y$-m-$N_z$-m-$N_q$-$n_r$ 3', wherein p is 0 or 1; y is 7, 8, or 9 and z is 1; or y is 7 and z is 2 or 3; r is 0, 1, or 2; and q is an integer representing the length of the passenger strand minus (p+y+z+r+4);

(3) 5' m-N$_1$-m-N$_x$-m-m-N$_q$-n$_r$ 3', wherein x is 8, 9, or 10; r is 0, 1, or 2; and q is an integer representing the length of the passenger strand minus (x+r+5);

wherein each m is independently a bicyclonucleotide or a tricyclonucleotide; each n is independently a deoxynucleotide, modified nucleotide, or ribonucleotide; when m is a bicyclonucleotide, each N is independently a nucleotide other than a bicyclonucleotide, and when m is a tricyclonucleotide, each N is independently a nucleotide other than a tricyclonucleotide.

In some embodiments, a guide (antisense) oligonucleotide comprises 15 to 30 nucleotides, a region of continuous complementarity to the passenger (sense) oligonucleotide of at least 12 nucleotides, and has complementarity to at least a portion of a target mRNA. In some embodiments, a guide (antisense) oligonucleotide comprises a region of continuous complementarity to the passenger (sense) oligonucleotide of from at least 13 nucleotides to a number of nucleotides that corresponds to the full length of the oligonucleotide. In some embodiments, a guide (antisense) oligonucleotide comprises a region of continuous complementarity to the full length of the passenger (sense) oligonucleotide with the exception of the two 3' nucleotides.

In some embodiments, the guide (antisense) oligonucleotide has complementarity of at least 12 continuous nucleotides to at least a portion of a target mRNA. In some embodiments, the guide (antisense) oligonucleotide has complementarity of at least from 13 nucleotides to a number of nucleotides that corresponds to the full length of the guide oligonucleotide to at least a portion of a target mRNA. In some embodiments, a guide oligonucleotide has full complementarity to a portion of a target mRNA with the exception of the two 3' nucleotides.

In some embodiments, a short interfering RNA is provided that comprises a passenger (sense) oligonucleotide having a length of 17 to 30 nucleotides and comprising one of sequence-independent modification format (4), format (5), and format (6) and a guide (antisense) oligonucleotide having 17 to 30 nucleotides, a region of continuous complementarity to the passenger (sense) oligonucleotide of at least 12 nucleotides; the guide strand further having complementarity to at least a portion of target mRNA:

(4) 5' m$_p$-N$_x$-m-m-N$_q$-n$_r$ 3' wherein when p is 0, x is 12; when p is 1, x is 11; when p is 2, x is 10; when p is 3, x is 9, when p is 4, x is 8; r is 0, 1, or 2; and q is an integer representing the length of the passenger strand minus (p+x+r+2);

(5) 5' m-m-N$_x$-m-N$_q$-n$_r$ 3' wherein x is 11; r is 0, 1, or 2; and q is an integer representing the length of the passenger strand minus (x+r+3);

(6) 5' m$_p$-N$_y$-m-N$_z$m-N$_q$-n$_r$ 3', wherein p is 3; y is 9 and z is 1; r is 0, 1, or 2; and q is an integer representing the length of the passenger strand minus (p+y+z+r+2);

wherein each m is independently a bicyclonucleotide, a tricyclonucleotide, or a 2'-modified nucleotide; each n is independently a deoxynucleotide, modified nucleotide, or ribonucleotide and is an overhanging nucleotide; when m is a bicyclonucleotide, each N is independently a nucleotide other than a bicyclonucleotide, when m is a tricyclonucleotide, each N is independently a nucleotide other than a tricyclonucleotide, and when m is a 2'-modified nucleotide, each N is independently a nucleotide other than a 2'-modified nucleotide.

In an embodiment of the short interfering RNA, the passenger (sense) oligonucleotide has sequence independent modification format (4), p is 2, x is 10, r is 2, each n is an overhanging nucleotide, and each n is independently a modified nucleotide; the guide (antisense) oligonucleotide comprises two 3'-overhanging modified nucleotides; and each modified nucleotide is independently a bicyclonucleotide, a tricyclonucleotide, or a 2'-modified nucleotide. In one embodiment, at least one of the 3' antepenultimate and the 3' preantepenultimate positions of the passenger oligonucleotide is a modified nucleotide. The 3' antepenultimate position is the third from the last position, i.e., the position prior to the penultimate position, e.g., as for Format DH47 of FIG. 1H. The 3' preantepenultimate position is the fourth from the last position, i.e., the position prior to the antepenultimate position, e.g., as for Format DH29 of FIG. 1H. Such siRNAs are particularly stable to nucleases such as in the presence of serum, for example.

In some embodiments of the short interfering RNA, when the length is 17 nucleotides, at least one of positions 2 and 3 of the guide oligonucleotide is a modified nucleotide; when the length is 18 nucleotides, at least one of positions 2, 3 and 4 of the guide oligonucleotide is a modified nucleotide; when the length is 19 nucleotides, at least one of positions 2, 3, 4 and 5 of the guide oligonucleotide is a modified nucleotide; when the length is 20 nucleotides, at least one of positions 2, 3, 4, 5 and 6 of the guide oligonucleotide is a modified nucleotide; and when the length is 21-30 nucleotides, at least one of positions 2, 3, 4, 5, 6 and 7 of the guide oligonucleotide is a modified nucleotide. Formats DH1, and Formats DH39-DH43 of FIG. 1K provide examples of siRNA modification formats having a length of 21 nucleotides and having at least one of positions 2, 3, 4, 5, 6 and 7 of the guide oligonucleotide as a modified nucleotide. Such siRNAs are also particularly stable to nucleases such as in the presence of serum or plasma, for example.

In some embodiments, the passenger (sense) oligonucleotide comprises sequence-independent modification format (1) where p is 0, x is 10 and r is 2 (Format H, a 21-mer having Format H is depicted in FIG. 1A); or sequence-independent modification format (1) where p is 0, x is 9 or 11, and r is 2 (Format H−1 or Format H+1, 21-mers having such formats are depicted in FIG. 1B); or sequence-independent modification format (2) where p is 0, y is 9, and r is 2 (Format V, a 21-mer having Format V is depicted in FIG. 1C).

In some embodiments, the passenger (sense) oligonucleotide comprises sequence-independent modification format (1) where p is 1, x is 9 or 10, r is 2, (Format W or Format W+1, 21-mers having such formats are depicted in FIG. 1D), and each m has structure (a) where R1 is O, R2 is O, and R3 is CH$_2$. In some embodiments, the passenger (sense) oligonucleotide comprises sequence-independent modification format (3), x is 9 or 10, r is 2, (Format Y or Format Y+1, 21-mers having such formats are depicted in FIG. 1D) and each m has structure (a) where R1 is O, R2 is O, and R3 is CH$_2$.

In further embodiments, each N of the guide (antisense) strand is a nucleotide other than a bicyclonucleotide. In some embodiments, the guide (antisense) strand has no modifications.

In some embodiments, the siRNA passenger oligonucleotide has modification Format H wherein modified nucleotides m are at positions 1, 2, 13, and 14 of the format; each m is an LNA®; each n is a deoxynucleotide; and each N is a ribonucleotide. In some embodiments, the siRNA passenger oligonucleotide has the modification Format H and each m has structure (a) where R1 is O, R2 is O, and R3 is CH$_2$.

In some embodiments, the siRNA passenger oligonucleotide has modification Format V wherein modified nucleotides m are at positions 1, 2, 12, and 14 of the format; each m is an LNA®; each n is a deoxynucleotide; and each N is a ribonucleotide. In some embodiments, the siRNA passenger oligonucleotide has the modification Format V and each m has structure (a) where R1 is O, R2 is O, and R3 is $CH_2$. In some embodiments, the siRNA passenger oligonucleotide has modification Format V-2 having format (2) where p is 0 and y is 7.

In some embodiments, the siRNA passenger oligonucleotide has modification Format Q wherein modified nucleotides m are at positions 13 and 14 of the format; each m is an LNA®; each n is a deoxynucleotide; and each N is a ribonucleotide. In some embodiments, the siRNA passenger oligonucleotide has the modification Format Q and each m has structure (a) where R1 is O, R2 is O, and R3 is $CH_2$.

In some embodiments, the siRNA passenger oligonucleotide has format (4) wherein when p is 0, x is 12 (Format Q); when p is 1, x is 11 (Format JB2); when p is 2, x is 10 (Format H); when p is 3, x is 9 (Format JB5), and when p is 4, x is 8 (Format JB3) and r is 2. In some embodiments, the siRNA passenger oligonucleotide has format (5) wherein x is 11 (Format JB1) and r is 2. In further embodiments, the siRNA passenger oligonucleotide has format (6) wherein p is 3, y is 9, and z is 1 (Format JB4) and r is 2.

In some embodiments, the chemically synthesized short interfering RNA comprises a passenger (sense) oligonucleotide and a guide (antisense) oligonucleotide covalently bonded via nucleotide loop or a linker loop which forms a short hairpin oligonucleotide.

In some embodiments, each 3'end of the siRNA independently has a one, two, or three nucleotide overhang and in some embodiments, each 3' end has a two nucleotide overhang wherein the nucleotides of each overhang comprise deoxyribonucleotides. In some embodiments, at least one overhanging nucleotide is a modified nucleotide. In some embodiments, each 3' end of the siRNA has a two nucleotide overhang and one, two, three or all four of the overhanging nucleotides are modified nucleotides. In some embodiments, at least one internucleoside linkage is other than a phosphodiester internucleoside linkage.

Chemical Synthesis:

Interfering RNA oligonucleotide synthesis is performed according to standard methods. Non-limiting examples of synthesis methods include in vitro chemical synthesis using a diester method, a triester method, a polynucleotide phosphorylase method and by solid-phase chemistry. These methods are discussed in further detail below.

Oligonucleotides having bicyclonucleotide structures including those of structure (a) are synthesized according to Imanishi as described in U.S. Pat. Nos. 6,770,748 and 6,268,490; according to Wengel as described in U.S. Pat. Nos. 7,084,125, 7,060,809, 7,053,207, 7,034,133, 6,794,499, and 6,670,461 and U.S. Published Application No's 2005/0287566, and 2003/0224377; according to Kochkine as described in U.S. Pat. Nos. 6,734,291, and 6,639,059 and U.S. Published Application No 2003/0092905; and according to Kauppinen as described in U.S. Published Application No's 2004/0219565, and according to Srivastava, P., et al. (*J. Am. Chem. Soc.* 129, 8362-8379, 2007) for example.

Oligonucleotides having tricyclonucleotide structure (b) are synthesized according to Ittig, D. et al. (Nucleic Acids Res. 32:1, 346-353, 2004), for example. Oligonucleotides having bicyclonucleotide structure (c) are synthesized according to Maier, M. A., et al. (*Nucleic Acids Res.* 32:12, 3642-3650, 2004), for example. Oligonucleotides having a FANA substituent are synthesized according to Dowler et al. (*Nucleic Acids Res.* 2006, 34:6, p 1669-1675).

The diester method of oligonucleotide synthesis was the first to be developed to a usable state, primarily by Khorana et al. (*Science,* 203, 614. 1979). The basic step is the joining of two suitably protected nucleotides to form a dinucleotide containing a phosphodiester bond. The diester method is well established and has been used to synthesize DNA molecules.

The main difference between the diester and triester methods is the presence in the latter of an extra protecting group on the phosphate atoms of the reactants and products (Itakura et al., *J. Biol. Chem.,* 250:4592 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage, S. L. and Iyer, R. P. *Tetrahedron,* 1993(49) 6123; *Tetrahedron,* 1992(48) 2223) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

A siRNA may be purified on reversed phase purification cartridges, ion exchange HPLC, agarose gels, polyacrylamide gels, cesium chloride centrifugation gradients, a column, filter, or cartridge containing an agent that binds to the nucleic acid, such as a glass fiber, or by any other means known to one of ordinary skill in the art. Gel electrophoresis can be used for determining single vs. double strand structure, ion exchange HPLC can be used for determining purity, MALDI-MS can be used for determining identity, and UV spectroscopy can be used for quantitative determinations of siRNAs.

A cell containing an endogenous target gene may be derived from or contained in any organism (e.g., eukaryotes such as plants, animals, fungi; prokaryotes such as bacteria). The plant may be a monocot, dicot or gynmosperm; the animal may be a vertebrate or invertebrate. A microbe may be used in agriculture or by industry, or may be pathogenic for plants or animals. Fungi include organisms in both the mold and yeast morphologies. Examples of vertebrates include fish and mammals, including cattle, goat, pig, sheep, hamster, mouse, rats and humans; invertebrate animals include nematodes, insects, arachnids, and other arthropods.

The target gene can be a gene derived from a cell, an endogenous gene, a transgene, or exogenous genes such as genes of a pathogen, for example, a virus, which is present in the cell after infection thereof. The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus encompasses fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells, of the endocrine or exocrine glands.

In some embodiments, the target RNA is transcribed RNA, including coding RNA and noncoding RNA.

As used herein, the terms "cell," "cell line," and "cell culture" include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding such an RNA has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In some embodiments, a tissue containing an endogenous target gene is human tissue. In certain embodiments, the tissue comprises blood, for example but not limited to, red blood cells, white blood cells, platelets, plasma, serum, or whole blood. In certain embodiments, the tissue comprises a solid tissue. In certain embodiments, the tissue comprises a virus, bacteria, or fungus. In certain embodiments, the tissue comprises ex vivo tissue.

A tissue may comprise a host cell or cells to be transformed or contacted with a nucleic acid delivery composition or an additional agent. The tissue may be part or separated from an organism. In certain embodiments, a tissue and its constituent cells may comprise, but is not limited to, blood (e.g., hematopoietic cells (such as human hematopoietic progenitor cells, human hematopoietic stem cells, CD34+ cells CD4+cells), lymphocytes and other blood lineage cells), bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes.

In some embodiments, modification-formatted siRNAs are provided that are stabilized to intracellular and extracellular nucleases. Such siRNAs are demonstrated herein to remain at full-length in the presence of biological fluids for a longer time than previously known stabilized siRNAs. Nuclease stabilized siRNAs are useful in biological fluids and tissues that contain particularly high concentrations of nucleases including, for example, blood serum, blood plasma, and organs and tissues that are particularly vascularized.

A siRNA may be associated with a cell-targeting ligand. As used herein, a "cell targeting ligand" is a cell-directing molecule that has specificity for targeted sites such as cell surface receptors. "Specificity for targeted sites" means that upon contacting the cell targeting ligand with a cell, under physiological conditions of ionic strength, temperature, pH and the like, specific binding will occur. The cell-ligand interaction may occur due to specific electrostatic, hydrophobic, or other interaction of certain residues of the ligand with specific residues of the cell to form a stable complex under conditions effective to promote the interaction.

Exemplary cell targeting ligands include, but are not limited to, polynucleotides, oligonucleotides, polyamides, peptides having affinity for a cellular receptor, proteins such as antibodies, fatty acids, vitamins, flavonoids, sugars, antigens, receptors, reporter molecules, reporter enzymes, chelators, porphyrins, intercalators, steroids and steroid derivatives, hormones such as progestins (e.g. progesterone), glucocorticoids (e.g., cortisol), mineralocorticoids (e.g., aldosterone), androgens (e.g., testosterone) and estrogens (e.g., estradiol), histamine, hormone mimics such as morphine, and macrocycles. A peptide having affinity for a cellular receptor may include an endorphin, an enkephalin, a growth factor, e.g. epidermal growth factor, poly-L-lysine, a hormone, insulin, ribonuclease, serum albumin binding peptide, a peptide region of a protein and other molecules that are capable of penetrating cellular membranes, either by active transport or passive transport.

Suitable methods for siRNA delivery to effect RNAi according to embodiments include any method by which a siRNA can be introduced into an organelle, a cell, a tissue or an organism, as described herein or as would be known to one of ordinary skill in the art. Such methods include, but are not limited to, direct delivery of siRNA such as by injection including microinjection, electroporation, calcium phosphate precipitation, using DEAE-dextran followed by polyethylene glycol, direct sonic loading, liposome mediated transfection, microprojectile bombardment, agitation with silicon carbide fibers, *Agrobacterium*-mediated transformation, PEG-mediated transformation, desiccation/inhibition-mediated uptake, and the like. Through the use of techniques such as these, an organelle, cell, tissue or organism may be stably or transiently transformed. SiRNAs that are stabilized to nuclease digestion, embodiments of which are provided herein, are particularly suited for direct injection as demonstrated by the data of Example 8 where serum-stabilized modification-formatted siRNAs were present in vivo at a level 400% greater than unmodified siRNAs.

Techniques for visualizing or detecting siRNA include, without limitation, microscopy, arrays, fluorometry, light cyclers or other real time PCR machines, FACS analysis, scintillation counters, phosphoimagers, Geiger counters, MRI, CAT, antibody-based detection methods (Westerns, immunofluorescence, immunohistochemistry), histochemical techniques, HPLC, spectroscopy, mass spectroscopy; radiological techniques, capillary gel electrophoresis, and mass balance techniques. Alternatively, nucleic acids may be labeled or tagged to allow for their efficient isolation. In other embodiments of the invention, nucleic acids are biotinylated.

A "label" or "reporter," refers to a moiety or property that allows the detection of that with which it is associated. The label can be attached covalently or non-covalently. Examples of labels include fluorescent labels (including, e.g., quenchers or absorbers), colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

Fluorescent labels can include dyes that are negatively charged, such as dyes of the fluorescein family including, e.g. FAM, HEX, TET, JOE, NAN and ZOE; or dyes that are neutral in charge, such as dyes of the rhodamine family including, e.g., Texas Red, ROX, R110, R6G, and TAMRA; or dyes that are positively charged, such as dyes of the cyanine family including e.g., Cy2, Cy3, Cy3.5, Cy5, Cy5.5 and Cy7. FAM, HEX, TET, JOE, NAN, ZOE, ROX, R110, R6G, and TAMRA are available from, e.g., Perkin-Elmer, Inc. (Wellesley, Mass.); Texas Red is available from, e.g., Molecular Probes, Inc. (Eugene, Oreg.); and Cy2, Cy3, Cy3.5, Cy5, Cy5.5 and Cy7, and are available from, e.g., Amersham Biosciences Corp. (Piscataway, N.J.). In certain embodiments, the fluorescer molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TAQMAN™ probes (Applied Biosystems, Foster City, Calif.). The fluorophore can be any fluorophore that can be attached to a nucleic acid, such as, for example, FAM, HEX, TET, JOE, NAN, ZOE, Texas Red, ROX, R110, R6G, TAMRA, Cy2, Cy3.5, Cy5, Cy5.5 and Cy7 as cited above as well as VIC, NED, LIZ, ALEXA, Cy9, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch). Labels can also comprise sulfonate derivatives of fluorescein dyes, phosphoramidite forms of fluorescein, phosphoramidite forms of CY5 (available for example from Amersham), intercalating labels such as ethidium bromide, and SYBR™ Green I and PICOGREEN™ (Molecular Probes).

In various embodiments, detection of fluorescence can be by any method known to skilled artisans, and can be qualitative or quantitative. Quantitative results can be obtained, for example, with the aid of a fluorimeter. In some embodiments, detection can be achieved using microarrays and related software such as the Applied Biosystems Array System with the Applied Biosystems 1700 Chemiluminescent Microarray Analyzer and other commercially available array systems available from Affymetrix, Agilent, Illumina, and NimbleGen, among others (see also Gerry et al., *J. Mol. Biol.* 292: 251-62, 1999; De Bellis et al., *Minerva Biotec* 14:247-52, 2002; and Stears et al., *Nat. Med.* 9:140-45, including supplements, 2003).

A biologically acceptable carrier refers to those carriers that provide suitable preservation, if needed, and deliver one or more interfering RNAs of the present embodiments in a homogenous dosage. The type of carrier may depend on whether the siRNA is to be used in a solid, liquid or aerosol form, and whether it needs to be sterile for such routes of administration as injection. The siRNA compositions may be formulated into a composition in a free base, neutral or salt form. A salt form of siRNA has properties of reducing off-target effects and maintaining knockdown activity comparable to that of the siRNAs described herein. Examples of salt forms include organic acid addition salts and base addition salts. SiRNA compositions may be provided in a prodrug form that can be metabolized intracellularly into the active form; such prodrug forms may include a protection group such as an S-acetylthioethyl or S-pivaloylthioethyl group.

In embodiments where the composition is in a liquid form, a carrier can be a solvent or dispersion medium comprising, but not limited to, RNase-free water, buffer, saline, ethanol, polyol (e.g., glycerol, propylene glycol, liquid polyethylene glycol, etc.), lipids (e.g., triglycerides, vegetable oils, liposomes), glycine, acceptable preservatives (e.g., antibacterial agents, antifungal agents), co-solvents, surfactants, penetration enhancers (e.g., cremephor and TWEEN™ 80 (polyoxyethylene sorbitan monolaureate, Sigma Aldrich, St. Louis, Mo.)), hyaluronic acid, mannitol, benzalkonium chloride, viscosity building agents (e.g., hydroxymethyl cellulose, hydroxyethyl cellulose, methylcellulose, polyvinylpyrrolidone, hydroxypropylmethylcellulose), coatings, surfactants, antioxidants, isotonic agents, absorption delaying agents, gels, binders, excipients, disintegration agents, lubricants, sweetening agents, flavoring agents, dyes, and combinations thereof. Sterile injectable solutions are prepared by incorporating the siRNA in an appropriate solvent with various of the other ingredients enumerated above, as desired, followed by filtered sterilization. Formulations comprise interfering RNAs, or salts thereof, of embodiments herein up to 99% by weight mixed with a biologically acceptable carrier. Interfering RNAs of embodiments can be employed as solutions, suspensions, or emulsions.

An acceptable carrier for use of interfering RNA of embodiments includes the lipid-based reagent siPORT™ NeoFX™ Transfection Agent (Ambion Cat. #AM4510), the polyamine-based reagent siPORT™ Amine Transfection Agent (Ambion Cat. #AM4502), the cationic and neutral lipid-based reagent siPORT™ Lipid Transfection Agent (Ambion Cat. #AM4504), the cationic lipid-based transfection reagent TransIT®-TKO (Minis Corporation, Madison, Wis.), Lipofectin®, Lipofectamine, Oligofectamine™ (Invitrogen, Carlsbad, Calif.), or Dharmafect™ (Dharmacon, Lafayette, Colo.), further polycations such as polyethyleneimine, cationic peptides such as Tat, polyarginine, or penetratin, or liposomes. Liposomes are formed from standard vesicle-forming lipids and a sterol, such as cholesterol, and may include a targeting molecule such as a monoclonal antibody having binding affinity for a cell surface antigen, for example. Further, the liposomes may be PEGylated liposomes.

Interfering RNAs may be delivered in solution, in suspension, or in bioerodible or non-bioerodible delivery devices. The interfering RNAs can be delivered alone or as components of defined, covalent conjugates such as with a polyethylene glycol moiety, a cholesterol moiety, or with growth factors for receptor-mediated endocytosis. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment. Except insofar as any conventional carrier is incompatible with the siRNA, its use in a composition, or as a biological carrier is contemplated by embodiments herein.

Interfering RNA of embodiments herein can be administered intravenously, intradermally, intraarterially, intraperitoneally, intralesionally, intracranially, intraarticularly, intraventricularly, intraprostaticaly, intrapleurally, intratracheally, intranasally, intravitreally, intravaginally, intrauterinely, intrarectally, topically, intratumorally, intrathecally, intramuscularly, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the foregoing as would be known to one of ordinary skill in the art (*Remington's Pharmaceutical Sciences,* 18th Ed., Mack Publishing Co. 1990).

A dosage for ex vivo or in vivo use is from 0.01 µg to 1 g/kg of body weight, and may be administered once or more per day, week, month or year. Generally, an effective amount of the interfering RNAs having modified nucleotides and modification formats of embodiments herein is an amount sufficient to reduce off-target events while maintaining potency and results in an extracellular concentration at the surface of the target cell of from 100 µM to 1 µM, or from 1 nM to 100 nM, or from 2 nM to about 25 nM, or to about 10 nM. The amount required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. The pH of the formulation is about pH 4-9, or pH 4.5 to pH 7.4.

In some embodiments, the ability of siRNA to knockdown the levels of endogenous target gene expression is evaluated in vitro as follows. Cells are transfected using the siPORT™ NeoFX™ Transfection Agent (Ambion/Applied Biosystems Austin, Tex. Cat #AM4510) using the "reverse" transfection protocol described by the manufacturer. Unmodified control or modification-formatted siRNA is plated into 96-well tissue culture plates to achieve a final concentration of, for example, either 1 nM or 5 nM. SiPORT™ NeoFX™ transfection agent is complexed with siRNA for at least 10 minutes, followed by overlaying freshly trypsinized cells (about $4.0 \times 10^3$) on the siRNA/transfection agent complex. The plates are incubated under tissue culture conditions at 37° C. for 48 hours.

After harvesting transfected cells, total RNA is isolated using the MagMAX™-96 total RNA isolation kit (Ambion, Inc. Austin, Tex. Cat. #AM1830) according to the manufacturer's protocol. RNA is eluted in 50 µl of nuclease-free water. CDNA is generated using the High Capacity cDNA Reverse Transcription Kit (Applied Biosystems, Inc., Foster City, Calif., Cat. #4368814) according to the manufacturer's protocol in a 30 µl reaction volume. TaqMan® Gene Expression Assays (Applied Biosystems, Inc., Cat. #4331182) are carried out using 2 µl of cDNA in a 10 µl total PCR reaction volume. Technical replicates are generated and an 18S value is calculated for each sample. Preamplification uniformity is checked by calculating the ddCT using the following formula:

$$ddCT = (\text{siRNA treated Ct}_{GOI} - \text{siRNA treated Ct}_{18S}) - (\text{Neg control Ct}_{GOI} - \text{Neg control Ct}_{18S})$$

GOI=endogenous gene of interest
18S=18S ribosomal RNA normalizer
siRNA treated=biological sample treated with an siRNA
Neg control=biological sample treated with an siRNA that has no homology to any known target mRNA
The % remaining was calculated using the following formula:

$$\% \text{ remaining} = 100 \times 2^{-(ddCT)}.$$

Target protein levels may be assessed approximately 72 h post-transfection (actual time dependent on protein turnover rate) by western blot, for example. Standard techniques for RNA and/or protein isolation from cultured cells are well-known to those skilled in the art.

Techniques for visualizing or detecting siRNA include those cited above. Nucleic acids may be labeled or tagged to allow for their efficient isolation. Thus, the silencing ability of any given siRNA can be studied by one of any number of art tested procedures.

A "kit," as used herein, refers to a combination of at least some items for reducing off-target effects in RNA interference. Embodiments of kits comprise, for example, at least one siRNA having modified nucleotides in a modification format of embodiments herein. The at least one siRNA can be custom made. In some embodiments, kits comprise at least one siRNA having bicyclonucleotides in modification Format H, Q, V−2, Y, Y+1, JB1, JB2, JB3, JB4 or JB5 together with a biologically acceptable carrier such as a buffer, and a transfection agent or other suitable delivery vehicle.

Embodiments of kits can further comprise a validated positive control siRNA that targets a housekeeping gene in all cell types of human, mouse, and rat. Embodiments of kits can further comprise a validated negative control siRNA that is nontargeting. The siRNA controls may be pre-plated and may be labeled with a detectable marker.

Embodiments of kits can further comprise reagents for assessing knockdown of the intended target gene such as antibodies for monitoring knockdown at the protein level by immunofluorescence or Western analysis, reagents for assessing enzymatic activity or presence of a reporter protein, or reagents for assessing cell viability. RT-PCR primers and probes may be included for detection of target or reporter mRNA. Embodiments of kits can further comprise an RNase inhibitor.

The container means of the kits will generally include at least one vial, test tube, flask, bottle, syringe or other packaging means, into which a component can be placed, and in some embodiments, suitably aliquoted. Where more than one component is included in the kit (they can be packaged together), the kit also will generally contain at least one second, third or other additional container into which the additional components can be separately placed. However, various combinations of components can be packaged in a container means. The kits of the present teachings also will typically include a means for containing the siRNA having modified nucleotides in a modification format as set forth herein, and any other reagent containers in close confinement for commercial sale. Such containers can include injection or blow-molded plastic containers into which the desired container means are retained. When the components of the kit are provided in one and/or more liquid solutions, the liquid solution comprises an aqueous solution that can be a sterile aqueous solution.

In certain embodiments, at least one kit component is lyophilized and provided as dried powder(s). When reagents and/or components are provided as a dry powder, the powder can be reconstituted by the addition of a suitable solvent. In certain embodiments, the solvent is provided in another container means. Kits can also comprise an additional container means for containing a sterile, biologically acceptable buffer and/or other diluent.

A kit can also include instructions for employing the kit components as well as the use of any other reagent not included in the kit. Instructions can include variations that can be implemented.

The present method and kit embodiments may be employed for high volume screening. A library of either siRNA or candidate siRNA can be constructed using embodiments herein. This library may then be used in high throughput assays, including microarrays. Specifically contemplated are chip-based nucleic acid technologies that involve quantitative methods for analyzing large numbers of genes rapidly and accurately. By using fixed probe arrays, one can employ chip technology to segregate target molecules as high density arrays and screen these molecules on the basis of hybridization. The term "array" as used herein refers to a systematic arrangement of nucleic acid. For example, a nucleic acid population that is representative of a desired source (e.g., human adult brain) is divided up into the minimum number of pools in which a desired screening procedure can be utilized to detect or deplete a target gene and which can be distributed into a single multi-well plate. Arrays may be of an aqueous suspension of a nucleic acid population obtainable from a desired mRNA source, comprising: a multi-well plate containing a plurality of individual wells, each individual well containing an aqueous suspension of a different content of a nucleic acid population. Examples of arrays, their uses, and implementation of them can be found in U.S. Pat. Nos. 6,329, 209, 6,329,140, 6,324,479, 6,322,971, 6,316,193, 6,309,823, 5,412,087, 5,445,934, and 5,744,305, which are herein incorporated by reference.

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

A solid support may be made from glass, plastic (e.g., polypropylene, nylon), polyacrylamide, nitrocellulose, or other materials. Exemplary methods for attaching nucleic acids to a surface include printing on glass plates or by masking. In principal, any type of array, for example, dot blots on a nylon hybridization membrane, could be used, although, as will be recognized by those of skill in the art, very small arrays will be preferred because hybridization volumes will be smaller Embodiments of the present teachings can be further understood in light of the following examples, which should not be construed as limiting the scope of the present teachings in any way.

Example 1 siRNA Modification Formats

Short interfering RNAs (siRNAs) were chemically synthesized using standard phosphoramidite-based nucleoside monomers and established solid phase oligomerization cycles according to Beaucage, S. L. and Iyer, R. P. (*Tetrahedron*, 1993 (49) 6123; *Tetrahedron*, 1992 (48) 2223). Synthesis of oligonucleotides was performed on a BioAutomation MerMade 192 synthesizer (BioAutomation Corp, Plano, Tex.). Eight equivalents of activator were used for every equivalent of LNA® phosphoramidite to provide a satisfactory stepwise coupling yield of >98% per base addition. Purification of the individual siRNA strands was carried out using either disposable reversed phase purification cartridges or ion exchange HPLC. Gel electrophoresis was used for determining single vs. double strand structure for annealed samples, ion exchange HPLC was used for determining single strand purity, MALDI mass spectrometry was used for determining single strand identity, and UV spectroscopy was used for quantitative determination for both single strand oligonucleotides and siRNAs. The guide and passenger strands of each siRNA are both 21 nucleotides long and every siRNA was designed with a two base overhang on both 3' ends. Position 1 of each guide (antisense) strand was designed to be either an "A nucleotide" or a "U nucleotide." When a cytidine (C) nucleoside was modified as a bicyclo-sugar, the substituted nucleobase was a 5-methylated cytidine residue. When a uridine (U) nucleoside was modified as a bicyclo-sugar, the substituted nucleobase was a thymine (T) residue. The overhanging nucleotides are as depicted in FIG. 1A-FIG. 1K and are (independently): deoxynucleotides, modified nucleotides, or ribonucleotides. The guide strand was chemically phosphorylated in the case of Format "O." All other 3'-ends and 5'-ends were synthesized to contain hydroxyl groups.

Modified nucleotides introduced into the siRNA molecule included locked nucleic acid (LNA® residues), in particular those having structure (a) above where R1 is O, R2 is O, and R3 is CH$_2$; 2'-O-methyl nucleotide derivatives; and 2'-5' linked nucleotides. LNA® amidites were purchased from Proligo (Boulder, Colo.) and Exiqon A/S (Vedbaek, Denmark), and 2'-O-methyl nucleotide derivatives and 3'- and 2'-TBDMS RNA amidites were purchased from Chemgenes Corporation (Wilmington, Mass.).

Modification formats introduced into siRNAs included those depicted in FIG. 1A (Formats E, F, G, H, J, K, and O in addition to an unmodified control, Format A), FIG. 1B (Formats M, H (repeated), H(−1), H(−2), H(+1), and Q), FIG. 1C (Formats M (repeated), H (repeated) V, V(−1), V(−2), V(+1), FIG. 1D (Formats W, W+1, W−1, Y, Y−1, and Y+1), FIG. 1E (Formats JB1, JB2, JB3, JB4, and JB5), and those depicted in FIG. 1F-FIG. 1K further described in Example 7.

The modification formats included modifications on only the passenger (sense) strand (Formats E, H, K, M, H−1, H−2, H+1, Q, V, V−1, V−2, V+1, W, W+1, W−1, Y, Y−1, Y+1 JB1, JB2, JB3, JB4, JB5, DH3, DH30, and DH28 (See Example 7 for DH formats)) or on both the guide (antisense) strand and the passenger (sense) strand (Formats F, G, J, O, and all DH formats other than DH3, DH30 and DH28 (See Example 7 for DH formats)). The modification formats of FIG. 1A-FIG. 1E are further described below.

| Format | Modified Positions (Numbered from the 5' end of each Strand) | |
|---|---|---|
| | Passenger Sequence | Guide Sequence |
| A, Control | None | None |
| E | 1, 20, 21 | None |
| F | 1, 20, 21 | 20, 21 |
| G | 1, 2, 13, 14 | 9, 10, 19, 20 |
| H | 1, 2, 13, 14 | None |
| J | 1, 2, 10, 14 | 11, 12, 19, 20 |
| K | 1, 2, 10, 14 | None |
| O | 1, 2 | 2 plus a 5'phosphate |
| M | 1, 2 | None |
| H(−1) | 1, 2, 12, 13 | None |
| H(−2) | 1, 2, 11, 12 | None |
| H(+1) | 1, 2, 14, 15 | None |
| Q | 13, 14 | None |
| V | 1, 2, 12, 14 | None |
| V(−1) | 1, 2, 11, 13 | None |
| V(−2) | 1, 2, 10, 12 | None |
| V(+1) | 1, 2, 13, 15 | None |
| W | 2, 3, 13, 14 | None |
| W + 1 | 2, 3, 14, 15 | None |
| W − 1 | 2, 3, 12, 13 | None |
| Y | 1, 3, 13, 14 | None |

-continued

| Format | Modified Positions (Numbered from the 5' end of each Strand) | |
|---|---|---|
| | Passenger Sequence | Guide Sequence |
| Y − 1 | 1, 3, 12, 13 | None |
| Y + 1 | 1, 3, 14, 15 | None |
| JB1 | 1, 2, 14 | None |
| JB2 | 1, 13, 14 | None |
| JB3 | 1, 2, 3, 4, 13, 14 | None |
| JB4 | 1, 2, 3, 13, 15 | None |
| JB5 | 1, 2, 3, 13, 14 | None |

Format F is previously reported by Mook et al. (*Molecular Cancer Therapeutics March*, 2007 6:3, 833-843). Formats E and F are previously reported by Elmen et al. (*Nucleic Acids Research Jan.* 14, 2005. 33:1, 439-447). Format O is described by Jackson et al. (*RNA* May 8, 2006 12:7 1197-1205).

Example 2

Assay Methods for siRNA Silencing Effects

Cleavage activity mediated by the guide (antisense) strand and the passenger (sense) strand of a given siRNA was assayed for exogenously-provided genes as follows. cDNA fragments from genes of interest (GOI) were cloned into the pMIR-REPORT™ miRNA Expression Reporter Vector System (Ambion/Applied Biosystems, Austin, Tex. Cat #AM5795) either in the forward or the reverse orientation with respect to the direction of the coding strand of the DNA for the gene using DNA ligase and standard cloning techniques. The full length cDNA clones were purchased from Open Biosystems (Huntsville, Ala.) for the following GOI.

| Gene ID | Symbol | Description |
|---|---|---|
| 983 | CDC2 | Cell division cycle 2 |
| 1017 | CDK2 | Cyclin-dependent kinase 2 |
| 701 | BUB1B | BUB1 budding uninhibited by benzimidazoles 1 homolog beta |
| 2222 | FDFT1 | Farnesyl-diphosphate farnesyltransferase 1 |
| 3156 | HMGCR | 3-Hydroxy-2methylglutaryl-coenzyme A reductase |
| 7456 | WEE1 | WEE1 homolog (*S. pombe*) |
| 5347 | PLK1 | Polo-like kinase 1 |
| 1213 | CLTC | Clathrin, heavy chain (Hc) |
| 836 | CASP3 | Caspase 3, apoptosis-related cysteine peptidase |
| 595 | CCND1 | Cyclin D1 |
| 1595 | CYP51A1 | Cytochrome P450, family 51, subfamily A, polypeptide 1 |

The coding sequences of the GOI ranged in size from 1.2 kb to greater than 6 kb in length. The cDNA fragment from each GOI was subcloned individually into the HindIII (nucleotide position 463)/SpeI (nucleotide position 525) multicloning site of the pMIR-REPORT™ miRNA Expression Reporter Vector that contains firefly luciferase reporter protein under the control of a mammalian promoter/terminator system as shown in FIG. 2A. Standard PCR-based techniques were used to engineer the HindIII and SpeI restriction endonuclease sites. Reporter vectors were generated that express a mRNA transcript that included the luciferase mRNA fused to the mRNA for the GOI in either the forward or the reverse orientation relative to the fLuc mRNA as shown in FIG. 3A and FIG. 3B. The fLuc-GOI fusion mRNA is expressed under the control of the CMV promoter located closest to the 5' start of the fLuc coding sequences. When the reporter construct is co-transfected into cells with a siRNA complementary to the fLuc or to the cDNA GOI, knockdown as a result of RNA interference is monitored by either measuring the remaining fLuciferase protein or by the remaining fLuc-GOI fusion mRNA. The 5' and 3' terminal 500 nucleotides of all subcloned fragments from each orientation of each GOI were subjected to nucleotide sequence analysis to verify the identity and orientation of the cDNA contained within the vector. Thus, these vectors served as the source of substrate for monitoring siRNA cleavage mediated by either the guide strand (forward clone) or the passenger strand (reverse clone).

The pMIR-REPORT™ Beta-galactosidase Reporter Control Vector (Ambion/Applied Biosystems, Austin, Tex. Cat ##AM5795) depicted in FIG. 2B was used according to the manufacturer's protocol for normalization of transfection efficiency. The β-gal coding sequence is expressed under the control of the CMV promoter. The signal obtained from the fLuc reporter is divided by the signal obtained from the respective β-gal reporter gene to calculate the normalized luciferase activity for each assay.

Transfection:

Hela cells (ATCC No. CCL-2, Manassas, Va.) were plated in 96-well tissue culture plates at a density of about $8.0 \times 10^3$ cells per well. Twenty four hours later, the cells were transfected using standard transfection protocols with siPORT™ Amine Transfection Agent (Ambion/Applied Biosystems Austin, Tex. Cat #AM4502) along with a final concentration of 30 nM of the siRNA under investigation, 40 ng of the pMIR-REPORT™ luciferase-GOI plasmid and 4 ng of the pMIR-REPORT™ transfection control plasmid. Cells were washed with complete media 24 hours post transfection and were collected for analysis 48 hours after transfection. Three biological replicates were tested for each siRNA under investigation for each plasmid. In parallel, Silencer® Negative control siRNA (Ambion/Applied Biosystems, Austin, Tex. Cat #AM4636) was transfected under the same experimental conditions to measure the basal level of expression with a non-targeting siRNA for the purposes of calculating the % of mRNA knockdown by the passenger and guide strands from test siRNA.

Dual-Light® Combined Reporter Gene Assay System:

The Applied Biosystems Dual-Light® combined reporter gene assay system (Applied Biosystems, Foster City, Calif. Cat #T1003) was used to simultaneously detect luciferase and β-gal in the same sample following the manufacturer's recommended protocol. Luminescent readings were taken using a BMG LABTECH POLARstar Optima reader (BMG LABTECH, Durham, N.C.).

Luciferase assays were performed 2-5 seconds following the addition of the luciferin substrate in the Dual-Light® assay system. The plates were allowed to sit for at least 45 minutes before adding substrates for detection and measurement of β-galactosidase. Each well was normalized using the appropriate β-gal reading to obtain a ratio of luciferase signal/β-gal signal. The knockdown or % remaining luciferase expression was then calculated by normalizing the biological samples against the negative control siRNA transfected cells.

Example 3

Silencing Effects of siRNA Modification Formats can be Strand-Switched

For this study, two siRNAs for each of three exogenously-provided target mRNAs were synthesized in the unmodified Format A and for each of 8 different test modification Formats (E, F, G, H, J, K, M and O). Therefore, each test format provides data for 6 siRNAs. For the data of FIG. 4A-FIG. 4E, the modified nucleotides "m" at positions as indicated by the format letter and referring to FIG. 1A and FIG. 1B were LNA® residues having structure (a) above where R1 is O, R2 is O, and R3 is CH$_2$. SiRNA sequences chosen for this study illustrated by FIG. 4A were experimentally determined to have strand silencing activity on the part of both strands. Such a collection allowed an analysis of the impact that a modification has for introducing strand bias, i.e., an ability to impair the silencing activity of one strand while maintaining the activity of the other strand. For this collection of siRNAs, on average, an about 70% knockdown of the luciferase-GOI mRNA mediated by the unmodified guide strand was demonstrated and, on average, an about 58% knockdown of the luciferase-GOI mRNA mediated by the unmodified passenger strand was demonstrated (FIG. 4A, Format A).

The amount of normalized reporter protein present after carrying out RNAi studies for the unmodified Format A and for each test modification Format (E, F, G, H, J, K, M and O) is plotted in FIG. 4A. The dark bars represent the % remaining activity due to silencing by the guide strand since the data result from the clone having the GOI in the forward orientation. The light bars of FIG. 4A represent the % remaining activity due to silencing of the passenger strand since the data result from the clone having the GOI in the reverse orientation. Normalization is carried out by transfection in parallel of a scrambled (nonsense) siRNA, the transfection of which results in a small amount of knockdown for both strands. This reduction in signal (~20%) results in an apparent increase in reporter protein for all normalized results since the normalization is based on a negative value of the nonsense siRNA. This apparent increase is most noticeable for the passenger strand data of modification targets E, F, G, H, J, K, M and O. This model reporter system is useful to detect changes in the activity of the passenger strand and the guide strands.

The data of FIG. 4A demonstrate that guide (antisense) strands of siRNAs having modification Formats E, F, H, K, M and O achieved essentially the same silencing activity as the control Format A guide strands. In the presence of modification Formats G and J, the ability of the guide strands of siRNAs to silence their target was decreased and, in the case of Format J, the ability of the guide strands of siRNAs to silence their target was reduced to less than 20% knockdown activity on average.

While the majority of modification formats depicted by FIG. 4A provided similar guide (antisense) strand mediated cleavage as the unmodified control guide strands, all test modification formats severely impaired the ability of the passenger strands to silence their target essentially rendering the passenger strands inactive for interference activity.

To further examine the effects of modification formats on strand activity, the set of siRNAs used for the strandedness assay was expanded to include a further 18 siRNAs. The data of FIG. 4B-FIG. 4E provide the results of assays of the larger siRNA collection in box plot formats, also referred to as box and whisker plots. For each plot, the dark horizontal bar represents the median value of the dataset for each modification format. The box represents the distribution of the data at the lower quartile and the upper quartile of the dataset for each modification format while the dotted lines (whiskers) represent the smallest and largest values of the dataset for each modification format. The circles represent likely outliers in the dataset for each modification format.

The activity of the passenger strand following transfection in Hela cells of siRNAs of this larger siRNA set is provided by FIG. 4B. Activity is calculated using the following formula: P (passenger strand activity)=(fLUC remaining from reverse clone treated with test siRNA β-gal activity)/(fLUC remaining from reverse clone treated with Neg control siRNA β-gal activity). The data of FIG. 4B demonstrate a loss of activity of the passenger strands of modified siRNA formats as seen by the upward shift of the median passenger strand knockdown activity when compared to that of Format A. The data for modification formats G, H, J, K, M and O were statistically significant (p<0.05), thereby demonstrating that the modification formats were efficient at reducing the activity of the passenger strand.

The activity of the guide strand following transfection in Hela cells of the set of siRNAs analyzed for FIG. 4B is provided by FIG. 4C. Activity is calculated using the following formula: G (guide strand activity)=(fLUC remaining from forward clone treated with test siRNA β-gal activity)/ (fLUC remaining from forward clone treated with Neg control siRNA/β-gal activity). Formats E, F, H, M, and O did not negatively impact the activity of the guide strand (i.e., "do no harm"). Format E appears to increase the ability of the guide strand to reduce the luciferase signal in a statistically significant manner indicated by the downward shift in the median guide strand activity compared to the unmodified Format A. Modification formats G, J and K reduced the activity of the guide strand as evidenced by the upward shift in the median values for those formats (p<0.05) compared to the unmodified siRNAs of Format A.

The data of FIG. 4D provide the difference of fLUC activity between the passenger and the guide strands of FIG. 4B and FIG. 4C using the following formula: Activity Difference=P−G (using the definitions of P and G as set forth above). Since the fLUC reporter assay measures the amount of fLuciferase activity following siRNA transfection in cells, more active siRNA strands knock down more of the respective fLUC reporter mRNA and result in lower relative amount of luciferase activity. Thus, if the passenger strand is less active than the guide strand, the values of this activity difference calculation will be greater than 0. If the passenger strand is more active than the guide strand, the values will be less than 0. Modification Format J reduced the activity difference between the two strands of the test siRNAs.

The data of FIG. 4E provide the fold change of activity between the passenger strand and the guide strand for siRNAs of FIG. 4B and FIG. 4C. The activity fold change was calculated as $\log_2(P)-\log_2(G)$ using the definitions of P and G as set forth above. A value of 0 describes a siRNA for which each strand has equal silencing capability. The larger the activity fold change, the greater the guide strand bias of the siRNA. A comparison of the box plots of FIG. 4E demonstrates that the strand bias between the passenger strand and the guide strand is significantly enhanced for modification formats E, H, M and O (p<0.05) when compared to that of the control unmodified siRNA Format A. Thus, siRNAs having modification Formats E, H, M and O displayed increased strandedness as compared to the unmodified Format A. Formats G, J and K demonstrated a lower fold difference between passenger and guide strand, but only Format J significantly reduced the fold change of activity compared to Format A. The largest individual strand bias was demonstrated by Format H.

A study was carried out to test the ability of the modification formats to affect the silencing activity of highly potent siRNA strands by strand-switching (SW) the modification formats from passenger strand to guide strand and from guide strand to passenger strand for each modification format. That is, for modification Format $F_{SW}$ of FIG. 5A, for example, the modifications of Format F at positions 1, 20, and 21 of the passenger (sense) strand (FIG. 1A) were introduced into the guide (antisense) strand, and the modifications of Format F at positions 20 and 21 of the guide (antisense) strand (FIG. 1A) were introduced into the passenger (sense) strand.

The data of FIG. 5A provide results of a strand assay where the amount of normalized reporter protein present after carrying out RNAi studies is plotted for 12 siRNAs having unmodified siRNA Format A and the same 12 siRNAs having the modifications of the strands switched as compared to those of FIG. 4A. The set of siRNAs studied for the FIG. 5A data differs from the set studied for the FIG. 4A data in that the siRNAs for the FIG. 5A data have a strand bias as evidenced by the large difference in the % of fLUC signal remaining between the guide and passenger strand of the unformatted Format A siRNA. The experimental conditions that were used to measure knockdown in this "strand-switching" assay were the same as those used to generate the data of FIG. 4A.

As provided by the data of FIG. 5A, the silencing activity of the guide strands was dramatically reduced due to the strand-switched modifications. On average, the guide strands having strand-switched modification formats achieved knockdown by less than 20%. Strand-switched modification Format $H_{SW}$ was one of the most potent modification formats to inactivate the guide (antisense) strand for this collection of siRNAs.

The test passenger strands having strand-switched modification formats provided variable results. However, all test passenger strands having strand-switched modification formats were more effective at knockdown than in the unmodified siRNAs of Format A in FIG. 5A. While not wanting to be bound by theory, it is possible that, as a result of impairing the potency of the guide strand, the potency of the passenger strands is indirectly or secondarily enhanced as suggested by the enhanced knockdown achieved by the passenger strands in the strand-switched modified formats.

FIG. 5B provides the data of FIG. 5A in a box plot format, which format is described above as for FIG. 4D. Thus, if the activity of the passenger strand is less than the activity of the guide strand, the difference would be expected to be greater than 0, which is demonstrated by modification Format A, for which the median activity difference is approximately 0.65 for this collection of siRNA. The strand-switched modification formats have difference activities less than 0 indicating that Formats $H_{sw}$, $M_{sw}$, $F_{sw}$, $E_{sw}$ and $O_{sw}$ switched the strandedness to favor the passenger strand rather than the guide strand compared to the unmodified Format A. The greatest enhancement of strandedness was observed for strand-switched modification Format $M_{sw}$ which has a median activity difference of ~−0.5.

The fold change of activity ($\log_2(P)-\log_2(G)$) between the passenger strand and the guide strand for the siRNAs of FIG. 5B is provided for each modification format in FIG. 5C. These results indicate that a modification format that confers knockdown activity to a guide strand and essentially inactivates a passenger strand, when strand-switched, can reduce knockdown activity of a guide strand and increase knockdown activity of a passenger strand.

A study similar to that of FIG. 4A and FIG. 4D (using LNA® modified nucleotides) was carried out using various modification formats where the modified nucleotides were 2'-O methylated. For this study, two siRNAs for each of three target mRNAs were synthesized in the unmodified Format A and in each test format. Therefore, each test format provides data for 6 siRNAs. As for the studies of FIG. 4A, the particular siRNA sequences chosen for this study are those for which both strands of the unmodified Format A siRNA demonstrated silencing. The guide (antisense) strand of unmodified siRNAs, on average, reduced the target mRNA by 70% while the passenger (sense) strand reduced the target mRNA by 55%.

With regard to passenger (sense) strand activity, the data of FIG. 6A demonstrate that essentially all mRNA product is available for the luciferase assay after 48 hours incubation with the siRNA in culture. That is, the test siRNAs having modification formats where the modified nucleotides are 2'-O methylated demonstrate significant loss of potency of the passenger (sense) strand as indicated by the increase in the % remaining gene expression in these samples. This passenger strand inactivity for knockdown is consistent with the data for the modification formats using LNA® modified nucleotides. Also consistent with the data for the LNA® modification Formats H, K, and O, the potency of the guide strands having modification Formats H, K, and O with 2'-O-methyl nucleotides was essentially unchanged as compared to unmodified control Format A. Thus, the modification formats with 2'-O-methyl modified nucleotides appear to be as effective in maintaining the activity of the guide (antisense) strand while disabling the cleavage activity of the passenger (sense) strand in these strand assays for which the target is exogenously-provided.

FIG. 6B provides the data of the siRNAs studied for FIG. 6A (6 siRNAs) plus an additional 18 siRNA sequences in a box plot format. The activity difference of the Format A group indicates that the majority of the siRNAs are biased towards the guide strand (indicated by the median value located at about 0.5). However, siRNAs generated with 2'OMe in the modification formats indicated demonstrate a larger difference between the passenger strand and the guide strand as compared to the control Format A. Formats H and H+1 induced the largest difference between the strands. Format O with 2'-OMe modified bases failed to increase the activity difference between the strands.

The activity fold change of the passenger strand compared to the guide strand is provided in FIG. 6C, calculated as previously described. The fold change analysis indicated that Format H provides the largest fold change compared to unmodified siRNAs of Format A. However, significant fold changes in activity between the strands was also observed by Formats H−1, H, H+1, V−2 and K, but not by Format O as determined by the Wilcoxon values cited in the figure legend for FIG. 6C.

A third type of modified nucleotide was studied in various modification formats. FIG. 7A provides results of strand assays in which modified nucleotides of modification formats were 2',5'-linked nucleotides. The activity difference of the fLuc signal from pMIR-REPORT™ studies of GOI cloned in the forward and reverse orientation, thereby representing the difference in guide and passenger strand efficacy and knockdown activity, is plotted for unmodified Format A and test Formats H−1, H, H+1, V−2, K and O. A comparison of the strandedness results for the unmodified control Format A to the results for the test formats containing 2',5'-linked bases indicated that no statistically significant changes in the strandedness of the siRNA were obtained by including 2',5'-linked base modifications with the exception of Format O. Format O with 2'-5'-linked base modifications decreased the activity difference indicating a loss of knockdown activity for the guide strand in a statistically significant manner.

The activity fold change between the passenger strand and the guide strand is provided by FIG. 7B calculated as previously described. The fold change analysis indicated that Format O containing the 2'-5' linked nucleic acids influenced the strandedness of the siRNA in a negative direction as indicated by the decrease in the fold change of activity between the passenger strand and the guide strand. Further, data from the 2'-5' linked nucleic acids in formats H−1, H+1, V−2, and K are not statistically significant and therefore, these formats are not suitable to improve the strandedness of the siRNAs. Only Format H modified with 2'-5' base modifications demonstrated a statistically significant increase in strandedness as demonstrated by the Wilcoxon values cited in the figure legend for FIG. 7B.

A statistical analysis on the difference in cleavage activity of the guide versus the passenger strand demonstrated that the greatest change in strand bias was introduced by the LNA® and 2'OMe modified nucleotides in modification Format H based on the data of FIG. 4A and FIG. 6A. The strandedness analysis also demonstrated that Format G, Format J and Format K decreased the activity of the guide strand in a statistically significant manner, thus they were dropped from subsequent consideration for enhancing siRNA specificity. Format H with LNA® modified nucleotides induced on average an 8-fold difference in cleavage activity of the guide strand over the passenger strand as evidenced by the data of FIG. 4A. By comparison, the unmodified control Format A demonstrates, on average, a 4-fold increased activity of the guide strand over the passenger strand. Thus, the Format H modification doubled the strand bias that normally exists in an optimally designed siRNA.

In addition, these data demonstrated that the strand-switched formats having LNA® modified residues were capable of inactivating the guide strand as efficiently as they inactivated the passenger strand.

The data for FIG. 12A-1 and FIG. 12A-2 represent knockdown activity of 12 siRNAs generated to contain LNA® modified nucleotides in the indicated formats. The strandedness of the test group indicates that the majority of the siRNAs are asymmetrically biased toward the higher activity guide strand (indicated by the median difference of activity of 0.5 for Format A of FIG. 12A-1). However, siRNAs generated with the modification formats and LNA® residues demonstrated a larger difference between the passenger strand and the guide strand activity as compared to unmodified Format A. The Format H modification format enhanced the activity difference between the strands in a statistically significant manner, but the fold change of activity was not significant as shown by the data for FIG. 12A-2.

The data for FIG. 13A-1 and FIG. 13A-2 represent siRNAs generated to contain 2'OMe modified nucleotides in the indicated formats. The strandedness of the test group indicates that the majority of the siRNAs are asymmetrically biased toward the higher activity guide strand as evidenced by the median difference of activity of 0.5 of FIG. 13A-1. However, siRNAs generated with 2'OMe modified nucleotides demonstrate a larger fold change between the passenger strand and the guide strand as compared to the unmodified control Format A as shown by FIG. 13A-2. Formats H, K, and V−2 induced the largest and statistically significant fold change between the strands (p<0.05). Data for all formats, with the exception of Format O, were statistically significant as compared to the unmodified siRNA.

Example 4

Effects of siRNA Modification Formats on Silencing of Endogenous Genes

Silencing of endogenous genes by modification formatted siRNA was tested to determine if the modification formats altered the efficacy of the siRNA to knock down its mRNA target. For this study, knockdown of endogenous genes was tested by transfection of modification-formatted siRNAs at low concentration into Hela cells (ATCC No. CCL-2, Manassas, Va.), U2OS cells (a human osteosarcoma cell line, ATCC No. HTB-96), and HUH7 cells (a human hepatoma cell line, #JCRB 0403, Japanese Cancer Research Resource Bank, Tokyo, Japan). The Hela cell data are discussed herein.

Hela cells were transfected using the siPORT™ NeoFX™ Transfection Agent (Ambion/Applied Biosystems Austin, Tex. Cat #AM4510) using the "reverse" transfection protocol described by the manufacturer. Unmodified control or modification-formatted siRNA was plated into 96-well tissue culture plates to achieve a final concentration of either 1 nM or 5 nM. SiPORT™ NeoFX™ transfection agent was complexed with siRNA for at least 10 minutes, followed by overlaying freshly trypsinized Hela cells (~4.0×10$^3$ cells) on the siRNA/transfection agent complex. The plates were incubated under tissue culture conditions at 37° C. for 48 hours.

U2OS cells were transfected using HyPerFect® Transfection Agent (Qiagen, Gaithersberg, Md.) using the "forward" transfection protocol described by the manufacturer. Unmodified control or modification-formatted siRNA was plated into 96-well tissue culture plates to achieve a final concentration of either 3 nM or 30 nM. HyPerFect® transfection agent was complexed with siRNA for at least 10 minutes and the complex was added to U2OS cells in culture (about 4.0×10$^3$). The plates were incubated under tissue culture conditions at 37° C. for 48 hours.

After harvesting transfected cells, total RNA was isolated using the MagMAX™-96 total RNA isolation kit (Ambion, Inc. Austin, Tex. Cat. #AM1830) according to the manufacturer's protocol. RNA was eluted in 50 µl of nuclease-free water. cDNA was generated using the High Capacity cDNA Reverse Transcription Kit (Applied Biosystems, Inc. Foster City, Calif., Cat. #4368814) according to the manufacturer's protocol in a 30 µl reaction volume. TaqMan® Gene Expression Assays (Applied Biosystems, Inc., Cat. #4331182) were carried out using 2 µl of cDNA in a 10 µl total PCR reaction volume. Technical replicates were generated and an 18S value was calculated for each sample. Preamplification uniformity was checked by calculating the ddCT using the formula described above.

The % remaining was calculated using the formula: % remaining=$100 \times 2^{-(ddCT)}$.

The fraction of mRNA knockdown was calculated using the following formula:

$$\text{fraction of mRNA knockdown} = 1 - (2^{-(ddCT)})$$

and $$\text{\% mRNA knockdown} = \text{fraction of mRNA knockdown} \times 100.$$

For this knockdown study, six siRNAs for each of eight endogenous target mRNAs were synthesized in unmodified Format A and for each of the 8 test modification Formats E, F, G, H, J, K, M and O. Therefore, each test format provides data for 48 siRNAs. For the data of FIG. 8 the modified nucleotides "m" at positions as indicated by the format letter and referring to FIG. 1A-FIG. 1C were LNA® residues having structure (a) above where R1 is O, R2 is O, and R3 is CH$_2$.

FIG. 8 provides data for silencing the endogenous mRNA targets in Hela cells at 5 nM final concentration of modification-formatted siRNA and assaying the % knockdown of the target 48 hours after transfection using TaqMan® Gene Expression Assays. The results from these studies demonstrate that the modification-formatted LNA®-containing siRNAs in Formats G, J and K compromise the knockdown activity of the siRNA, while the modification-formatted LNA®-containing siRNAs in Formats E, F, H, M and O maintain or increase knockdown compared to that observed for the unmodified Format A group. Thus, several modification formats having LNA® residues in various positions did not negatively impact the knockdown activity of the siRNA but were sufficient to enhance the strandedness of the guide strand vs. the passenger strand. The knockdown activity of the siRNAs in this collection of LNA® modified siRNAs was also determined in human hepatoma cells (HUH7), and human osteosarcoma cells (U2OS). In these cell lines, the LNA® modified siRNA of each modification format displayed similar knockdown activity to that observed in HeLa cells taking into account different transfection efficiencies (data not shown). Therefore, silencing performance was not affected by the type of cell line used.

Further knockdown activity data are provided by FIG. 12B for modification Formats H, H–2, H–1, H+1, Q, K, V, V–1, and V–2 using LNA® modified nucleotides. This dataset represents 24 different siRNAs targeting 4 different endogenous mRNA targets. Each of the 24 siRNAs was synthesized in each format and the knockdown of the siRNAs in each group was analyzed identically. Transfection was into Hela cells at 5 nM final concentration with the assays carried out 48 hours after transfection using TaqMan® Gene Expression Assay. The results demonstrate a slight decrease in the knockdown activity of the siRNAs in formats K and V–2 that is not statistically significant from the unmodified siRNA. Modification formats H, H–1, H–2, H+1, Q, V and V–1 maintained or increased the knockdown activity of mRNA targets when compared to that observed for the unmodified siRNA group.

The data of FIG. 13B provide knockdown activity for modification Formats H, H+1, H–1, K, V–2, and O using 2'OMe modified nucleotides. This dataset represents 24 different siRNAs targeting 4 different endogenous mRNA targets. Each of the 24 siRNAs was synthesized in each format and the knockdown of the siRNAs in each group was analyzed identically. Transfection was into Hela cells at 5 nM final concentration with the assays carried out 48 hours after transfection using TaqMan® Gene Expression Assay. The results demonstrate that modification formats H, H+1, H–1, K, V–2, and O maintain or increase knockdown as compared to that observed for the unmodified Format A siRNAs.

Further data are provided by FIG. 14A for modification Formats H, M, W, W+1, W–1, Y, Y+1, and Y–1 using LNA® modified nucleotides compared to Format A. This dataset represents 15 different siRNAs targeting 5 different endogenous mRNA targets. Each of the 15 siRNAs was synthesized in the indicated formats and the knockdown of the siRNA in each group was analyzed identically. Transfection was into U2OS cells at a final concentration of 30 nM with the assays carried out 48 hours after transfection using the TaqMan® Gene Expression Assay. The results demonstrate that siRNAs having modification Formats W, W+1, W–1, Y, Y+1, and Y–1 modified with LNA® residues maintain knockdown activity when compared to that of unmodified siRNA Format A. SiRNAs having modification Format M are compromised in knockdown activity when compared to that of siRNAs having unmodified Format A, and siRNAs having modification Format H improve knockdown activity when compared to that of unmodified Format A, both in a statistically significant manner.

Data of FIG. 14B provide knockdown activity for modification Formats H, M, JB1, JB2, JB3, JB4, and JB5 using LNA® modified nucleotides compared to Format A. This dataset represents 15 different siRNAs targeting 5 different endogenous mRNA targets. Each of the 15 siRNAs was synthesized in the indicated formats and the knockdown of the siRNA in each group was analyzed identically. Transfection was into U2OS cells at a final concentration of 30 nM with the assays carried out 48 hours after transfection using TaqMan® Gene Expression Assay. The results demonstrate that siRNAs having modification Formats JB2, JB3, and JB5 are not statistically significantly different than unmodified Format A in terms of knockdown activity; siRNAs having Format H, JB1, and JB4 improve knockdown activity when compared to Format A and siRNAs having Format M have less knockdown activity when compared to Format A.

Of the siRNA modification formats examined in this example, Formats G, J, K and M compromise knockdown activity when compared to the unmodified format.

Example 5

Effects of siRNA having Modification Format H on Global Gene Expression Profiling as a Measure of Off-Target Effects The ability of the LNA® and 2'-O-methyl modified nucleotides in Format H to influence the signature of differentially expressed genes was compared to that of unmodified siRNA by measuring the gene profile using a microarray analysis. Microarray genome analysis was carried out on quadruplicate biological samples transfected with 4 siRNAs designed to target the FDFT1 gene. FDFT1 is a gene that is involved in cholesterol biosynthesis and not essential to the cells that are used for the testing. This criterion ensures that the differences in gene expression that are detected by array analysis are solely the results of cleavage mediated by the siRNA rather than a result of any biological cascades that result from the loss of the functional mRNA target.

Each of three siRNA sequences (designated siRNA #183, #184 and #192) was separately transfected in the unmodified Format A, LNA® modified Format H and 2'-O-methyl modified Format H into Hela cells using standard procedures as outlined above and transfected cells were harvested 24 hours later. RNA was isolated using standard procedures for microarray analysis. Affymetrix U133 V2 microarray chips (Affymetrix, Santa Clara, Calif.) containing human probesets were used for these studies. Controls included a negative control siRNA, "mock" transfected cells, and nontreated cells to record baseline levels of gene expression in the absence of experimental treatment. Following normalization of the data, the results were analyzed to determine the identity of the genes that were changed by 2-fold or greater in each of the sample sets as compared to the mock (delivery agent only) control sample results. A 1-way ANOVA with planned contrasts was then used to determine the p-values for each mock-treated vs. experimental condition. The differentially expressed gene probe sets were then defined as 2-fold changes with p<0.001. The number of differentially expressed genes is a measure of off-target effects due to the siRNA.

FIG. 9A-FIG. 9C provide Venn diagrams of the results for siRNA #183 (FIG. 9A), siRNA #184 (FIG. 9B) and siRNA #192 (FIG. 9C), three distinct siRNAs designed to target the FDFT1 gene. Each diagram depicts results for one of three siRNAs in unmodified, 2'-O-methyl or LNA® modified siRNAs as indicated. The Venn diagrams indicate the number of specific genes that were changed in each experimental condition and the intersection of the genes between siRNA conditions. For each diagram, the lower left set (red if in color) indicates the number of specific genes changed 2-fold or greater in the unmodified siRNA treated samples, the upper set (blue if in color) indicates the number of specific genes changed 2-fold or greater in the 2'-O-methyl Format H modified siRNA treated samples, and the lower right set (green if in color) indicates the number of specific genes changed 2-fold or greater in the LNA® Format H modified siRNA treated samples.

For siRNA #183 (FIG. 9A), the unmodified siRNA induced a 2-fold or greater decrease in the mRNA levels of 31 genes (2+19+10+0). The 2'-O-methyl modified siRNA induced a 2-fold or greater decrease in the mRNA levels of 32 genes (3+0+10+19), 29 of which were also affected by the unmodified control siRNA. Samples treated with 2'-O-methyl modified siRNA differed from the unmodified siRNA in the number of off-target genes by only 3 genes. The LNA® modified siRNA induced a 2-fold or greater decrease in the mRNA levels of 10 genes (0+0+10+0), all of which are also altered by the unmodified control and the 2'-O-methyl modification. Therefore, those 10 genes represent off-target effects that are sequence-dependent and cannot be alleviated by the teachings provided herein. Thus, the LNA® modification format had the more significant impact on the removal of off-target gene expression changes (a 68% decrease in off-target effects) as compared to the 2'-O-methyl modification (a 0% decrease in off-target effects).

For siRNA #184 (FIG. 9B), the unmodified siRNA induced a 2-fold or greater decrease in the mRNA levels of 70 differentially expressed genes in Hela cells (14+23+33+1). The 2'-O-methyl modified siRNA induced a 2-fold or greater decrease in the mRNA levels of 66 genes (9+1+33+23). In contrast, the LNA® modified siRNA reduced the number of differentially expressed genes by 50% (35 genes (0+1+33+1)) compared to the unmodified siRNA results. The vast majority of the differentially expressed genes in the LNA® modified treated samples (33 genes) were also identified as differentially expressed in unmodified and 2'-O-methyl modified siRNA treated samples. Such genes represent off-target effects that are sequence-dependent and cannot be alleviated by the teachings provided herein. Thus, the LNA® modification format again had the more significant impact on the removal of off-target gene expression changes (a 50% decrease in off-target effects) as compared to the 2'-O-methyl modification (a 6% decrease in off-target effects).

For siRNA #192 (FIG. 9C), the unmodified siRNA induced a 2-fold or greater decrease in the mRNA levels of 103 differentially expressed genes (28+13+61+1). The 2'-O-methyl modified siRNA induced a 2-fold or greater decrease in the mRNA levels of 81 genes (7+0+61+13). The LNA® modified siRNA induced a 2-fold or greater decrease in the mRNA levels of 64 genes (2+1+61+0). Thus, the LNA® modification removed ~38% of the off-target effects compared to the unmodified siRNA. For this siRNA, 61 genes represent off target effects that are sequence-dependent and cannot be alleviated by the teachings provided herein. The LNA® modification format again had the more significant impact on the removal of off-target gene expression changes (a 38% decrease in off-target effects) as compared to the 2'-O-methyl modification (a 21% decrease in off-target effects).

In summary, the microarray analyses demonstrated that LNA® modified Format H siRNA produced 38% to 68% fewer differentially expressed genes when compared to unmodified Format A siRNA and the 2'-O-methyl modified Format H siRNA produced 0% to 22% fewer differentially expressed genes when compared to unmodified Format A siRNA. Therefore, the LNA® modified Format H siRNA provided the least number of off-target effects.

Example 6

Performance of Modification-Formatted siRNAs in Cell Biology Studies

Cell biology studies were carried out to gauge the ability of the modification formats and the types of modified nucleotides to impact the on-target and the off-target phenotypes evoked by the siRNAs.

In order to determine if modification-formatted siRNAs maintain the "on-target" or desired phenotype and alleviate the "off-target" or undesired phenotype, siRNAs were chosen that induced a measurable and highly characterized biological response. Thus, the preservation of the on-target phenotype was monitored in addition to removal of the off-target phenotype. SiRNAs were synthesized with the test modification formats and transfected into the appropriate cells for assays as described below.

An assay, termed herein a "growth assay," was carried out to investigate the differences in modification-formatted siRNAs compared to unmodified siRNA and negative control siRNA at the cellular level. The growth assay included measuring cell phenotype-related parameters such as proliferation, apoptosis and morphologies in an U2OS osteosarcoma cell line following siRNA transfection at 30 nM and at 3 nM. The results from the 30 nM assays are discussed herein since more off-target effects are observed at the higher concentration of siRNA and, therefore, the barrier for removing such off-target effects is higher. The growth assay analysis included immunofluorescence detection of the following antigens which are markers for the indicated phenotype:
 1. Cleaved lamin-A (apoptosis),
 2. Phosphorylated Histone H3 (mitosis),
 3. Tubulin (cytoskeletal morphology which is a quality control measurement, i.e., a background determination for the structure of the cell and which marks all cells), and
 4. Hoescht stain (nuclear morphology which provides cell number normalization).

Immunofluorescence was collected using a 10× objective powered by robotically controlled image acquisition software (Cellinger, Munich, Germany) and the METAMORPH® image analysis software package (Molecular Devices, Toronto, Canada) using the IMAGEXPRESS$^{Micro}$™ automated fluorescence microscope (Molecular Devices, Toronto, Canada). Four positions in each 384 well sample were collected, the data were averaged across three biological replicates and compared to negative siRNA control samples (scrambled non-targeting siRNA) treated in a similar manner. Following image analysis, data are evaluated according to the following protocol:
 1) Index calculation: for each site within a well, the number of mitotic nuclei and apoptotic nuclei was normalized against the total number of nuclei and the area of non-cell background was subtracted from the total image area to calculate the area occupied by cells, and then normalized against the number of nuclei;
 2) Sample well average calculation: the average of all sites within a well was calculated and, additionally, all sites of all negative control wells per plate were averaged;
 3) Normalization: samples and positive controls for each plate of a triplicate were normalized against the average of negative siRNA control wells;
 4) Triplicate average calculation: the average of the plate triplicates was calculated for each treatment and readout.

Test genes were chosen that are well characterized functionally in various cells by published literature. The test genes included those of Table 1.

TABLE 1

| mRNA target | | | Expected on-target phenotype due to knockdown of the gene product | |
|---|---|---|---|---|
| Gene description | Gene symbol | Gene ID | Apoptosis | Mitosis |
| BUB1 budding uninhibited by benzimidazoles 1 homolog beta | BUB1B | 701 | Neutral | Decrease |
| WEE1 homolog (S. pombe) | WEE1 | 7465 | Increase | Increase |
| Cell division cycle 2 | CDC2 | 983 | Neutral | Decrease |
| Cyclin-dependent kinase 2 | CDK2 | 1017 | Neutral | Decrease |
| Cyclin D1 | CCND1 | 595 | Neutral | Decrease |
| Polo-like kinase 1 | PLK1 | 5347 | Increase | Increase |
| Caspase 3 | CASP3 | 836 | Neutral | Neutral |
| Farnesyl-diphosphate farnesyltransferase 1 | FDFT1 | 2222 | Neutral | Neutral |
| Low Density lipoprotein receptor | LDLR | 3949 | Neutral | Neutral |
| Sterol-C5-desaturase (ERG3 delta-5-desaturase homolog, S. cerevisiae)-like | SC5DL | 6309 | Neutral | Neutral |

SiRNAs were identified that provided a strong measurable induction of an expected phenotype, e.g., a 300% increase in mitosis following knockdown of Wee1 or PLK1 (Watanabe, N. et al. (2004) *PNAS*, 101, 4419-4424; Leach, S. D. et al. (1998) *Cancer Research*, 58, 3132-3136; Cogswell, J. P. et al. (2000) *Cell Growth and Diff.* 11, 615-623). Knockdown of the BUB1B gene is expected to decrease the % of mitosis compared to Neg control (Lampson, M. A. and Kapoor, T. M. (2004) *Nature Cell Biology*, 7, 93-98).

Additionally, siRNAs were identified that displayed an off-target phenotype. For example, siRNAs to LDLR, a gene not expected to induce apoptosis (see Table 1 for other such genes), demonstrated a 500% increase in apoptosis. Such siRNA sequences served as tools to determine if modification formats could improve the specificity of the siRNA. Separate sets of siRNAs with observable on-target phenotypes and off-target phenotypes were generated to contain several modification formats, and either 2'-O-methyl modified nucleotides or LNA® residues having structure (a) above where R1 is O, R2 is O, and R3 is CH$_2$. These modified siRNAs were tested for the on-target and the off-target phenotypes to determine those modification formats that could remove the off-target effects while maintaining the on-target phenotype.

The modification-formatted siRNA cell-based assay results are plotted as box and whiskers plots in FIG. 10A-FIG. 10E, FIG. 11A-FIG. 11F, FIG. 12C-FIG. 12D, FIG. 13C-FIG. 13D, FIG. 15A-15D, and FIG. 16A-FIG. 16D relative to the normalized values for the negative control siRNA treated samples analyzed in parallel in the cell-based assays (labeled as Neg in said figures).

A box plot of normalized mitotic cells resulting from silencing by siRNA having LNA® modification Formats E, F, G, H, J, K, M and O is provided by FIG. 10A. The siRNAs targeted BUB1B, WEE1, CDC2, CDK2, CASP3, and CCND1, genes that include disparate effects on mitosis phenotype. That is, this set of genes includes a subset that increases mitosis when silenced, a subset that decreases mitosis when silenced, and a subset that is expected to have no effect on mitosis when silenced. Because of these disparate effects, a subset of the genes, knockdown of which provides the expected phenotype of a decrease in mitosis, was analyzed and the data provided in FIG. 10B.

The FIG. 10B data show normalized mitotic cells following transfection of siRNAs targeting genes, knockdown of which is expected to decrease mitosis (BUB1B, CDC2, CCND1) (Lampson, M. A. and Kapoor, T. M. (2004) *Nature Cell Biology*, 7, 93-98; Harborth, J. et al. (2001) *Journal of Cell Science* 114, 4557-4565; Klier, M. (2008) *Leukemia*, EPUB). These data therefore measure an on-target phenotypic effect, that is, this assay ensures that the modification formatted siRNAs "do no harm" to a functioning set of siRNAs. The normalized values for Neg control treated samples show a median value of about 1.0. The unmodified Format A siRNAs provided a median value of about 0.55 indicating an about 2-fold decrease in mitosis. All modification formats provided for a mitosis decrease as compared to Neg control. SiRNAs having modification Formats H and J provided a statistically significant difference in their effect on mitosis (less on-target effect) as compared to unmodified Format A as evidenced by the Wilcoxon values and the shift away from unmodified Format A by the median value for mitosis. Thus, consistent with the results regarding mRNA knockdown of FIG. 8, cell-based assays demonstrate that Format J is not compatible with the desired characteristics of a highly functional siRNA.

The cell-based growth assay also measured apoptosis compared to Neg control treated samples by quantitating the fluorescent signal from cells displaying cleaved lamin-A (Rao, L. et al. (1996) *J Cell Biology*, 135, 1441-1455). Historically, the most prevalent unexpected phenotype observed in genome-wide siRNA screening experiments is cell death. In this collection of siRNA for these studies, siRNA sequences were included that were known to induce unexpected cell death as a tool to determine if the modification format could remove the unwanted cellular phenotype.

The results of quantitating the apoptotic fragments due to treating U2OS cells with siRNA having LNA® modification Formats E, F, G, H, J, K, M and O are provided by FIG. 10C. Neg control siRNA treated samples were used to establish a baseline of apoptosis following transfection of siRNA and the data were normalized to 1.0. The siRNA in this collection target the following genes: BUB1B, CDC2, CCND1, WEE1 CASP3, and CDK2, a set of gene targets, the knockdown of a subset of which is expected to increase apoptosis and a subset of which is expected to have no effect on apoptosis. Because of these disparate effects, a subset of the genes, knockdown of which provides the expected phenotype of an increase in apoptosis, was analyzed and the data provided in FIG. 10D.

FIG. 10D provides the results of apoptosis measurements in the U2OS cells following transfection of siRNA targeting WEE1. Knockdown of WEE1 is expected to increase apoptosis (Watanabe, N. et al. (2004) *PNAS*, 101, 4419-4424; Leach, S. D. et al. (1998) *Cancer Research*, 58, 3132-3136). These data therefore measure an on-target phenotypic effect, that is, this assay ensures that the modification formatted siRNAs "do no harm" to a functioning set of siRNAs. Neg control siRNA treated samples were used to establish the normalized baseline of apoptosis. Unmodified siRNA of Format A targeting WEE1 displayed a median of approximately 7.5 compared to NEG treated samples, thereby providing the expected phenotypic change. Modification-formatted siRNA having Formats J and K reduced the on-target phenotype by reducing the amount of apoptosis in a statistically significant manner when compared to the unmodified Format A siRNA demonstrating that Formats J and K compromise the performance of the siRNA. These data are consistent with those of FIG. 8 regarding knockdown by siRNAs having modification Formats J and K.

Analysis of the ability of modification formatted siRNAs to remove an off-target phenotype for a subset of genes, knockdown of which is expected to have no effect on apoptosis, is provided by the data of FIG. 10E. SiRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median and greater distribution of data as compared to the Neg control (FIG. 10E). The siRNA studied have Formats A, E, F, G, H, J, K, M and O and the target genes, knockdown of which is not expected to induce apoptosis, included BUB1B, CCND1, CDK2, and CDC2. The Neg control treated population was used to establish the baseline for apoptosis. SiRNA having Formats G, H, J and K demonstrate a statistically significant ability to remove off-target effects as evidenced by the lower apoptotic signal compared to the unmodified Format A (FIG. 10E).

In light of the data of FIG. 10D where siRNA having modification Formats J and K were demonstrated to compromise the siRNA on-target efficacy and in light of the data of FIG. 8 where siRNA having modification Formats G, J, and K were demonstrated to compromise knockdown activity, Formats G, J, and K appear to "do harm" to an otherwise functioning siRNA.

Further characterization of the modification formats was carried out by using modified nucleotides containing 2'-O-methylated residues instead of LNA® residues to determine if other types of modifications could reduce off-target effects by siRNAs. FIG. 11A provides a box plot of normalized mitotic cells resulting from silencing by siRNAs having 2'-O-methyl modification Formats H and K and targeting WEE1, PLK1, FDFT1, LDLR, and SC5DL, genes that include disparate effects on mitosis phenotype. That is, this set of genes includes a subset that increases mitosis when silenced, and a subset that is expected to have no effect on mitosis when silenced. Because of these disparate effects, a subset of the genes, knockdown of which provides the expected phenotype of an increase in mitosis, was analyzed and the data provided in FIG. 11B.

FIG. 11B provides the results of mitosis measurements in U2OS cells following transfection of siRNA targeting WEE1 or PLK1 by siRNA having 2'-O-methyl modification Formats H and K. That silencing of WEE1 or PLK1 results in an increase of mitosis in U2OS cells is provided by Watanabe, N. et al. ((2004) *PNAS,* 101, 4419-4424), Leach, S. D. et al. ((1998) *Cancer Research,* 58, 3132-3136), and Cogswell, J. P. et al. ((2000) *Cell Growth and Diff.* 11, 615-623) and confirmed by the data for siRNAs having unmodified Format A, which induced an about 4-fold increase in mitosis compared to the Neg control treated samples. These data therefore measure an on-target phenotypic effect, that is, this assay ensures that the modification formatted siRNAs "do no harm" to a functioning set of siRNAs. As shown by the data of FIG. 11B, similar levels of impact on mitosis are observed using siRNAs having 2'OMe modification Formats H and K. This study demonstrates that the 2'OMe modification in the Formats H and K do no harm to an otherwise functioning siRNA.

To determine if siRNAs having 2'OMe modification Formats H and K could reduce off-target effects, siRNAs targeting a subset of genes (FDFT1, SC5DL and LDLR), knockdown of which is expected to have no effect on mitosis, were transfected into the U2OS cells and the impact on mitosis was determined. However, siRNAs that have empirically demonstrated mitosis off-target effects were specifically chosen for study to determine if such siRNAs, when modification-formatted, would eliminate or reduce the off-target effects. Data are provided by FIG. 11C. That the siRNAs have off-target effects is evidenced by the box plot for unmodified Format A which has a greater distribution of data as compared to the Neg control (FIG. 11C). SiRNA having 2'OMe residues in Format H reduced many of the off-target phenotypes observed in the unmodified siRNA Format A when individual siRNA sequences were compared. SiRNAs having 2'OMe residues in Format K raised the median mitotic impact compared to the unmodified siRNA. However, data for this 2'-O-methyl modification in Formats H and K were not statistically significantly different from the data of unmodified Format A.

The results of quantitating apoptotic fragments due to treating U2OS cells with siRNA having 2'-O-methyl modification Formats H and K are provided by FIG. 11D. Neg control siRNA treated samples were used to establish a baseline of apoptosis following transfection of siRNA and the data were normalized to 1.0. The siRNA in this collection target genes WEE1, PLK1, FDFT1, LDLR, and SC5DL, knockdown of a subset of which is expected to increase apoptosis and a subset of which is expected to have no effect on apoptosis. Because of these disparate effects, a subset of the genes, knockdown of which provides the expected phenotype of an increase in apoptosis, was analyzed and the data provided in FIG. 11E.

FIG. 11E provides the results of apoptosis measurements in the U2OS cells following transfection of siRNA targeting WEE1 and PLK1 by sets of 12 siRNAs having 2'-O-methyl modification Formats H and K. These data therefore measure an on-target phenotypic effect, that is, this assay ensures that the modification formatted siRNAs "do no harm" to a functioning set of siRNAs. Neg control siRNA treated samples were used to establish the normalized baseline of apoptosis. Unmodified siRNA of Format A targeting WEE1 or PLK1 displayed a median of greater than about a 4-fold increase in apoptosis compared to NEG treated samples, thereby providing the expected phenotypic change. Similar levels of apoptosis were observed with 2'OMe modified siRNA in Format H and Format K. This study demonstrates that 2'OMe modifications in the H and K formats do not reduce the efficacy of the siRNA and provide similar phenotypes as observed in the unmodified siRNA Format A.

Analysis of the ability of 2'-O-methyl modification formatted siRNAs to remove an off-target phenotype for a set of genes, FDFT1, LDLR, and SC5DL, knockdown of which is expected to have no effect on apoptosis, is provided by the data of FIG. 11F. SiRNAs that have empirically demonstrated apoptosis off-target effects were specifically chosen for study to determine if such siRNAs, when modification-formatted, would eliminate or reduce the off-target effects. The siRNA studied have Formats A, H and K. The Neg control treated population was used to establish the baseline for apoptosis and has a particularly broad range of apoptosis results. The median value for the control Format A was similar to that of the Neg control treated samples. SiRNAs having 2'OMe modified nucleotides in modification Formats H and K reduced many of the off-target phenotypes observed in the unmodified siRNA Format A when individual siRNA sequences were evaluated, but over the test population, the reduction of the off-target effects was not observed in a statistically relevant manner.

Further modification formats were tested as set forth in the schematic of FIG. 1A-FIG. 1C that provide Formats H, H-2, H-1, H+1, Q, V, V-1, V-2 and K. The LNA® modified nucleotides had structure (a) where R1 and R2 are O, R3 is CH2, and R4 and R5 are as determined by the position of the nucleotide in the siRNA as described herein. The on-target phenotype assay for mitosis (i.e., the "do no harm" assay) in U2OS cells was carried out for the siRNA modification formats of FIG. 12C. As shown by the data of FIG. 12C, unmodified siRNA demonstrated an about 2-fold increase in mitosis in siRNA treated cells compared to Neg control treated cells. The on-target performance of the modification-formatted siRNAs modified by LNA® in these formats did not negatively impact the expected phenotype. Modification Format H provides a statistically significant gain in phenotype.

FIG. 12D provides data regarding removal of off-target effects for siRNAs having the LNA® modification formats of FIG. 12C. A box plot of normalized apoptotic fragments resulting from silencing by siRNA having unmodified Format A and for LNA® modification Formats H, H+1, H−1, H−2, K, Q, V, V−1, and V−2, for a set of gene targets, the knockdown of which is expected to have no effect on apoptosis (FDFT1, LDLR or SC5DL). The negative control (Neg) is a scrambled non-targeting siRNA for which apoptosis quantitation is normalized to a value of 1.0. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median and greater distribution of data as compared to the Neg control. The modification formats that were most effective at removing the unwanted apoptosis phenotype were Formats H, K, Q, and V−2 while modification Formats H−2, H−1, H+1, V, and V−1 did not alter the apoptotic fragments measurement with any statistical significance as compared to unmodified siRNA.

SiRNAs modified by 2'OMe nucleotides for modification formats H, H−1, K, and V also do not negatively impact the on-target phenotype in U2OS cell-based assays as shown by the data of FIG. 13C. FIG. 13C provides a box plot of normalized mitotic cells resulting from silencing by siRNA having unmodified Format A and for said modification formats having 2'-O-methyl modified nucleotides for a set of gene targets, the knockdown of which is expected to increase mitosis (WEE1 and PLK1). This assay is a "do no harm" assay. Unmodified siRNA demonstrated a median value for mitosis of ~2-fold greater than the Neg control treated samples as expected. The data for the modification formatted siRNA demonstrate that siRNA having 2'OMe modified nucleotides do not negatively impact the expected phenotype in cell-based assays.

FIG. 13D provides a box plot of normalized apoptotic fragments resulting from silencing by siRNAs having unmodified Format A and for siRNAs having modification Formats H, H−1, V and K having 2'-O-methyl modified nucleotides for a set of gene targets, the knockdown of which is expected to have no effect on apoptosis (FDFT1, SC5DL or LDLR). However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has greater distribution of data as compared to the Neg control. The set of siRNAs contained 13 different siRNAs for each format. None of the siRNAs having 2'OMe modification formats provided data that are statistically significantly different from unmodified control Format A demonstrating that the 2'OMe modification formatted siRNA maintained the same off-target effects observed for the unmodified Format A siRNA.

Further modification formats similar to that of Format H and as set forth in FIG. 1D were studied. FIG. 15A provides box plots of normalized mitotic cells for siRNAs having LNA® modified nucleotides in Formats A, H, M, W, W+1, W−1, Y, Y+1, and Y−1. The siRNA set was chosen to knockdown BUB1B, CCND1, and CDC2 mRNAs to result in an expected decrease of the mitotic index of U2OS cells. These data therefore measure an on-target phenotypic effect, that is, this assay ensures that the modification-formatted siRNAs "do no harm" to a functioning set of siRNAs. As provided by the data of FIG. 15A, the median mitotic value for samples treated with unmodified Format A siRNA demonstrated a decrease in mitosis to approximately 0.75 compared to the Neg control siRNA treated samples. Modification-formatted siRNA in Formats H, M, W+1, W−1, Y−1 and Y+1 do not significantly change the impact of these siRNA on mitosis demonstrating that these modification formats "do no harm." However, modification Formats Y and W reduced the expected on-target impact of the siRNAs demonstrating that these modification formats interfere with on-target function.

FIG. 15B provides a box plot as for FIG. 15A for CASP3, knockdown of which is not expected to affect mitosis. However, siRNAs that have empirically demonstrated mitosis off-target effects were specifically chosen for study to determine if such siRNAs, when modification-formatted, would eliminate or reduce the off-target effects. That the siRNAs have off-target effects is evidenced by the box plot for unmodified Format A which has a median value of about 0.7 as compared to the Neg control. SiRNAs having modification Formats H, W, W+1, W−1, Y, and Y+1 reversed the off-target effects demonstrated by siRNAs of Format A. Modification of siRNA with Formats M and Y−1 did not reverse the off-target phenotypes of the Format A siRNAs. None of the Wilcoxon values provided a $p<0.05$ for the data of FIG. 15B, possibly due to the small population of siRNAs in each format.

Box plots of normalized apoptotic fragments for a set of siRNAs targeting the WEE1 gene, knockdown of which is expected to increase apoptosis, for Formats A, H, M, W, W+1, W−1, Y, Y+1, and Y−1 are provided by FIG. 15C. Unmodified Format A siRNA show a median apoptotic value greater than 4.0 compared to Neg control siRNA treated samples demonstrating a robust increase in apoptosis as a consequence of WEE1 knockdown. The test data therefore measure an on-target phenotypic effect, that is, this assay ensures that the modification-formatted siRNAs "do no harm" to a functioning set of unmodified siRNAs. As provided by the data of FIG. 15C, siRNA having modification Formats H, M, and W−1 show similar increases in apoptosis as compared to Format A, whereas Formats W, W+1, Y, Y+1 and Y−1 demonstrate a lesser impact on apoptosis compared to the unmodified siRNA Format A. None of the Wilcoxon values provided a $p<0.05$ for the data of FIG. 15C, possibly due to the small population of siRNAs in each format. Despite the reduced apoptosis impact, the chemical modification Formats W, W+1, Y, Y+1 and Y−1 maintain the ability to knock down the target mRNA (FIG. 14A) and to induce apoptosis compared to the Neg control siRNA treated samples.

Box plots of normalized apoptotic fragments for a set of gene targets, knockdown of which is not expected to impact apoptosis, are provided by FIG. 15D for siRNAs having modification Formats A, H, M, W, W+1, W−1, Y, Y+1, and Y−1. The siRNA in this set target BUB1B, CCND1, CDC2, or CDK2. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has a median value of greater than 3.5 and greater distribution of data as compared to the Neg control. Silencing by siRNA having Formats H, Y, and Y+1 show statistically significant reversal of off-target effects as compared to Format A.

Even further siRNA modification formats as set forth in FIG. 1E were studied. The siRNAs were transfected into U2OS cells and the mitosis effects were measured as described herein. FIG. 16A provides box plots of normalized mitotic cells for siRNAs having unmodified Format A and for LNA® modification Formats H, M, JB1, JB2, JB3, JB4 and JB5. The siRNA set (3 siRNAs per target mRNA) was chosen to knockdown BUB1B, CCND1, and CDC2 mRNAs to result in an expected decrease of the mitotic index of U2OS cells. These data therefore measure an on-target phenotypic effect, that is, this assay ensures that the modification-formatted siRNAs "do no harm" to a functioning set of siRNAs. As provided by the data of FIG. 16A, the median mitotic value for samples treated with unmodified Format A siRNA demonstrated a decrease in mitosis to approximately 0.75 compared to the Neg control siRNA treated samples. Modification-formatted siRNA in Formats H, M, JB1, JB2, JB4 and JB5 do not significantly change the on-target impact of the siRNA on mitosis demonstrating that these formats are tolerated by siRNA. However, siRNA having modification Format JB3 significantly reduced the expected on-target impact of the siRNAs targeting these genes, demonstrating that Format JB3 interferes with on-target function.

FIG. 16B provides a box plot for modification formats as for FIG. 16A for a gene target, CASP3, knockdown of which is not expected to affect mitosis. However, siRNAs that have empirically demonstrated mitosis off-target effects were specifically chosen for study to determine if such siRNAs, when modification-formatted, would eliminate or reduce the off-target effects. That the siRNAs have off-target effects is evidenced by the box plot for unmodified Format A which has a median value of about 0.65 thereby displaying a decrease in mitosis as compared to the Neg control. Modification Formats H, JB1, JB2, JB4 and JB5 were able to reverse these off-target effects as demonstrated by the data of FIG. 16B. Modification Formats M and JB3 did not reduce the off-target phenotypes of the siRNAs targeting CASP3, demonstrating that these formats are not effective at removing off-target phenotypes. None of the Wilcoxon values provided a p<0.05 for the data of FIG. 16B, possibly due to the small population of siRNAs in each format.

Box plots of normalized apoptotic fragments resulting from silencing the gene target, WEE1, the knockdown of which is expected to increase apoptosis, are provided by FIG. 16C for siRNAs having modification Formats A, H, M, JB1, JB2, JB3, JB4 and JB5. These data therefore measure an on-target phenotypic effect, that is, this assay ensures that the modification-formatted siRNAs "do no harm" to a functioning set of siRNAs. As provided by the data of FIG. 16C, the median apoptotic value for samples treated with unmodified Format A siRNA demonstrated an increase in apoptosis to >4.0 compared to the Neg control siRNA treated samples demonstrating a robust increase in apoptosis as a consequence of WEE1 knockdown. SiRNAs having the modification formats induced the expected phenotype to varying degrees demonstrating that all formats tested do no harm to a set of functional siRNA. None of the Wilcoxon values provided a p<0.05 for the data of FIG. 15B, possibly due to the small population of siRNAs in each format.

FIG. 16D provides a box plot for modification formats as for FIG. 16C for the set of gene targets containing BUB1B, CCND1, CDC2, and CDK2, knockdown of which is not expected to have an effect on apoptosis, for siRNAs having LNA modified nucleotides in Formats A, H, M, JB1, JB2, JB3, JB4 and JB5. However, siRNAs that have empirically demonstrated apoptosis off-target effects were specifically chosen for study to determine if such siRNAs, when modification-formatted, would eliminate or reduce the off-target effects. That the siRNAs have off-target effects is evidenced by the box plot for unmodified Format A which has an increased median value of greater than 3 and greater distribution of data as compared to the Neg control treated samples. As shown by the data of FIG. 16D, siRNA having modification Formats H, JB1, JB2, JB3, JB4 and JB5 are able to reverse the apoptosis off-target effects when compared to that of Format A in a statistically significant manner. SiRNAs having Format M are not able to reverse the apoptotic effect to a statistically significant degree.

When taken together, the data of FIGS. 10E, 11C, 11F, 12D, 13D, 15B, 15D, 16B, and 16D demonstrate that those modification formats that provide for an unexpected reduction of off-target phenotypic effects include Formats G, H, J, K, Q, V–2, Y, Y+1, JB1, JB2, JB3, JB4, and JB5. Of those modification formats, Formats G, J, and K "do harm" to the ability of otherwise functional siRNA to knock down activity. Highly functional siRNAs have the properties of reducing off-target phenotypic effects and, in addition, "do no harm" in terms of knockdown activity. Modification formats that provide such high functionality to otherwise functional siRNAs include Formats H, Q, V–2, Y, Y+1, JB1, JB2, JB3, JB4, and JB5.

Those modification formats that were studied both for strandedness effect (data of FIG. 4E, 6C, 7B, 12A, 13A, Example 3 herein) and were studied for their ability to confer a reduction of off-target effects as provided above provide an assessment of whether one can predict, from the strandedness assay, how a modification formatted siRNA will behave in removal of off-target effects. The strandedness data of Example 3 using classic reporter assays demonstrate that modification Formats E, G, H, K, O and M would be expected to perform well in cellular phenotypic assays. In fact, three of these formats did perform well and three of them did not. Therefore, strandedness assays appear to be ineffective at predicting whether a modification formatted siRNA will be functional at achieving a desired cellular phenotype.

Example 7

Stabilized Modification-Formatted siRNAs

The present example provides modification-formatted siRNAs that are particularly stable to exposure to biological fluids containing nucleases in addition to maintaining the properties of knockdown activity and removal of off-target effects discussed above. Elmen et al. (*Nucleic Acids Research* 33:1, 439-447, 2005) reportedly describe a stabilized siRNA termed siLNA5 that has the same modification format as Format F herein and which format is used as a reference control for stability studies for the present example. The term "stable to exposure to biological fluids," as used herein, means that the siRNAs maintains their full-length in the presence of a biological fluid containing nucleases to the same or greater degree as compared to siRNAs having modification Format F exposed to the same biological fluid for the same period of time.

While the present example provides stabilized modification formats, modification-formatted siRNAs as provided by previous examples are suitable for use in circumstances where nuclease activity is of minimal concern.

Regarding Format F, the data from Example 6 and FIG. 10E demonstrate that siRNAs having modification Format F are substantially ineffective in removing off-target cellular effects.

Studies were carried out on 8 different siRNA sequences targeting the CLTC and WEE1 mRNAs to determine those modification formats that confer stability to the siRNAs in 90% mouse blood serum. Synthesis of siRNA was carried out as described in Example 1 for modification formats described below and set forth by FIG. 1F-FIG. 1K.

| Format | Modified Positions (Numbered from the 5' end of each Strand) | |
|---|---|---|
| | Passenger Sequence | Guide Sequence |
| A, Control | None | None |
| F (Elmen et al.) | 1, 20, 21 | 20, 21 |
| H | 1, 2, 13, 14 | None |
| DH21 | 1, 2, 13, 14 | 20, 21 |
| DH20 | 1, 2, 13, 14 | 19, 20, 21 |
| DH3 | 1, 2, 13, 14, 20, 21 | None |
| DH30 | 1, 2, 13, 14, 19, 20 | None |
| DH35 | 1, 2, 13, 14, 20 | 21 |
| DH6 | 1, 13, 14, 21 | 21 |
| DH34 | 1, 2, 13, 14, 20, 21 | 21 |
| DH2 | 1, 2, 13, 14, 20, 21 | 20, 21 |
| DH19 | 1, 2, 13, 14, 19, 20 | 19, 20, 21 |
| DH4 | 1, 2, 13, 14, 19, 20 | 19, 20 |
| DH31 | 1, 2, 13, 14, 19, 20 | 20, 21 |
| DH27 | 1, 2, 7, 13, 14, 19, 20 | 20, 21 |
| DH25 | 1, 2, 6, 9, 13, 14, 19, 20 | 20, 21 |
| DH47 | 1, 2, 13, 14, 19, 20, 21 | 20, 21 |
| DH29 | 1, 2, 13, 14, 18, 20, 21 | 20, 21 |
| DH28 | 1, 2, 13, 14, 18, 20, 21 | None |
| DH18 | 1, 2, 13, 14, 18, 20, 21 | 19, 20, 21 |
| DH36 | 1, 2, 20, 21 | 20, 21 |
| DH9 | 1, 2, 13, 14, 20 | 20, 21 |
| DH46 | 1, 2, 13, 14, 21 | 20, 21 |
| DH33 | 1, 2, 13, 14, 20, 21 | 20 |
| DH10 | 1, 2, 13, 14, 20 | 20 |
| DH7 | 1, 2, 20, 21 | 2, 20, 21 |
| DH23 | 1, 2, 13, 14 | 2, 20, 21 |
| DH1 | 1, 2, 13, 14, 20, 21 | 2, 20, 21 |
| DH48 | 1, 2, 13, 14, 20, 21 | 2, 20 |
| DH49 | 1, 2, 13, 14, 20, 21 | 2, 21 |
| DH44 | 1, 2, 13, 14, 20 | 2, 20, 21 |
| DH45 | 1, 2, 13, 14, 21 | 2, 20, 21 |
| DH38 | 1, 2, 13, 14, 20, 21 | 1, 20, 21 |
| DH39 | 1, 2, 13, 14, 20, 21 | 3, 20, 21 |
| DH40 | 1, 2, 13, 14, 20, 21 | 4, 20, 21 |
| DH41 | 1, 2, 13, 14, 20, 21 | 5, 20, 21 |
| DH42 | 1, 2, 13, 14, 20, 21 | 6, 20, 21 |
| DH43 | 1, 2, 13, 14, 20, 21 | 7, 20, 21 |

Modified nucleotides introduced into the modification-formatted siRNAs were locked nucleic acid (LNA® residues), in particular those having structure (a) above where R1 is O, R2 is O, and R3 is $CH_2$.

The stability assay, as used herein, provides the amount of full-length product present after incubation of modification-formatted siRNA in 90% mouse serum that had not been heat inactivated (cat #44135, JR Scientific, Inc., Woodland, Calif.). All siRNAs were treated with the identical lot of mouse serum that had been validated as having robust nuclease activity prior to use. Similar results were obtained using human serum (cat #CC-5500, SeraCare Life Sciences, Inc., Oceanside, Calif.) and fetal bovine serum (cat #5V30014, HyClone, Logan, Utah) (data not shown).

For each assay, 10 µM of modification-formatted siRNA in 50 µL final volume was incubated at 37° C. in 90% mouse serum for either the time indicated in the time course (FIG. 17) or for a period of 5 hours (FIG. 18A-FIG. 23B). Parallel to the incubation in serum, each set of siRNAs was treated with PBS (cat #9625, Applied Biosystems, Austin, Tex.) for the same period of time as the serum-treated samples to establish a baseline for the amount of full-length product for HPLC studies. Following incubation, the siRNAs were extracted with phenol (cat #9700, Applied Biosystems, Austin, Tex.) and ethanol precipitated in the presence of 5 µg glycogen carrier (1 µl/tube, Catalog No. AM9510, Applied Biosystems, Austin, Tex.) to enhance recovery of small RNAs. SiRNA and cleavage products were recovered by centrifugation (15 min at 15,000×g) and dissolved in PBS buffer (phosphate-buffered saline) prior to HPLC analysis.

Determination of the amount of full-length product was carried out using ion-exchange high performance liquid chromatography (HPLC) using a continuous gradient of sodium perchlorate ($NaClO_4$) containing acetonitrile. The stationary phase was a Dionex DNAPAC® 200 column (4 mm×250 mm, Dionex Corporation, Sunnyvale, Calif.) used with a Waters 2795 ALLIANCE® analytical HPLC system and EMPOWER™ Dissolution Software v2 (Waters Corp, Milford, Mass.). The temperature was maintained such that the siRNA duplex would not denature. Quantitation and UV detection is performed at 254 nm via the Waters 2998 photodiode array detector (Waters Corp, Milford, Mass.). A siRNA (21-mer duplex with two overhanging 3' nucleotides on each end) targeting the mRNA for GAPdH (10 µM) in a 10 µl-20 µl injection volume is used to ascertain column quality and retention times. Analysis of the HPLC results was based on the area counts of the peaks for untreated siRNA taken as 100%, and the area counts of the peaks with the same retention time (+/−0.1-0.2 min) for the serum-treated samples providing a calculated remaining percentage.

The same siRNAs tested for serum stability were tested separately for knockdown activity of endogenous genes to determine if the modification formats altered the efficacy of the siRNA to knock down its mRNA target. Modification-formatted siRNAs and unmodified control siRNAs were transfected into Hela cells at a final concentration of 5 nM as described in Example 4 with the exception that the transfection used Lipofectamine™ 2000 (Invitrogen, Carlsbad, Calif.) in the "forward" protocol described by the manufacturer. After harvesting transfected cells, total cell lysate was isolated using the TaqMan® Gene Expression Cells-to-CT™ kit (Applied Biosystems, Inc. Cat. #AM1728) according to the manufacturer's protocol. Preparation of cDNA, gene expression assays, and calculation of knockdown activity were carried out as in Example 4.

Degradation in serum of unmodified forms of the 8 different siRNAs of the present study is demonstrated by the data of FIG. 17 where, within 5 to 10 min of exposure to serum, greater than 50% of the full length molecule is degraded.

A box plot of the percentage of siRNAs that remain full length when treated with 90% blood serum for 5 hours under described conditions is provided by FIG. 18A for unmodified Format A, stability control Format F, and modification formats H, DH21, DH20, DH3, DH30, DH35, DH6, DH34, and DH2. Unmodified Format A and modification Format H were completely degraded in serum under the conditions described. Stability reference control Format F has a median value of about 43% full length siRNA in serum under the conditions described. Analysis of the data of FIG. 18A indicates modification of nucleotides at and/or near only one of the 3'-termini is insufficient to protect the modified siRNA in serum (Formats DH21, DH20, DH3 and DH30 as compared to Format F). Modification of two or three of the overhanging nucleotides is also insufficient to protect the modified siRNA in serum (Formats DH6, DH34 and DH35 as compared to Format F). Format DH2 having all four overhanging nucleotides modified provide protection in serum equal to or better than Format F. FIG. 18B provides a box plot of mRNA knockdown as a % of Neg control for the siRNAs studied for FIG. 18A. As shown by FIG. 18B, unmodified Format A siRNAs display a median knockdown of ~85% compared to Neg control siRNA treated samples. SiRNA modification Format DH2O particularly shows a decrease in knockdown activity as compared to that of Format H. Of this set of modification formats studied, only Format DH2 is considered for further analysis due to its stability and knockdown activity.

Providing two modified nucleotides in the penultimate and antepenultimate positions of the 3'-terminus of the sense strand together with modified nucleotides in two or three of the terminal residues of the antisense strands (DH4, DH31, DH19) appears to have a detrimental effect on serum stability as exhibited by FIG. 19A. These data further support positioning modified nucleotides as the overhanging nucleotides. Moreover, as shown by the data of FIG. 19B, Formats DH19, DH27 and DH25 show a significant decrease in knockdown activity compared to Format A. Format DH31 possessed knockdown activity of >70%. Protection of internal residues (as for DH27 (position 7) and DH25 (positions 6 and 9)) while leaving terminal residues unprotected appears counterproductive with regard to knockdown ability when the data are compared to that of Format DH2.

The data provided by FIG. 20A demonstrate an increase in stability for modification Formats DH47 and DH29 and an even further increase in stability for DH18 as compared to control Format F. Modification Formats DH47 and DH29 provide for modified nucleotides at one of the antepenultimate and preantepenultimate positions of the sense strand sequence (i.e., for a 21-mer, one of positions 18 and 19) in addition to modified nucleotides in the overhanging positions and positions of Format H. Format DH18 provides for modified nucleotides as for DH29 and, in addition, provides a modified nucleotide at the antepenultimate position of the antisense strand (i.e., for a 21-mer, position 19). The data for Format DH28, when compared directly to Format DH29, demonstrates again that lack of modified nucleotides at the overhanging positions of the antisense strand knocks out the stability provided by the protected sense strand. When compared to Format F, data for Format DH47 and DH28 have a Wilcoxon value where p<0.05. The data of FIG. 20B demonstrate that Formats DH47, DH 29, and DH28 possess knockdown activity of >70%. Modification of the antepenultimate position of the antisense strand (position 19) as in Format DH18, while providing enhanced stability, compromises knockdown activity to a median of about 60%. Based on the above data, Formats DH47 and DH29 both provide increased stability of siRNA over control Format F, Format DH47 provides knockdown activity comparable to that of unmodified Format A and Format DH29 provides knockdown activity of greater than 70%.

None of the siRNAs having modification formats depicted in FIG. 21A provide a serum stability increase over siRNAs having modification Format F or Format DH2. The lack of added serum stability further supports a modification format where the overhanging nucleotides are modified. The knockdown activity data for the siRNAs studied for FIG. 21A all demonstrate >70% activity as shown by FIG. 21B.

A comparison of serum stability of siRNAs having modification Format F to that of siRNAs having modification Formats DH23, DH48, DH49, DH44, and DH45 of FIG. 22A further supports modified nucleotides at positions of the overhanging nucleotides. Modification of the nucleotide at position 2 of the antisense strand, in addition to having modified nucleotides in the positions of the overhanging nucleotides, such as for Format DH1 and DH7 increases the median for stability in serum (FIG. 22A). Data of FIG. 22B demonstrate that all formatted siRNAs of FIG. 22A, with the exception of Format DH23, achieve greater than 70% knockdown activity. Taken together, Formats DH1 and DH7, having a modified nucleotide at position 2 of the guide strand in addition to positions of overhanging nucleotides, provide both properties of serum stability and knockdown activity. SiRNAs having modification Format DH7 lack modified nucleotides in the positions at and near 13 and 14 and, therefore, may not provide the property of removing off-target effects. However, such siRNAs may be useful for silencing in circumstances where off-target effects are not expected.

The data provided by FIG. 23A examine the effect of a one nucleotide modification at positions 1, 2, 3, 4, 5, 6, or 7 of the antisense strand (position #1 is the 5' nucleotide) in addition to modified nucleotides of Format H and at the overhanging positions (DH38, DH1, DH39, DH40, DH41, DH42, DH43, respectively). The data demonstrate that median serum stability is increased by all of the formatted siRNAs tested with a trend to decreasing stability as the modified nucleotide is positioned further away from the 5' end of the guide antisense strand.

As provided by the data of FIG. 23B, all formatted siRNAs have knockdown activity of greater than 70% with the exception of siRNAs having Format DH38. This observation highlights the incompatibility of a modified nucleotide positioned at the 5'-end of the antisense strand. Addition of a phosphate group to the 5' end of the antisense strand partially rescued biological activity, but at the cost of reduced stability (data not shown). Taken together, the data on serum stability and knockdown demonstrate that an at least one nucleotide modification at positions 2, 3, 4, 5, 6, or 7 of the guide antisense strand (with reference to the 5'-end) enhances siRNA stability while also providing knockdown activity of at least 70%.

Taking the data of FIG. 18A-FIG. 23B together, those modification formats that provide serum stability greater than Format F while maintaining knockdown activity of at least 70% are Formats DH47, DH29, DH7, DH1, DH39, DH40, DH41, DH42 and DH43.

Format DH7 lacks modified nucleotides in the positions at and near positions 13 and 14 and, therefore, may not provide the property of removing off-target effects.

Formats DH47, DH29, DH1, DH39, DH40, DH41, DH42 and DH43 have modified nucleotides in the passenger sense strand at positions 1, 2, 13, 14, 20, 21, and, for DH47 and DH29 one of positions 18 or 19; and have modified nucleotides in the guide antisense strand at positions 20 and 21, and, for DH39-DH43 any one of positions 2, 3, 4, 5, 6, or 7. A duplexed base pair where both of the nucleotides are modified at position 1 of the passenger sense strand appears detrimental to knockdown activity (DH20, DH19, DH4, DH18).

Example 8

In Vivo Delivery of Stabilized siRNAs

Unmodified Format A siRNA and stabilized siRNAs having modification Formats DH1 and DH47 were delivered in vivo, and the amounts of full-length siRNA present in livers from control and test animals were compared. The TaqMan® based stem-loop RT-PCR assay that allows reliable and robust quantification of siRNAs and miRNAs and specifically detects only full-length molecules was used for analysis (U.S. Published Patent Application 2005/0266418 to Chen et al., filed Sep. 21, 2004; Chen, C. et al. *Nucleic Acids Research* 33, e179, 2005).

SiRNAs targeting the Fas gene were administered to mice (1 nmol diluted in 2.5 ml PBS (10% of mouse body weight)) using hydrodynamic (high-pressure) tail vein injection as described by Zhang et al. (*Human Gene Therapy* 10, 1735-1737. 1999) and Lewis et al. (*Nature Genetics* 32, 107-108. 2002). Four mice were injected for each modification-formatted siRNA. The modified nucleotides were LNA® residues having structure (a) where R1 is O, R2 is O, and R3 is $CH_2$.

Five minutes post-injection, the mice were sacrificed and whole livers were harvested and frozen in dry ice. Total RNA was isolated from whole livers using the mirVana™ PARIS™ Kit (Applied Biosystems, Foster City, Calif.) according to the manufacturer's protocol with modifications as follows. Cell disruption buffer (20 ml) was added and the samples were homogenized. Lysates (400 µl) were transferred to new tubes, denaturing solution (400 µl) was added to each tube and the tubes were mixed well by vortexing. Phenol extractions were carried out by adding 800 µl phenol, vortexing for 5 min, and centrifuging for 10 min. The upper phase (300 µl) was transferred into new tubes and mixed with 375 µl (1.25 vol) 100% ethanol. The mixture was passed through filter columns according to the protocol for the kit with a final elution of 100 µl elution buffer. RNA concentrations were measured and adjusted to 10 ng/µl.

The assays for quantification of siRNAs included reverse transcription (RT) of the guide strand of the siRNA using the RT primer having a stem-loop design as described for the TaqMan® MicroRNA Reverse Transcription Assays (Applied Biosystems, Foster City, Calif.) followed by PCR. In a 10 µl RT reaction, 1 ng/µl of total RNA and 50 nM of RT primer were denatured at 85° C. for 5 min, then 60° C. for 5 min, and then annealed at 4° C. After adding the enzyme mix (0.25 mM each of the dNTPs, final concentration; 3.33 units/µl of MultiScribe™ reverse transcriptase (Applied Biosystems), 1×RT buffer, 0.25 units/µl of RNase inhibitor), the reaction mixture was incubated at 16° C. for 30 min, 42° C. for 30 min, 85° C. for 5 min, and then 4° C. Real-time PCR was performed using a standard TaqMan® PCR protocol on an Applied Biosystems 7900HT Sequence Detection System (Applied Biosystems). The 10 µl PCR reaction mixture included 1 µl RT product, 1× TaqMan® Universal PCR Master Mix, 0.2 µM TaqMan® probe, 1.5 µM forward primer, and 0.7 µM reverse primer. The reaction was incubated at 95° C. for 10 min, followed by 40 cycles of 95° C. for 15 sec and 60° C. for 1 min Frozen whole livers from a separate control untreated group of mice were spiked, prior to homogenization, with 300, 200, 100 and 50 pmol of siRNA. These "spiked" samples serve as a control for the study and provide a standard curve for comparison of cycle threshold values (Ct) between the injected and the control samples. RNA was isolated from the control organs as described above. The term "Ct" represents the PCR cycle number when the signal is first recorded as statistically significant. Thus, the lower the Ct value, the greater the concentration of nucleic acid target. In the TAQMAN® assay, typically each cycle almost doubles the amount of PCR product and therefore, the fluorescent signal should double if there is no inhibition of the reaction and the reaction was nearly 100% efficient with purified nucleic acid.

FIG. 24 provides the Ct values for the "spiked" controls, the unmodified Format A injected animals, and the Format DH1 and Format DH47 siRNA-treated animals. About 5% of the unmodified Format A siRNA was detected in the liver 5 minutes after hydrodynamic injection. In contrast, about 20% of the modification-formatted siRNA having Formats DH1 and DH47 were detected, a 400% increase compared to unmodified siRNA. This in vivo study demonstrates that siRNAs that are modification-formatted for stabilization provide for significantly increased delivery of full-length siRNA upon systemic administration.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

The invention claimed is:

1. A chemically synthesized short interfering RNA comprising:
    a chemically synthesized passenger oligonucleotide having a length of 15 to 30 nucleotides and comprising: sequence-independent modification format (1):
        (1) 5' $N_p$-m-m-$N_x$-m-m-$N_q$-$n_r$ 3', wherein p is 0; x is 10; r is 0, 1, or 2; and q is an integer representing the length of the passenger strand minus (p+x+r+4);
    wherein
    each m is independently a bicyclo nucleotide or a tricyclo nucleotide;
    each n is independently a deoxynucleotide, modified nucleotide, or ribonucleotide;
    when m is a bicyclo nucleotide, each N is independently a nucleotide other than a bicyclo nucleotide, and
    when m is a tricyclo nucleotide, each N is independently a nucleotide other than a tricyclo nucleotide
    and
    a guide oligonucleotide having 15 to 30 nucleotides including a region of continuous complementarity to the passenger oligonucleotide of at least 12 nucleotides,
    the guide oligonucleotide further having complementarity to at least a portion of a target mRNA.

2. The chemically synthesized short interfering RNA of claim 1 wherein the passenger oligonucleotide comprises sequence-independent modification format (1), p is 0, x is 10 and r is 2.

3. The chemically synthesized short interfering RNA of claim 1 wherein the passenger oligonucleotide and the guide oligonucleotide are covalently bonded via a nucleotide loop or a linker loop to form a short hairpin oligonucleotide.

4. The chemically synthesized short interfering RNA of claim 1 wherein the short interfering RNA comprises a plurality of internucleoside linkages and wherein at least one internucleoside linkage is not a phosphodiester internucleoside linkage.

5. The chemically synthesized short interfering RNA of claim 1 wherein the chemically synthesized short interfering RNA is further associated with a cell-targeting ligand.

6. A composition comprising the chemically synthesized short interfering RNA of claim 1 and a biologically acceptable carrier.

7. A kit comprising the chemically synthesized short interfering RNA of claim 1 and a transfection agent.

8. A method of minimizing off-target events for inhibition of expression of a target gene by RNA interference, comprising: contacting a cell containing the target gene with the chemically synthesized short interfering RNA of claim 1 in an amount sufficient to reduce off-target events while maintaining potency.

9. The method of claim 8 wherein the gene is an endogenous gene.

10. The method of claim 8 wherein the contacting is in vitro contacting of a cell culture containing the cell, or a tissue containing the cell with the chemically synthesized short interfering RNA.

11. The method of claim 8 wherein the contacting is ex vivo contacting of a tissue containing the cell, a bodily fluid containing the cell, or an organ containing the cell with the chemically synthesized short interfering RNA.

12. The chemically synthesized short interfering RNA of claim 1 wherein at least one m has structure (a), (b), or (c):

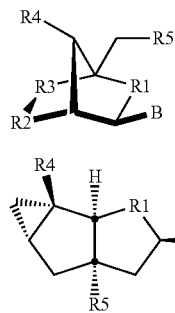

(a)

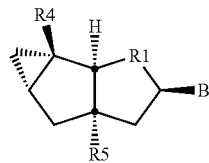

(b)

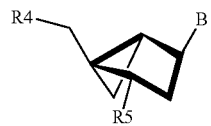

(c)

wherein

R1 and R2 are independently O, S, $CH_2$, or NR where R is hydrogen or $C_{1-3}$-alkyl;

R3 is $CH_2$, $CH_2$—O, $CH_2$—S, $CH_2$—$CH_2$, $CH_2$—$CH_2$—$CH_2$, CH=CH, or $CH_2$—NR where R is hydrogen or $C_{1-3}$-alkyl;

R4 and R5 are independently an internucleoside linkage, a terminal group, or a protecting group;

at least one of R4 and R5 is an internucleoside linkage; and

B is a nucleobase, nucleobase derivative, or nucleobase analog.

13. The chemically synthesized short interfering RNA of claim 12 wherein the passenger oligonucleotide comprises sequence-independent modification format (1), p is 0, x is 10, r is 2, and each m has structure (a) where R1 is O, R2 is O, and R3 is $CH_2$.

14. The chemically synthesized short interfering RNA of claim 1 wherein a 5'-end is further derivatized with a phosphate, $C_{1-12}$-alkyl, $C_{1-12}$-alkylamine, $C_{1-12}$-alkenyl, $C_{1-12}$-alkynyl, $C_{1-12}$-cycloalkyl, $C_{1-12}$-aralkyl, aryl, acyl, or silyl substituent.

15. The method of claim 8 wherein the contacting is in vivo contacting of an organ or an animal containing the cell with the chemically synthesized short interfering RNA.

\* \* \* \* \*